United States Patent [19]

John et al.

[11] Patent Number: 5,911,970
[45] Date of Patent: Jun. 15, 1999

[54] METHODS FOR CANCER IMAGING AND THERAPY USING BENZAMINE COMPOUNDS

[75] Inventors: Christy S. John, Gaithersburg; Jesse Baumgold, Bethesda; John G. McAfee, Chevy Chase; Terry Moody, Germantown; Wayne Bowen, Derwood, all of Md.

[73] Assignee: Research Corporation Technologies, Inc., Tucson, Ariz.

[21] Appl. No.: 08/426,366

[22] Filed: Apr. 21, 1995

Related U.S. Application Data

[63] Continuation-in-part of application No. 08/058,628, May 6, 1993, abandoned.

[51] Int. Cl.$^6$ .................. A61K 51/04; C07D 265/30; C07D 211/26
[52] U.S. Cl. .................. 424/1.85; 544/162; 546/229
[58] Field of Search .................. 424/1.85, 1.65; 546/229, 232; 564/366; 544/162; 548/561

[56] References Cited

U.S. PATENT DOCUMENTS

| | | | |
|---|---|---|---|
| 3,591,634 | 7/1971 | Thominet | 260/559 |
| 3,891,671 | 6/1975 | Thominet | 260/326.47 |
| 4,279,887 | 7/1981 | Baldwin et al. | 424/1.5 |
| 4,360,511 | 11/1982 | Baldwin et al. | 424/1.5 |
| 4,430,319 | 2/1984 | Blau et al. | 424/1.1 |
| 4,584,187 | 4/1986 | Wieland et al. | 424/1.1 |
| 4,615,876 | 10/1986 | Troutner et al. | 424/1.11 |
| 4,647,446 | 3/1987 | Sargent, III et al. | 424/1.1 |
| 4,673,686 | 6/1987 | Thominet et al. | 514/359 |
| 4,888,353 | 12/1989 | Lednicer et al. | 514/422 |
| 4,937,260 | 6/1990 | DePaulis et al. | 514/428 |
| 5,122,361 | 6/1992 | Kung et al. | 424/1.1 |
| 5,154,913 | 10/1992 | DePaulis et al. | 424/1.1 |
| 5,190,741 | 3/1993 | Moreau et al. | 424/1.1 |
| 5,213,787 | 5/1993 | Wilbur et al. | 424/1.11 |
| 5,349,063 | 9/1994 | Joshua et al. | 544/162 |

FOREIGN PATENT DOCUMENTS

| | | |
|---|---|---|
| 317 873 | 5/1989 | European Pat. Off. . |
| 317873 | 5/1989 | European Pat. Off. . |
| 393 838 | 10/1990 | European Pat. Off. . |
| 393838 | 10/1990 | European Pat. Off. . |
| 2642972 | 2/1989 | France . |
| 90/09170 | 8/1990 | WIPO . |
| WO 90/09170 | 8/1990 | WIPO . |
| 94/26314 | 11/1994 | WIPO . |
| WO 94/26314 | 11/1994 | WIPO . |

OTHER PUBLICATIONS

John et al. (1992) *J. Nuc. Med.* 33:889–890, Abstract #274.

John et a.. (1992) *Abstr. Pap. Am. Chem. Soc.* 204(1–2) .MEDI131.

Raymond A. Murphy, et al., "Synthesis and Characterization of Iodobenzamide Analogues:Potential D–2 Dopamine REceptor Imaging Agents", *J. Med. Chem.*, 1990, 33:171–178.

Mei–Ping Kung, et al.; "The Characterization of IBF as a New Selective Dopamine D–2 Receptor Imaging Agent", *J. Nuc. Med.*, 1990, 31:648–654.

M. Cordes, et al., "Initial experience with SPECT examinations using [123I] IBZM as a D2–dopamine receptor antagonist in Parkinson's disease", *European Journal of Radiology*: 12 (1991) :182–186.

Michelot, et al. (1991), *J. Nucl. Med.* 32: 1573–1580.

Meyniel, et al. (1990), *C.R. Acad. Sci.* Paris, t3ll, Serie III, 13–18.

C.S. John, et al., (1993), " A malignant Melanoma, Imaging Agent: Synthesis, Characterization, In Vitro Binding & Diodistribution of Iodind–125–(2–Piperidiny–laminoethyl)4–Iodobenzamide," *J. Nuc. Med.* 34: pp. 2169–2175.

Wojciech T. Bem, et al., (1991), "Overexpression of σ Receptors in Nonneural Human Tumors," *Cancer Research*, 51: pp. 6558–6562.

Xuao–shu He, et al., (1993), "Synthesis and Binding Characteristics of Potential SPECT Imaging Agents for σ–1 and σ–2 Binding Sites," *J. Med. Chem.* 36: pp. 566–571.

Brian R. de Costa, et al., (1992), "Synthesis Characterization, and Biological Evaluation of a Novel Class of N–(Arylethyl)–N–alkyl–2–1(1–pyrrolidinyl) ethylamines: Structural Requirements and Binding Affinity at the σ Receptor," *J. Med Chem.* 35:38–47.

Christy S. John, et al., (1994), "Synthesis and Characterization of [125I]–N–(N–Benzylpiperidin–4–yl)–4–iodobenzamide, A New σ Receptor . . . ," *J. MEd. Chem.* 37: pp. 1737–1739.

Bertold J. Vilner, et al., (1995), "Sigma–2 Receptors Are Expressed in a Wide Variety of Human and Rodent Tumor Cell Lines," *Cancer Research* 55: pp. 408–413.

Brian R. de Costa, et al., (1993), "Synthesis and Evaluation of Conformationally Restricted . . . ," *J. Med. Chem.* 36: pp.2311–2320.

S.M.N. Efange, et al., (1993), "Synthesis and Biological Evaluation of Radioiodinated N–2–94 . . . ," Nucl. Med. Biol. vol. 20: pp. 527–538.

C.S. John, et al., (1993), "an Improved Synthesis of [125I] N–. . . ," *Nucl. Med. Biol.* vol. 20, No. 1, pp. 75–79.

(List continued on next page.)

*Primary Examiner*—Jose' G. Dees
*Assistant Examiner*—Michael G. Hartley
*Attorney, Agent, or Firm*—Scully, Scott, Murphy & Presser

[57] ABSTRACT

The present invention relates to a class of compounds having affinity for certain cancer cells, e.g. lung carcinomas, colon carcinomas, renal carcinomas, prostate carcinomas, breast carcinomas, malignant melanomas, gliomas, neuroblastomas and pheochromocytomas. The compounds of the present invention can also bind with high specificity to cell surface sigma receptors and can therefore be used for diagnostic imaging of any tissue having an abundance of cells with sigma receptors. The present invention provides such compounds as agents for diagnostic imaging and for detecting and treating tumors containing the cancer cells described above.

42 Claims, 15 Drawing Sheets

OTHER PUBLICATIONS

T.W. Moody et al(1994), *Proceedings of the American Assoc, For Cancer Research* vol. 35: p. 266.

Ingrid Pettersson, et al., (1992), "Conformation Analysis of Dopamine D–2 Receptor Antagonists of the Benzamine Series in Relation to a Recently Proposed D–23 . . . ," *J. Med. Chem.* 35: pp. 23–55–2363.

Deborah Kotz, (1995), "Scintimammography: Magic Bullet or False Promise?", *The Journal of Nuclear Medicine* vol. 36: pp. 15N–19N.

Lamk M. Lamki, (1995), Tissue Characterizationin Nuclear Oncology: Its time has come,: *The Journal of Nuclear Mecicine* vol. 36: pp. 207–210.

John L. Arachibald, et al., (1994), "Benzamidioperidines. 3. Carbocylic Derivatives Related to Indoramin," *J. Med. Chem.* vol. 17: pp. 739–747.

Bertold J. Vilner, et al., (1994), "Cytotoxic Effects of Sigma Ligands: Sigma Receptor–mediated Alterations in Cellular Morphology and Viability,", *Neuroscience* Gal. 82–90.

Christy S. John, et al., (1995), "Synthesis and Pharmacological Characterization . . . ,", *Cancer Research* 55: pp. 3022–3027.

Christy S. John, et al. (1995), "Sigma Receptors Are Expressed in Human Non–Small Cell Lung Carcinoma,", *Life Sciences*, vol. 56, No. 26, pp. 2385–2392.

Christy S. John, et al., (1995), "Synthesis, Binding Characteristics and In–Vivo Clearance of . . . ,", *J. Med. Chem.* p. 6. (abstract book).

Christy S. John, et al., (1995), "Radiochemical Synthesis of 2–[I–125]BP and . . . ,", *J. Med. Chem.* 36: p. 124. (abstract book).

Christy S. John, et al., (1995), "Characterization of Sigma Receptors of Neural Tumor Cells Using Radioiodinated Benazmides,", *J. Med. Chem.* 36: p. 144 (abstract book).

Christy S. John, et al., (1995), "Synthesis and Character of (N–Benzylpiperidin–4 YL–4 . . . ,", *J. Med. Chem.* 35: p. 246 (abstract book).

Christy S. John, et al., (1995), "Sigma Receptors are Expressed in Non–small Cell Lung Carcinoma; Potential Use For Tumor Visualization,", *J. Med. Chem.* 35: p. 248.

Christy S. John et al., "Targeting Sigma Receptor Specific Radiopharmaceuticals at Human Malignant Breast Lung and Melanoma Cells for Early Detection of Cancer" (1994), *GWUMC 1st Annual GW Health Sciences Research Day*, Abstract 151.

J. Prieto, et al., "Synthesis and Pharmacological Properties of a Series of Antidopaminergic Piperidyl Benzamides", 1977, *J. Pharm. Pharmac.* 29:147–152.

Alan R. Fritzberg, et al., "Approaches to Radiolabeling of Antibodies for Diagnosis and Therapy of Cancer", 1988, *Pharm. Res.* 5(6):324–334.

Solomons, *Organic Chemistry*, 1988, p. 899, Print Without Publication Month.

6 hours

IPAB 24 hours

IDAB 6 hours

IDAB 24 hours

Scatchard Plot for Binding of [³H]DTG in MCF-7 Breast Cancer Cells

Scatchard Plot for 4-[$^{125}$I]BP Binding in MCF-7 Breast Cancer Cells

COMPETITION BINDING OF 4-[I-125]BP
WITH HALOPERIDOL IN BREAST TB SAMPLES

COMPETITION BINDING OF 2-[I125]BP
IN BREAST CANCER BIOPSY MEMBRANES

METHODS FOR CANCER IMAGING AND THERAPY USING BENZAMINE COMPOUNDS

This application is a continuation-in-part of application Ser. No, 08/058,628 filed May 6, 1993, now abandoned.

This invention was made with Governmental support under NIH Grant No. CA-58496 awarded by the National Institute of Health. The Government has certain rights in the invention.

FIELD OF THE INVENTION

The present invention relates to a class of compounds having particular affinity for a specific cell surface receptor prevalent on certain cancer cells, e.g. lung carcinomas, malignant melanomas, gliomas, neuroblastomas, pheochromocytomas, colon carcinomas, renal carcinomas, breast carcinomas, prostate carcinomas and the like. In particular the present invention provides such compounds as agents for detecting and treating tumors, particularly tumors having cancer cells which possess a cell surface sigma receptor.

BACKGROUND OF THE INVENTION

Lung carcinomas, malignant melanomas, gliomas, neuroblastomas, pheochromocytomas, colon, renal, prostate and breast carcinomas are aggressive forms of cancer, the early detection and treatment of which are of paramount importance. If left undetected or untreated for several years or even months the median survival time of patients having these types of cancers is dramatically reduced.

Of these cancers, lung cancer has lead to the highest number of fatalities. In 1992 alone, lung cancer caused about 165,000 deaths within the United States. Two major types of lung carcinomas are responsible for most of these deaths: small cell lung carcinomas (SCLC) and non-small cell lung carcinoma (NSCLC).

SCLC is a neuroendocrine tumor that secretes several peptide growth factors including bombesin/gastrin releasing peptide (BN/GRP). SCLC is responsive to chemotherapy and radiation therapy, but relapse occurs frequently, and the median survival time is only about one year.

NSCLC accounts for about 75% of all lung cancer cases and encompasses a variety carcinomas including adenocarcinomas, large cell carcinomas and squamous cell carcinomas. NSCLC tumors secrete transforming growth factor-alpha (TGF-α) to stimulate cancer cell proliferation. NSCLC is generally treated with chemotherapy and surgical resection. However the median survival time for patients with NSCLC is only about 5 years.

Melanomas are among the most serious manifestations of skin cancer and lead to a greater number of fatalities than any other form of skin cancer. Melanomas can metastasize through the lymphatic system to regional nodes and then via the blood to secondary sites on the skin or in the liver, lungs and brain. Whereas the prognosis for superficial spreading melanomas can be quite good, there is a much poorer prognosis for nodular melanomas in which distant metastases frequently form.

Breast cancer is a major cause of death for women, and estrogen receptors have been reported to play a major role in the development and growth of breast tumors. Deprivation of estrogen is one of the clinically effective methods for the treatment of breast cancer patients. Several growth factors such as insulin-like growth factor I (IGF-I), transforming growth factors (TGF-α and -β), epidermal growth factor (EGF), and platelet-derived growth factors have been shown to be involved in the growth and progression of human breast cancer cells. Some growth factors such as TGF-β act as inhibitors of tumor growth. Despite the development of numerous antiestrogen and other drugs, the clinical utility of antiestrogen is limited due to resistance by the tumor cells.

Many lives could be saved if lung carcinomas, melanomas, gliomas, neuroblastomas, pheochromocytomas, colon, prostate and renal carcinomas and breast tumors were detected and treated at an early stage. Moreover many patients are reluctant to undergo radical surgical or broad spectrum chemotherapy procedures which are frequently used to treat such cancers since these procedures can cause disfiguration or disablement.

Current techniques diagnose breast cancer by first identifying suspect tumors by single plane or 2D mammography screening. A biopsy is then required to differentiate tumors from other lesions. In the United States alone, 21 million mammographies are performed each year; 700,000 suspect tumors are biopsied and 182,000 women are diagnosed with breast cancer. This suggests that 400,000–500,000 women are subject to unnecessary biopsy each year.

Accordingly an outstanding need exists for highly selective and non-invasive procedures permitting early detection and treatment of cancer.

A variety of radiopharmaceuticals have been evaluated for diagnostic imaging. For example, Michelot, J. M. et al. (1991 *J. Nucl. Med.* 32:1573–1580; Meyniel G. et al. (1990 *C. R. Acad. Sci. Paris* 311(1):13–18; and French Patent Publication No. 2,642,972 by Morean et al. have disclose [$^{123}$I and $^{125}$I]N-(diethylaminoethyl)4-iodobenzamide (i.e. IDAB) for imaging malignant melanoma in humans. Unfortunately, the synthesis of IDAB is problematic and, more significantly, IDAB is taken up in high concentrations by non-melanoma cells in the liver and lung. Accordingly, IDAB does not have optimal specificity for melanoma cells and its uptake by non-tumor cells undermines its utility for routine screening of cancer.

U.S. Pat. No. 4,279,887 to Baldwin et al., U.S. Pat. No. 5,154,913 to De Paulis et al. and Murphy et al. (1990 *J. Med. Chem.* 33:171–178) disclose radioiodonated benzamide compounds for use in imaging the brain only, e.g. $^{123}$I-N-β-phenethyl-o-iodobenzamide or (S)-N-[(1-ethyl-2-pyrrolidinyl)methyl]-2-hydroxy-3-iodo-6-methoxybenzamide (IBZM). However, the structure and utility of the compounds disclosed by Baldwin et al., De Paulis et al. and Murphy et al. is distinct from those provide herein.

The present invention provides compounds which bind with high specificity and affinity to the cell surface of cancer cells. These compounds bind, for example, to receptors on the cancer cell surface. One such receptor is a sigma receptor. Sigma receptors are known to be present on neural tissues and certain immortalized neuroblastoma and glioma cell lines (Walker et al. 1990 Pharmacol. Reviews 42: 355–400; and Villner et al. 1992 in *Multiple Sigma and PCP Receptor Ligands: Mechanisms for Neuromodulation and Neuroprotection?* Kamenka et al., eds. NPP Books, pp 341–353). However, it has been surprisingly found by the present inventors that sigma receptors are prevalent on some types of cancer cells, e.g. neuroblastoma, melanoma, glioma, pheochromocytoma, colon, renal and lung carcinoma cells. Recently, John et al. have found that MCF-7 breast tumor cells express sigma receptors. (1994 *J. Med. Chem.* 37: 1737–1739). Therefore the compounds of the present invention are useful for detecting and treating tumors, e.g. those containing cells with sigma receptors.

The present compounds are also useful for diagnostic imaging any tissue having a sigma receptor, e.g., a neural tissue such as the brain or spinal cord.

SUMMARY OF THE INVENTION

The present invention provides a method for diagnosing a mammal for the presence of a mammalian tumor which includes administering to a mammal a diagnostic imaging amount of a compound of the present invention, and detecting binding of the compound to a tumor in the mammal. The compounds of the present invention are of the general formula I.

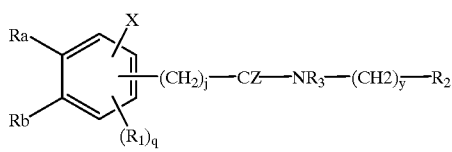

wherein:

X is a radionuclide;

Z is =O or two —H;

each $R_1$ is independently H, halo, lower alkyl or lower alkoxy;

$R_a$ and $R_b$ are independently H, halo, lower alkyl, lower alkoxy or $R_a$ and $R_b$ together with the carbon atoms to which they are attached form a cycloalkenyl or heterocyclic ring;

$R_2$ is —$N(R_3)_2$ or a 5 to 7 membered nitrogen containing heterocyclic ring which is unsubstituted or substituted with at least one alkyl or substituted or unsubstituted arylalkyl substituent;

each $R_3$ is independently hydrogen or lower alkyl;

j and y each are independently an integer from 0 to 6;

q is an integer from 0 to 2; and with the proviso that the compound is not an iodine radioisotope of (N-diethylaminoethyl)-4-iodobenzamide.

The present invention also provides a method for treating a mammalian tumor which includes administering to a mammal a composition including a tumor-inhibiting amount of a compound of formula I.

The present invention further provides a method for diagnostic imaging of a mammalian tissue which has cell surface sigma receptors which includes administering to a mammal a diagnostic imaging amount of a compound of the present invention and detecting an image of a tissue having an abundance of cells with sigma receptors.

A further aspect of the present invention provides a method for in vitro detection of a cancer cell in a mammalian tissue sample which includes contacting a mammalian tissue sample with an in vitro diagnostic imaging amount of a compound of formula I for a time and under conditions sufficient for binding of the compound to the cancer cell and detecting such binding.

Another aspect of the present invention provides a preferred compound of formula I, e.g. a compound of any one of formulae II, III or IV.

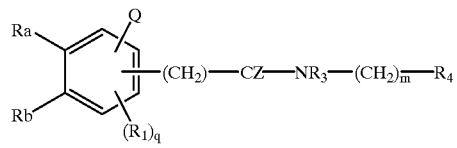

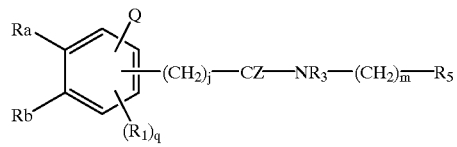

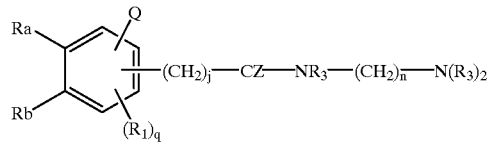

wherein Z, $R_a$, $R_b$, $R_1$, q, j are as described above;

Q is a radionuclide, halide or an activating group;

$R_4$ is —$N(R_3)_2$ or an N-linked 5 to 7 membered nitrogen containing heterocyclic ring which can have at least one alkyl or substituted or unsubstituted arylalkyl substituent, wherein each $R_3$ is independently lower alkyl or hydrogen;

$R_5$ is a 5 to 7 membered nitrogen containing heterocyclic ring which can have at least one alkyl or substituted or unsubstituted arylalkyl substituent;

m is an integer from 0 to 6;

n is an integer from 3 to 6. Such preferred compounds can also be used in the method of the present invention.

Compositions and kits containing the present compounds are also provided herein.

BRIEF DESCRIPTIONS OF THE DRAWINGS:

FIG. 1 illustrates the log molar amount of nonradioactive IPAB needed to competitively inhibit binding of radioactive IPAB to malignant melanoma cells. The $K_i$ obtained from these data was 6.8 nM.

FIG. 2A provides a scintigraphic image obtained at 6 hrs. after a nude mouse bearing a human malignant melanoma tumor received [$^{131}$I]PAB. The arrow indicates the implanted tumor.

FIG. 2B provides a scintigraphic image obtained at 24 hrs. after a nude mouse bearing a human malignant melanoma tumor received [$^{131}$I]PAB. The arrow indicates the implanted tumor.

FIG. 3A provides a scintigraphic image obtained at 6 hrs. after a nude mouse bearing a human malignant melanoma tumor received [$^{125}$I]DAB. The arrow indicates the implanted tumor.

FIG. 3B provides a scintigraphic image obtained at 24 hrs. after a nude mouse bearing a human malignant melanoma tumor received [$^{131}$I]DAB. The arrow indicates the implanted tumor.

FIG. 4 provides a scintigraphic image obtained at 30 hrs. after a nude mouse bearing a human lung adenocarcinoma tumor received [$^{131}$I]PAB. The arrow indicates the implanted tumor.

FIG. 5 provides the Scatchard plot for [$^3$H]DTG in MCF-7 breast cancer cells.

FIG. 6 provides the Scatchard plot for 4-[$^{125}$I]BP in MCF-7 breast cancer cells.

FIG. 7 provides a competition assay for the binding of 4-[$^{125}$I]BP with haloperidol in MCF-7 breast cancer cells.

FIG. 8 provides a competition assay for the binding of 2-[$^{125}$I]BP in MCF-7 breast cancer cells.

FIG. 9 provides a homologous competition assay for the binding of 2-[$^{125}$I]BP in MDA-MB-231 breast cancer cells.

FIG. 10 provides a homologous competition assay for the binding of 2-[$^{125}$I]BP in T47D breast cancer cells.

FIG. 11 provides a competition assay for the binding of [$^{125}$I]PEMP with BD 1008 in MCF-7 breast tumor cells.

FIG. 12 provides a competition assay for the binding of 4-[$^{125}$I]BP with haloperidol in breast TB samples.

FIG. 13 provides competition assay for the binding of 2-[$^{125}$I]BP in breast CA biopsy membranes.

DETAILED DESCRIPTION OF THE INVENTION

Figure 1:
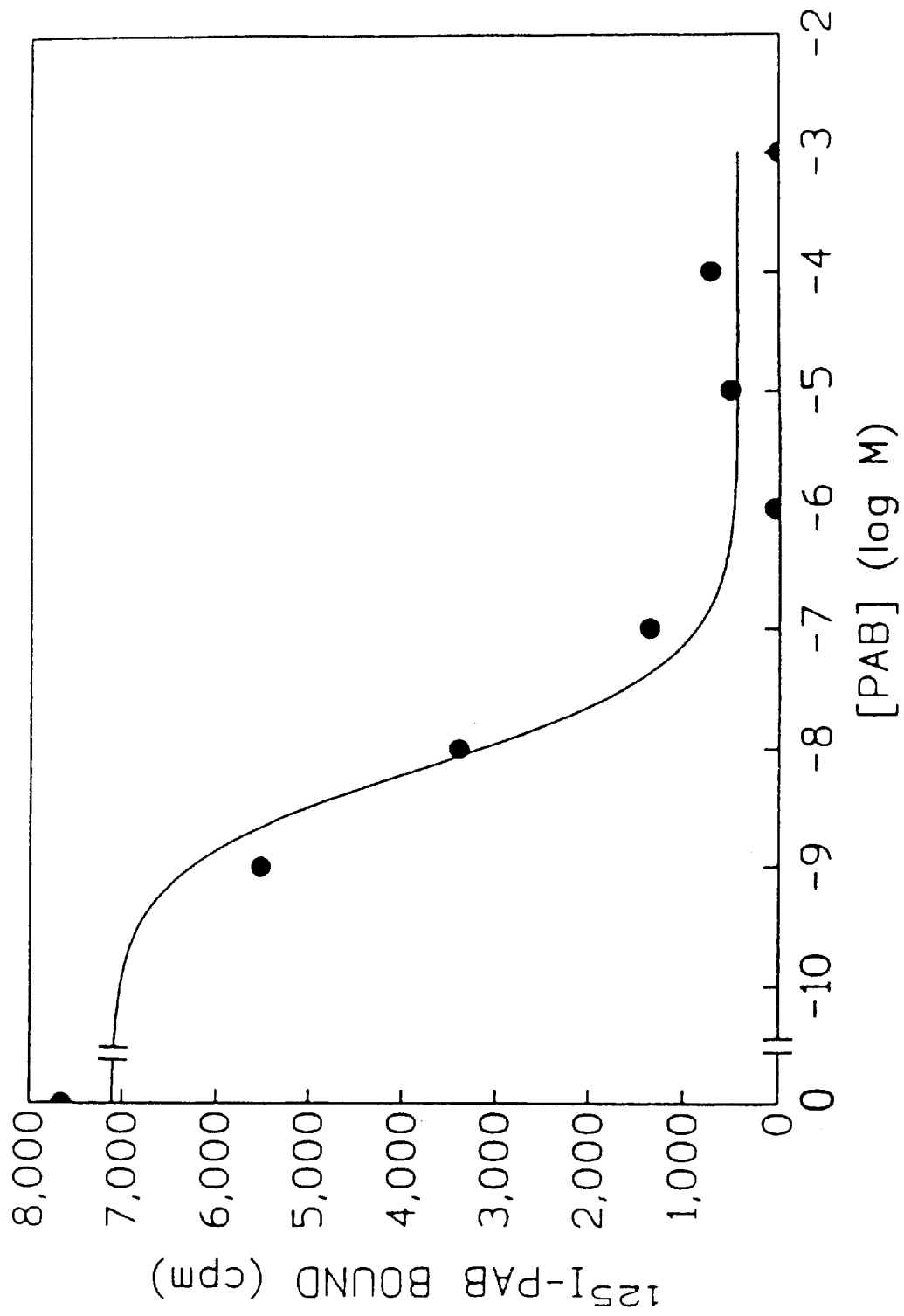

The present invention provides novel compounds and methods for detecting and treating certain types of cancer, e.g. neuroblastomas, gliomas, pheochromocytomas, melanomas, colon, renal, prostate, lung and breast carcinomas. The compounds of the present invention bind to a cell surface sigma receptor and exhibit exquisite cell specificity and affinity for the above cancerous cells and for cells having sigma receptors.

In one embodiment the present invention is directed to a method for detecting a mammalian tumor which includes administering to a mammal a diagnostic imaging amount of a compound of the present invention, and observing retention of the compound in a tissue of the mammal; wherein the compound is any one of formulae I, II, III or IV;

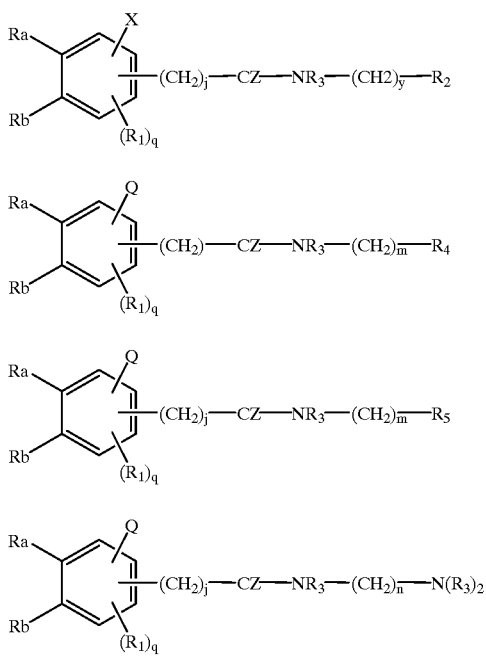

wherein:
X is a radionuclide;
Q is a radionuclide, halide or an activating group;
Z is =O or two —H;
each $R_1$ is independently H, halo, lower alkyl or lower alkoxy;
$R_a$ and $R_b$ are independently H, halo, lower alkyl, lower alkoxy or $R_a$ and $R_b$ together with the carbon atoms to which they are attached form a cycloalkenyl or heterocyclic ring;

$R_2$ is —N($R_3$)$_2$ or a 5 to 7 membered nitrogen containing heterocyclic ring which is unsubstituted or substituted with at least one alkyl or substituted or unsubstituted arylalkyl substituent;
each $R_3$ is independently hydrogen or lower alkyl;
$R_4$ is —N($R_3$)$_2$ or an N-linked 5 to 7 membered nitrogen containing heterocyclic ring which can have at least one alkyl substituent, wherein each $R_3$ is independently lower alkyl or hydrogen;
$R_5$ is a 5 to 7 membered nitrogen containing heterocyclic ring which can have at least one alkyl or substituted or unsubstituted arylalkyl substituent;
j and y are independently an integer from 0 to 6;
q is an integer from 0 to 2;
m is an integer from 0 to 6;
n is an integer from 3 to 6; and with the proviso that the compound is not an iodine radioisotope of (N-diethylaminoethyl)-4-iodobenzamide.

The present invention also provides a method for treating a mammalian tumor which includes administering to a mammal a composition including a tumor-inhibiting amount of a compound of formula I, II, III or IV.

The present invention further provides a method for diagnostic imaging of a mammalian tissue which has cell surface sigma receptors which includes administering to a mammal a diagnostic imaging amount of a compound of the present invention and detecting an image of a tissue having an abundance of cells with sigma receptors.

The present invention further provides a method for in vitro detection of a cancer cell in a mammalian tissue sample which includes contacting a mammalian tissue sample with an in vitro diagnostic imaging amount of a compound of formula I for a time and under conditions sufficient for binding of the compound to the cancer cell and detecting such binding.

When used for diagnostic imaging X or Q as a radionuclide is used. Moreover X or Q radionuclide groups which are preferably used for diagnostic imaging are γ-emitting radionuclides which can be detected by radioimaging procedures, e.g. by scintigraphic imaging. Such γ-emitting radionuclides emit radiation which is sufficiently penetrating to be detected through tissues. Moreover, for diagnostic imaging preferred radionuclides do not emit a particle, e.g. an α or β particle. Preferred X and Q groups for diagnostic imaging include $^{123}$I $^{124}$I $^{125}$I $^{131}$I $^{18}$F $^{76}$Br, $^{77}$Br, $^{99m}$Tc and $^{111}$In. $^{123}$I is especially preferred for diagnostic imaging.

When used for therapeutic purposes X or Q as a radionuclide is used. Preferably X and Q radionuclides employed for therapy are β-emitting or an α-emitting radionuclides. However, as contemplated herein, any cytotoxin which exhibits a localized cell killing activity can be used in place of an X or Q radionuclide. The preferred X and Q groups for treating cancers include $^{131}$I, $^{211}$At, $^{212}$Pb, $^{212}$Bi, $^{76}$Br, $^{77}$Br and the like. However, compounds for treating cancer more preferably have X or Q as $^{131}$I.

As provided herein Q is a radionuclide, a halide or an activating group. Compounds having Q as a halide or an activating group are provided as non-radioactive compounds of the present invention which can be readily converted into the corresponding radioactive compound. Since the utility of a radioactive compound relates to the specific activity of such a radioactive compound, it is often preferred to add the radionuclide just before use. Accordingly, compounds having Q as halide or as an activating group are provided, for example, in a form useful for storage or transport.

When Q is a halide, such a halide is preferably Br or I.

As provided herein an activating group is a group which is easily displaced by a radionuclide via electrophilic aromatic substitution. Preferred activating groups include tributyl-tin, trimethylsilyl, t-butyldimethylsilyl, iodide and the like.

According to the present invention Z is =O or two hydrogen atom substituents. Since the —CZ— moiety is adjacent to an amine, when Z is =O an amide (—CO—NH—) is formed. When Z is two hydrogen atoms a methylene (—CH$_2$—) is formed. Therefore compounds of the present invention can be amide or alkylamino compounds, e.g. compounds of formula I can have one of the following side chains:

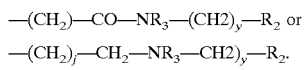

—(CH$_2$)$_j$—CO—NR$_3$—(CH2)$_y$—R$_2$ or

—(CH$_2$)$_j$—CH$_2$—NR$_3$—(CH2)$_y$—R$_2$.

In a preferred embodiment Z is =O, i.e., the —CZ— group forms a carbonyl. When —CZ—NR$_3$— is —CH$_2$—NR$_3$—, the R$_3$ is preferably an alkyl.

The term lower alkyl, when used singly or in combination, refers to alkyl groups containing one to six carbon atoms. Lower alkyls may be straight chain or branched and include such groups as methyl, ethyl, propyl, isopropyl, butyl, sec-butyl, isobutyl, t-butyl, pentyl, isopentyl, neopentyl, hexyl and the like. The preferred alkyl groups contain one to four carbon atoms.

As used herein, a lower alkylene, singly or in combination with other groups, contains up to six carbon atoms in the main chain and a total of 10 carbon atoms if the alkylene is branched. Lower alkylene groups include methylene, ethylene, propylene, isopropylene, butylene, t-butylene, sec-butylene, isobutylene, amylene, isoamylene, pentylene, isopentylene, hexylene and the like. The preferred lower alkylene groups contain one to four carbon atoms.

The term cycloalkenyl refers to a partially saturated cyclic structure, i.e., a ring, having 3–7 ring carbon atoms which can have one or two unsaturations. Since the cycloalkenyl groups of the present invention are fused to a phenyl moiety such cycloalkenyls are partially unsaturated. The subject cycloalkenyls groups include such groups as cyclopropenyl, cyclobutenyl, cyclopentenyl, cyclohexenyl and cycloheptenyl rings.

As used herein, lower alkoxy refers to a lower alkyl group attached to the main chain via an oxygen atom.

Halo refers to a halogen, especially bromine, iodine, chlorine and fluorine. As used herein a halo group is a commonly available, non-radioactive halogen isotope. Preferred halo groups include iodide, chloride, bromide and the like.

Aryl refers to a compound whose molecules have ring structures characteristic of benzene, naphthalene, phenanthrene, etc. These compounds have either the six-carbon ring of benzene or the condensed six-carbon rings of other aromatic derivatives. These compounds may be unsubstituted or substituted with halogens, alkoxy or alkyl groups. A preferred aryl group is phenyl, C$_6$H$_5$.

The term arylalkane refers to a compound containing both aliphatic and aryl structures. A preferred arylalkane is benzyl, CH$_2$C$_6$H$_5$. These compounds may be unsubstituted or substituted with halogens, alkoxy or alkyl groups.

As employed herein, a heterocyclic ring means a saturated, partially saturated or aromatic heterocyclic ring having at least one nitrogen or oxygen ring atom. As is known to the skilled artisan a saturated heterocyclic ring has no double bonds. As used herein a partially saturated heterocyclic ring can have at least one double bond.

The present heterocyclic rings can have up to three heteroatoms and up to a total of seven ring atoms. Accordingly, heterocyclic rings of the present invention can have about 2 to about 6 ring carbon atoms. Preferably, a heterocyclic ring has only one nitrogen or one oxygen heteroatom, or one nitrogen atom and one oxygen heteroatom. Heterocyclic rings can also have a mixture of nitrogen or oxygen heteroatoms, e.g. morpholine with one oxygen and one nitrogen. It is preferred that the heterocyclic ring contain one or two ring heteroatoms, most preferred is one ring nitrogen or oxygen heteroatom.

Heterocyclic rings of the present invention are monocyclic; such monocyclic rings can be fused to a phenyl ring to form a bicyclic ring.

Representative partially saturated and heteroaromatic heterocyclic rings include furan, pyran, oxazine, isoxazine, pyrrole, pyrazole, pyridine, pyrazine, triazole, tetrazole, triazine, pyrimidine, pyridazine, furazan and the like. Preferred heteroaromatic groups include pyridine and the like.

Representative saturated heterocyclic rings include tetrahydrofuran, pyrazolidine, imadazolidine, pyrrolidine, azetidine, piperidine, piperazine and morpholine. Preferred heterocyclic rings include piperidine and the like.

As used herein R$_a$ and R$_b$ are independently H, halo, lower alkyl, lower alkoxy or R$_a$ and R$_b$ together with the carbon atoms to which they are attached form a cycloalkenyl or heterocyclic ring. When R$_a$ and R$_b$ together form a cycloalkenyl or heterocyclic ring, such a ring is fused to the phenyl.

Such cycloalkenyl ring formed from R$_a$ and R$_b$ has only one unsaturation in the cycloalkenyl ring and that unsaturation is contributed by the phenyl ring to which the cycloalkenyl is fused. While a cycloalkenyl formed by R$_a$ and R$_b$ can be a 5 or 6 membered ring, such rings are preferably 5-membered rings., e.g. cyclopentenyl. Examples of the fused cycloalkenyl-phenyl ring include indanyl and tetrahydronaphthyl, e.g., 5,6,7,8-tetrahydronaphthyl, and the like.

When a heterocyclic ring is formed by R$_a$ and R$_b$, the heterocyclic ring preferably has one nitrogen or oxygen heteroatom and 5 or 6 ring atoms. As used herein, heterocyclic is as defined hereinabove. The heterocyclic ring contains at least two ring carbon atoms when the heterocyclic ring is a 5-membered ring, and the number of ring carbon atoms present can range from 2–4 carbon ring atoms. When the heterocyclic ring is a 6-membered ring, the number of ring carbon atoms can range from 2–5 carbon atoms. Thus, the total number of ring carbon atoms will range from 6–8 ring carbon atoms when the phenyl ring is fused to a 5-membered heterocyclic ring and 6–9 ring carbon atoms when the phenyl ring is fused to a 6-membered heterocyclic ring. The heterocyclic ring can contain up to 3 ring heteroatoms. The preferred ring heteroatoms are oxygen and nitrogen, especially oxygen. Preferred heterocyclic rings formed by R$_a$ and R$_b$ include dihydrofuranyl, dihydropyrrolyl, tetrahydropyridinyl and the like.

As provided herein each R$_1$ is independently H, halo, lower alkyl or lower alkoxy. In a preferred embodiment R$_1$ is H, halo or lower alkoxy. More preferred R$_1$ groups include H and halo. However, in one embodiment R$_1$ is preferably alkoxy.

The variable q is defined herein as an integer ranging from 0 to 2 which describes the number of R$_1$ groups on the phenyl moiety. Since the phenyl is also substituted with R$_a$, R$_b$, X (or Q) and a side chain amide or amine moiety, the maximal number or R$_1$ groups is 2 (i.e. q can maximally be 2). When q is less then 2 some positions on the phenyl group are unsubstituted; in this case a hydrogen is present at the positions having no R$_1$ group. Preferred values for q are 0 to 1. An especially preferred value for q is 0, i.e. the phenyl has hydrogen at all positions except those occupied by $R_a$, $R_b$, X (or Q) and the amide or amine side chain moiety.

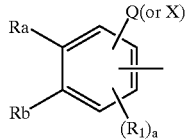

group is selected from the following:

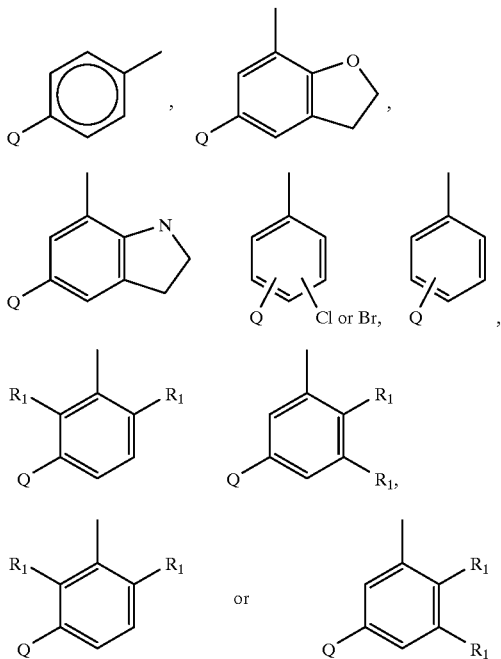

wherein $R_1$ is as described hereinabove and Q is a radionuclide (e.g. X), a halide or an activating group.

As described herein, $R_2$ is —$N(R_3)_2$ or a 5 to 7 membered nitrogen containing heterocyclic ring which is unsubstituted or substituted with at least one alkyl or substituted or unsubstituted arylalkyl substituent; wherein each $R_3$ is independently hydrogen or lower alkyl. Preferably $R_3$ is lower alkyl in the —$N(R_3)_2$ groups of the present invention. Preferred $R_2$ heterocyclic rings include N-piperidinyl, N-pyrrolidinyl, N-pyridinyl, N-morpholinyl, N-pyrrolyl, piperidinyl, pyrrolidinyl, pyridinyl, morpholinyl or pyrrolyl, which can be substituted with an $R_6$ lower alkyl or substituted or unsubstituted arylalkyl. $R_6$ is preferably attached to the nitrogen of the piperidinyl, pyrrolidinyl or morpholinyl rings. The arylalkyl compound may be unsubstituted or substituted with halogens, alkoxy or alkyl groups.

In one embodiment $R_2$ can be $R_4$ as defined herein. In another embodiment $R_2$ can be $R_5$ as defined herein. In still another embodiment $R_2$ can be —$N(R_3)_2$ as defined herein.

As provided herein, $R_4$ is —$N(R_3)_2$ or an N-linked 5 to 7 membered nitrogen containing heterocyclic ring which can have at least one alkyl substituent. As defined herein N-linked means that the nitrogen containing heterocyclic ring is attached to the main chain through a nitrogen atom. $R_4$ is used in formula II to indicate a preference for attachment of the nitrogen present within the heterocyclic ring to the main chain. Preferred $R_4$ heterocyclic rings include rings of the formulae:

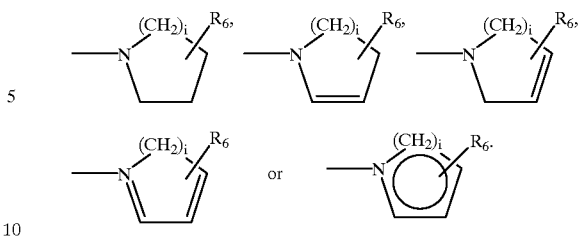

wherein $R_6$ is hydrogen or lower alkyl and each i is independently an integer from 1 to 3. Preferred $R_4$ heterocyclic rings include N-piperidinyl, N-pyrrolidinyl, N-pyridine and the like.

In another embodiment preferred compounds have heterocyclic rings that are not attached via the ring nitrogen. $R_5$ is used in formula III to describe such compounds, wherein $R_5$ is a 5 to 7 membered nitrogen containing heterocyclic ring which can have at least one alkyl or substituted or unsubstituted arylalkyl substituent. In a preferred embodiment $R_5$ is any one of the following:

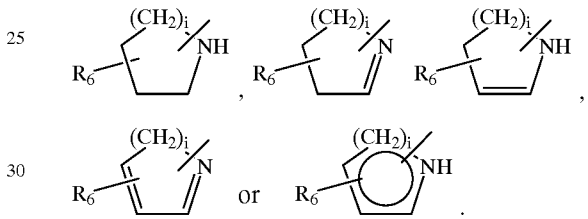

wherein each i is independently an integer from 1 to 3 and $R_6$ is hydrogen or lower alkyl or substituted or unsubstituted arylalkyl. More preferred $R_5$ heterocyclic rings include piperidinyl, pyrrolidinyl or pyridinyl which are N-substituted with an $R_6$ lower alkyl or substituted or unsubstituted arylalkyl. Such an $R_6$ lower alkyl is preferably methyl, ethyl, propyl or butyl. Such an $R_6$ arylalkyl is preferably benzyl. The arylalkyl compound may be unsubstituted or substituted with halogens, alkoxy or alkyl groups.

The compounds of formula IV have an —$N(R_3)_2$ group which is hydrogen or lower alkyl. In a preferred embodiment for —$N(R_3)$, $R_3$ is lower alkyl, e.g. methyl, ethyl, propyl or butyl.

The variable j, as used herein, refers to an integer ranging from 0 to 6 which defines the length of the alkylene chain separating the phenyl and —CZ— moieties of the present compounds. Preferably, j is an integer from 0 to 3. More preferably, j is an integer from 0 to 2. For compounds where —CZ— is —CO—, j is preferably 0.

As defined herein y is 0 to 6. The variable y defines the length of the alkylene chain separating the CZ—$NR_3$—and $R_2$ groups in the —CZ—$NR_3$—$(CH2)_y$—$R_2$ moiety of formula I. Preferably y is 0 to 3; more preferably y is 0 to 2.

Like y, the variable m defines the length of the alkylene chain separating the —CZ—$NR_3$— and the $R_4$ (or $R_5$) group in the —CZ—$NR_3$—$(CH2)_m$—$R_4$ (or $R_5$) moiety of formula II or III. The variable m is an integer ranging from 0 to 6. However, m is preferably to 4 and more preferably 0 to 3.

The length of the alkylene chain separating the —CZ—NH— and the —$N(R_3)_2$ moieties in formula IV is described herein by n. The variable n is an integer ranging from 3 to 6. In a preferred embodiment n is 3.

Preferred compounds of the present invention include the following:

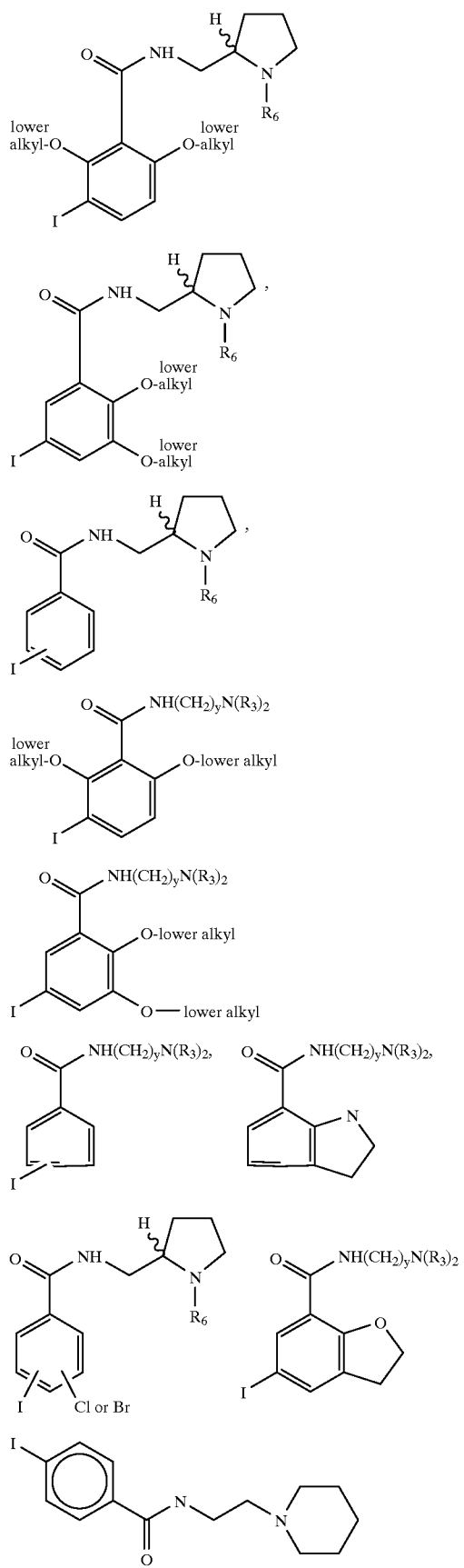

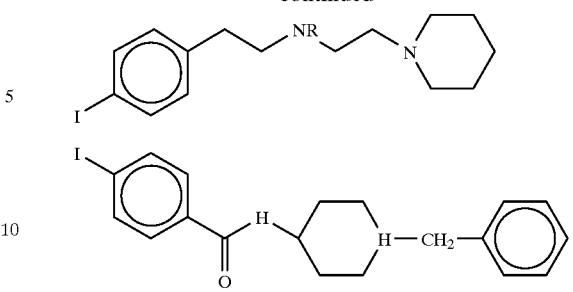

The various combinations and permutations of the Markush groups of X, Q, Z, $R_a$, $R_b$, $R_1$, $R_2$, $R_3$, $R_4$ and $R_5$ described herein are contemplated to be within the scope of the present invention. Moreover, the present invention also encompasses compounds and compositions which contain less than all of the elements in the Markush grouping. Thus, the present compounds and compositions contain one or more elements of each of the Markush groupings in X, Q, Z, $R_a$, $R_b$, $R_1$, $R_2$, $R_3$, $R_4$ and $R_5$ and the various combinations thereof. Thus, for example, the present invention contemplates that $R_2$ may be one or more of the substituents listed hereinabove or any and all of the substituents of $N(R_3)_2$, $R_4$ and $R_5$.

The present compounds can bind to a specific cell receptor prevalent on certain types of cancer cells. Such cancer cells include lung carcinoma, colon carcinoma, renal carcinoma, melanoma, glioma, pheochromocytoma, neuroblastoma, prostate carcinomas, breast carcinomas and related cells. An example of the cell receptor to which the present compounds bind is a cell surface sigma receptor.

The binding characteristics of the present compounds were determined by observing whether binding was inhibited by known sigma receptor antagonists. Many antagonists are known which have demonstrated binding specificities for a given cell surface receptor. Such antagonists can be tested as competitive inhibitors for cellular binding by compounds of the present invention. If a given antagonist is a competitive inhibitor the receptor to which the antagonist binds must also bind the subject compounds.

For example, as demonstrated by the present inventors, a malignant melanoma cell line binds the present compounds with strong specificity and affinity. Only antagonists which bind to the same site as the present compounds can inhibit binding of the subject compounds. Antagonists which can be tested include antagonists specific for cell receptors such as sigma (e.g. using SE2466-2), sigma-1 (e.g. fluphenazine at low concentrations), sigma-2 (e.g. fluphenazine at high concentrations), dopamine-1 (e.g. SCH23390), dopamine-2 (e.g. raclopride), melanocyte secreting hormone receptor (e.g. melanocyte secreting hormone peptide), 5-hydroxytryptamine-1 (e.g. mianserin), 5-hydroxytryptamine-1a (e.g. NAN-190), 5-hydroxytryptamine-1c (e.g. ketanserine), 5-hydroxytryptamine-2 (e.g. ketanserine and mianserin) and 5-hydroxytryptamine-3 (e.g. 3-tropanyldichloroben) cell receptors and the like.

As provided herein, antagonists with demonstrated binding specificity for cell surface sigma receptors (e.g. fluphenazine) can act as competitive binding inhibitors for compounds of the present invention. In contrast, antagonists that do not bind to cell surface sigma receptors cannot inhibit binding of the present compounds to melanoma cells. Therefore, the present compounds can bind to cell surface sigma receptors.

Cell types which have sigma receptors include normal neural tissues (e.g., brain, spinal cord and the like) as well as lung carcinoma, colon carcinoma, renal carcinoma, breast and prostate carcinoma, melanoma, pheochromocytoma, glioma, neuroblastoma, all other neural tumors and the like. For example, several lung carcinoma cell types have demonstrated binding affinity for the present compounds including an adenocarcinoma, a squamous carcinoma and large cell lung carcinoma cells. In a further example metastatic malignant melanoma cells have demonstrated high affinity and specificity for the present compounds. In a preferred embodiment the present compounds are used to detect and treat melanomas and non-small cell lung carcinoma (NSCLC). Such NSCLC cancers include lung adenocarcinoma, lung squamous cell carcinoma, large cell lung carcinoma and the like.

Breast cancer cells, particularly MCF-7, T47-D and MDA-MB231 tumor cells, have also demonstrated binding affinity for the present compounds. In a preferred embodiment, the present compounds are used to detect and treat breast cancer. In another preferred embodiment, the present compounds are used to detect breast cancer in women with dense breasts.

According to the present invention a method for detecting a mammalian tumor or a tissue containing cell surface sigma receptor includes administering to a mammal a composition including a diagnostic imaging amount of at least one of the present compounds. Such a diagnostic imaging amount is a dosage of at least one of the subject compounds which permits sufficient tumor or tissue localization of the compound to allow detection of the tumor or tissue. This dosage can range from about 1 $\mu$g to about 1 g of the compound per liter which can be administered in doses of about 1 ng/kg body weight to about 10 $\mu$g/kg body weight. Preferred dosages of the present compounds are in the range of about 10 ng to about 2 $\mu$g/kg for diagnostic imaging. Moreover, for diagnostic imaging the amount of radioactivity administered should be considered. Preferably about 0.1 millicuries (mCi) to about 20 mCi of radioactive compound is administered.

As described herein a tumor or tissue labeled with one or more of the present compounds can be detected using a radiation detector, e.g. a $\gamma$-radiation detector. One such procedure utilizes scintigraphy. Tomographic imaging procedures such as single photon emission computed tomography (SPECT) or positron emission tomography (PET) can also be used to improve visualization.

In another embodiment the present invention is directed to a method for treating a mammalian tumor which includes administering to a mammal a composition including a tumor-inhibiting amount of at least one compound of the present invention. Such a tumor-inhibiting amount is an amount of at least one of the subject compounds which permits sufficient tumor localization of the compound to diminish tumor growth or size. As provided herein tumor growth or size can be monitored by any known diagnostic imaging procedure, e.g. by using the present methods. This dosage can range from about 0.1 mmole/kg body weight to about 500 mmole/kg body weight. A preferred dosage is about 5 to about 50 mmole/kg body weight.

The amount of radioactivity administered can vary depending on the type of radionuclide. However, with this in mind the amount of radioactivity which is administered can vary from about 1 mCi to about 800 mCi. Preferably, about 10 mCi to about 600 mCi is administered.

Moreover when considering a dosage for diagnostic imaging or therapy, the specific activity of the radioactive compound should be taken into consideration. Such a specific activity is preferably very high, e.g. for $^{123}$I-labeled compounds the specific activity should be at least about 1,000 Ci/mM to about 220,000 Ci/mM. More preferably the specific activity for $^{123}$I-labeled compounds is, e.g. about 10,000 Ci/mM to about 220,000 Ci/mM.

In another embodiment the present invention provides a method for in vitro detection of a cancer cell in a mammalian tissue sample which includes contacting a mammalian tissue sample with an in vitro diagnostic imaging amount of a compound of any one of formulae I, II, III or IV for a time and under conditions sufficient for binding of the compound to a cell surface sigma receptor on the cancer cell and detecting such binding.

Samples can be collected by procedures known to the skilled artisan, e.g. by collecting a tissue biopsy or a body fluid, by aspirating for tracheal or pulmonary samples and the like.

As used herein any mammalian tissue can be tested in vitro. Preferred tissues for in vitro testing include lung, bronchial, lymph, skin, brain, liver, prostate, breast, any tumor of neural origin and the like. Samples can be sectioned, e.g. with a microtome, to facilitate microscopic examination and observation of bound compound. Samples can also be fixed with an appropriate fixative either before or after incubation with one of the present compounds to improve the histological quality of sample tissues.

Conditions sufficient for binding of the compound to a cell surface sigma receptor on the cancer cell include standard tissue culture conditions, i.e. samples can be cultured in vitro and incubated with one of the present compounds in physiological media. Such conditions are well known to the skilled artisan. Alternatively, samples can be fixed and then incubated with a compound of the present invention in an isotonic or physiological buffer.

An amount of at least one of the present compounds for in vitro detection of a cancer cell can range from about 1 ng/l to about 1000 $\mu$g/l. A preferred amount is about 1 $\mu$g/l to about 100 $\mu$g/l.

When the present compounds are used for in vitro diagnosis of cancer X or Q as a radionuclide is used. Preferable X and Q radionuclides for in vitro diagnosis of cancer include $^{125}$I, $^{18}$F, $—^{35}$S-alkyl, $—^{35}$SO$_3$, $—^{35}$SO$_4$, $—^{14}$COOH, $—^{14}$CH$_3$, $^3$H and the like.

For detection, of cellular binding of one of the present compounds, samples can be incubated in the presence of a selected compound, then washed and counted in a standard scintillation counter. Alternatively, samples can be dipped in photoemulsion and the signal detected under light microscopy after several days, as exposed silver grains.

Compounds of the present invention can be prepared by any procedure available to the skilled artisan using protecting groups, leaving groups, activating groups and the like as needed. Starting compounds can be chosen which have the desired $R_1$, $R_2$, $R_3$, $R_4$, $R_5$ and $R_6$ groups at the requisite positions. Alternatively, a leaving group may be used in place of the desired $R_1$, $R_2$, $R_3$, $R_4$, $R_5$ or $R_6$ group, and the appropriate group may replace the leaving group in a later synthetic step. Another alternative is to employ a protecting group on a reactive group which may be present on starting materials, e.g., an amine or similar reactive group on the chosen starting material. The use of leaving or protecting groups prevents undesirable side reactions from occurring, while permitting desired reactions to take place.

As is generally known in the art, and for the purposes of the present invention, a leaving group is defined as a group which is readily broken away from its union with a carbon atom. These groups are readily recognizable by one skilled in the art. Suitable leaving groups are generally electron attracting groups, either because of their electronegativity or because they have an inductive effect, and may include groups such as halides, $N_3$, HO-Aryl, or $HSO_3$-Aryl groups, and the like. For example, a leaving group can be present at the position of X or Q on a starting material for the present compounds; such a leaving group is preferably a halide, e.g. Br or I.

A protecting group is covalently bound to a reactive group to render the reactive group unreactive while allowing desired reactions to take place. To be useful, a protecting group must in addition be easily removed without chemically altering the remainder of the molecule, and must regenerate the correct structure of the reactive group. Examples of protecting groups effective with, for example, primary and secondary amino groups include acetyl, carbobenzoxy (cleaved by acid hydrolysis), benzyl (cleaved by catalytic hydrogenation), tertbutoxycarbonyl (cleaved by mild acid treatment) and 9-fluorenylmethoxycarbonyl (cleaved by secondary amines). A comprehensive review of useful protecting groups is provided in Greene, 1981 *Protective Groups in Organic Synthesis* (John Wiley & Sons, New York).

As provided herein an activating group is a group which is easily displaced by a radionuclide via electrophilic aromatic substitution. The activating group is used to facilitate substitution of a radionuclide onto the present compounds. Activating groups contemplated by the present invention include tributyl-tin, trimethylsilyl, t-butyldimethylsilyl, iodide and the like.

The present compounds can be prepared from readily available starting materials, for example, by amidation of a substituted phenylalkyl acid or a substituted benzoic acid with an appropriate amine. Such a reaction yields a compound of any one of formulae I to IV.

In an exemplary procedure for synthesis of a benzamide compound of formula I, a substituted phenylalkyl acid or substituted benzoic acid can be used as a starting material. For example, a substituted phenylalkyl acid or substituted benzoic acid (V) having a leaving group (Y) at the desired X (or Q) position can be amidated in the presence of a halogenating reagent with an amine of formula VI, as depicted below.

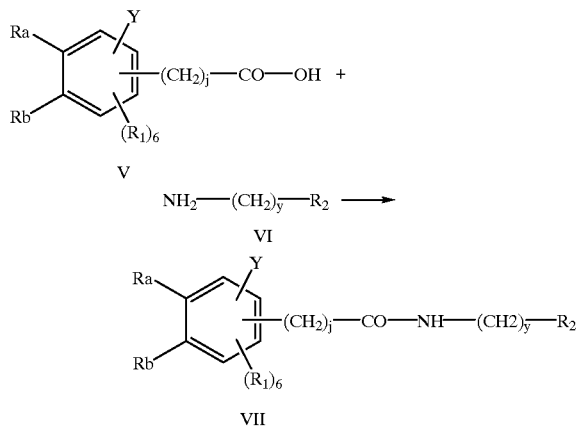

wherein Y is a leaving group and $R_1$, $R_a$, $R_b$, q, j, y and $R_2$ are as described hereinabove. Preferably Y is a halo group, e.g. Cl, Br or I. More preferred Y groups are Br in a meta position and I in a para position relative to the carboxyl group, when the X or Q is to be placed in such a respective meta or para position.

Halogenating reagents for the above described reaction include those which can convert the carboxylate to an acid halide, e.g. thionyl halide such as $SOCl_2$, $PCl_5$, $PCl_3$ and the like. A preferred halogenating reagent is $SOCl_2$ in the presence of dimethylformamide.

To facilitate formation of such an acid halide, the reaction can be heated to reflux temperatures. A preferred solvent for this reaction is a nonpolar volatile solvent, e.g. chloroform. The acid chloride so formed is sufficiently stable to be isolated, for example, by evaporation of solvent. After conversion of V to the acid halide, the amine (e.g. VI) can be condensed with the halide in the presence of a base such as triethylamine. The solvent for this reaction is also preferably a nonpolar solvent, e.g. chloroform.

The skilled artisan can readily modify the reactions described above to generate a compound of any one of formulae I, II, III or IV. For example, to produce a compound of formula II, an amine of the formula $NH_2-(CH_2)_m-R_4$ can be used in place of the compound of formula VI. Similarly, to produce a compound of formula III or IV, an amine of the formula $NH_2-(CH_2)_m-R_5$ or $NH_2-(CH_2)_n-N(R_3)_2$, respectively, can be used in place of VI.

When Z is =O, the leaving group (Y) can be directly replaced to produce a compound of any one of formulae I, II, III or IV. When Z is two —H, the carbonyl of the amide moiety formed by the above condensation must be converted into a methylene. To convert the —CO—NH— to a —CH$_2$—NH— a reducing agent can be used, e.g. boron hydride, sodium borohydrate, lithium aluminum hydride and the like. More preferred reducing agents are boron hydride (BH$_3$) or lithium aluminum hydride (LAH) in the presence of tetrahydrofuran (THF). For example, the carbonyl of a compound of formula VII can be converted to a methylene by the following reaction:

When the $R_3$ of —CZ—NR$_3$— is lower alkyl, such a lower alkyl is added, e.g. by alkylation, after condensation of the acid halide and the amine and after conversion of the amide (—CO—NH—) to the alkylamine (—CH$_2$—NH—). Alkylation can be done by any available procedure, e.g., using an alkyl halide with a sodium salt in dimethylformamide or ethanol. For example, an alkyl halide (e.g. iodomethane) can be reacted with a compound of formula VIII in the presence of sodium bicarbonate or sodium carbonate using dimethylformamide as solvent.

If a compound of any one of formulae II, III or IV is desired, a Q group can replace the Y leaving group, e.g. on VII or VIII. As provided herein Q is a radionuclide, a halide or an activating group. When Q is a halide a starting material having the desired halide at the position of Q can be utilized, e.g. V can be bromophenyl alkyl acid, iodophenyl alkyl acid, iodobenzoic acid, and the like. An activating group can be placed at the position of Y by available procedures to generate a compound of any one of formulae II, III or IV, wherein Q is the activating group. The activating group (Q) can in turn be readily replaced by a radionuclide (i.e. X) to generate compounds of formulae I, II, III or IV, wherein X is the desired radionuclide.

For example, activation can be achieved using palladium catalyzed stannylation with bis(tributyltin), as depicted below.

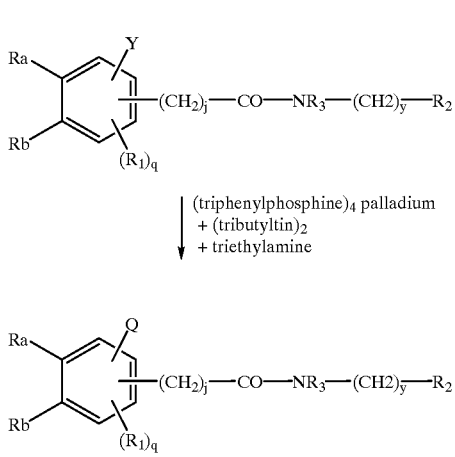

In this case Q is tributyltin ($Bu_3Sn$). This reaction is effective whether Z is =O or two —H.

When using t-butyldimethylsilyl chloride (TBDMSCl) or trimethylsilyl chloride with N-butyl lithium or t-butyl lithium, a protecting group ($R_7$) is first placed on the —CZ—$NR_3$— amine, if $R_3$ is hydrogen. When the $R_3$ of the —CZ—$NR_3$ is lower alkyl, no such protecting group is needed. Protecting groups used for a —CZ—$NR_3$—amine can be any protecting group for a secondary amine, e.g. carbobenzoxy (i.e. CBz, cleaved by acid hydrolysis), benzyl (cleaved by catalytic hydrogenation), tert-butoxycarbonyl (i.e. t-BOC, cleaved by mild acid treatment) and the like. The silylation reaction can be then be performed as depicted below, e.g. using an amine protected compound of formula VIII.

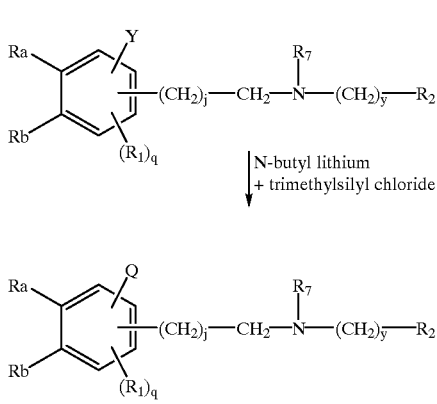

In this case Q is trimethylsilane ($Me_3Si$). The conditions used for this reaction include low temperature (e.g. −78° C.) and a polar solvent (e.g. tetrahydrofuran).

The $R_7$ group can be removed by standard techniques, e.g. when $R_7$ is CBz or t-BOC acid hydrolysis can remove $R_7$ and restore the secondary amine (—NH—). Silylation is preferred for compounds wherein Z is two —H.

The radioactively labeled compounds of the present invention can be produced with high specific activity and high yield by reacting a radioisotope (e.g. $^{123}I$, $^{125}I$ or I) with an activated intermediate (e.g. a compound of formula IX or X) in the presence of an oxidizing agent. Any oxidizing reagent which can convert the negatively charged radionuclide to a positively charged radionuclide can be used. Preferred oxidizing reagents include iodogen beads, peroxides such as peracetic acid, hydrogen peroxide and the like, as well as N-chloro-4-toluene-sulfonamide (i.e. chloramine-T). A more preferred oxidizing reagent is chloramine-T. An acid, e.g. HCl, can also be added.

An example of a reaction where the radionuclide replaces the activating group is depicted below using, e.g. a compound of formula IX.

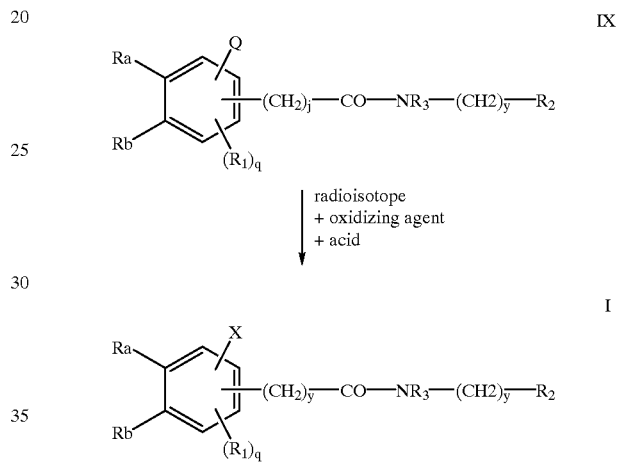

When $R_a$ and $R_b$ together with the carbon atoms to which they are attached form a cycloalkenyl or heterocyclic ring the desired cycloalkenyl or heterocyclic ring can be in place on the starting material. For example, the $R_a$ and $R_b$ of formula V together with the carbon atoms to which they are attached can form the desired cycloalkenyl or heterocyclic ring.

As is recognized by the skilled artisan, the above procedures can be modified for making the present compounds to include other known and commonly available procedures. The procedures provided herein are intended to be illustrative and are not exhaustive; therefore the illustrated procedures should not be viewed as limiting the invention in any way.

Another embodiment of the present invention provides a compartmentalized kit for detection of a mammalian tumor which includes a first container adapted to contain at least one of the compounds of the present invention.

A further embodiment of the present invention provides a compartmentalized kit for treating a mammalian tumor which includes a first container adapted to contain at least one of the compounds of the present invention.

Compounds of the present invention which are provided in a kit for detecting or treating a mammalian tumor can have any one of formulae I, II, III, IV, VII, VIII, IX or X. However more preferred compounds for the present kits are of any one of formulae II, III, IV, VII, VIII or IX. Especially preferred compounds of the present invention which placed in kits include compounds of formula II or IX.

Compounds provided in the present kits preferably have a Q rather than an X group and such a Q group is preferably an activating group. Activating groups present on compounds provided in the subject kits include tributyl-tin, trimethylsilyl or t-butyldimethylsily. Tributyl-tin is an especially preferred activating group for compounds provided in the present kits.

The kits of the present invention can be adapted to contain another container having a reagent for replacing an activating group with a radionuclide. For example, such a reagent can be an oxidizing reagent, e.g. chloramine-T.

Preferred radiolabeled compounds of the present invention include $^{125}$I-(2-piperidinylaminoethyl)-4-iodobenzamide ([$^{125}$I]PAB), $^{125}$I-(N-benzylpiperidin-4-yl)-4-iodobenzamide (4-[$^{125}$I]BP), $^{125}$I-(N-benzylpiperidin-4-yl)-3-iodobenzamide (3-[$^{125}$I]BP), $^{125}$I-(N-benzylpiperidin-4-yl)-2-iodobenzamide (2-[$^{125}$I]BP) and N-4-[$^{125}$I-iodophenyl)ethyl]-N-methyl-2-(1-piperidinyl)ethylamine (4-[$^{125}$I]PEMP).

Especially preferred radiolabeled compounds include [$^{125}$I]PAB, 2-[$^{125}$I]BP, 4-[$^{125}$I]BP and 4-[$^{125}$I]PEMP.

In a further embodiment, the kits of the present invention can be adapted to contain another container having a material for separating unattached radionuclide from the radiolabeled compounds of the present invention having an attached X group. Such a material can be any chromatographic material including a thin layer chromatography plate, a molecular exclusion resin, a silica gel, a reverse phase resin and the like. For convenience, such resins can also be provided in the form of a prepacked column.

The present compounds can be administered to a mammal as a pharmaceutical composition. Such pharmaceutical compositions contain a diagnostic imaging or an anti-tumor amount of at least one of the present compounds together with a pharmaceutically acceptable carrier.

The compositions can be administered by well-known routes including oral, intravenous, intramuscular, intranasal, intradermal, subcutaneous, parenteral, enteral, topical and the like. Depending on the route of administration, the pharmaceutical composition may require protective coatings.

The subject compounds may be incorporated into a cream, solution or suspension for topical administration.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water, buffered aqueous solutions (i.e., biocompatible buffers), ethanol, polyol (glycerol, propylene glycol, polyethylene glycol and the like), suitable mixtures thereof, surfactants or vegetable oils. Sterilization can be accomplished by any art recognized technique, including but not limited to, addition of antibacterial of antifungal agents, for example, paraben, chlorobutanol, phenol, sorbic acid, thimerosal, and the like. Further, isotonic agents, such as sugars or sodium chloride may be incorporated in the subject compositions.

Production of sterile injectable solutions containing at least one of the present compounds is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the present compounds are administered orally, the pharmaceutical compositions containing an effective dosage of the compound, can also contain an inert diluent, an assimilable edible carrier and the like. orally administered compositions can be provided in hard or soft shell gelatin capsules, tablets, elixirs, suspensions, syrups and the like.

The subject compounds are thus prepared for convenient and effective administration in pharmaceutically effective amounts with a suitable pharmaceutically acceptable carrier in a dosage which permits diagnostic imaging or cancer cell death. These amounts are preferably about 1 μg to about 1 g of the compound per liter and are administered in doses of about 1 ng/kg body weight to about 10 μg/kg body weight, or from about 0.1 mmole/kg body weight to about 500 mmole/kg body weight. Preferred compositions provide effective dosages of the present compounds in the range of about 10 ng to about 2 μg/kg for diagnostics and preferably about 5 to about 50 mmole/kg body weight for therapy.

Moreover when considering a dosage for diagnostic imaging of therapy, the specific activity of the radioactive compound should be taken into consideration. Such a specific activity is preferably very high, e.g. for $^{123}$I-labeled compounds the specific activity should be at least about 1,000 Ci/mM to about 240,000 Ci/mM. More preferably the specific activity for $^{123}$I-labeled compounds is, e.g. about 10,000 Ci/mM to about 220,000 Ci/mM.

As used herein, a pharmaceutically acceptable carrier includes solvents, dispersion media, coatings, antibacterial and antifungal agents, isotonic agents, and the like which are physiologically acceptable. The use of such media and agents are well-known in the art.

The following Examples further illustrate the invention.

EXAMPLE 1

Synthesis of $^{125}$I-2-(PiperidinylAminoethyl)-4-IodoBenzamide

Materials and Methods

Melting points were determined with a Fisher-Johns apparatus. $^1$H and $^{13}$C NMR spectra were recorded on a Brucker 300 AM spectrometer. Unless noted, chemical shifts were expressed as ppm using tetramethylsilane as an internal standard. The thin layer chromatography (TLC) system consisted of Analtech uniplate silica gel GF plates (250 microns, 10×20 cm), using $CHCl_3$/MeOH:80/20 as solvent. Radioactive spots were scanned and recorded by a Bioscan 300 imaging scanner equipped with automatic plate reader. Mass spectra (chemical ionization) were recorded on Finnigan 1015 mass spectrometer. Na$^{131}$I was obtained from duPont NEN and Na$^{125}$I was obtained from Bristol Meyers Squibb. Elemental analyses were performed by Galbraith Laboratory of Knoxville, Tenn.

Preparation of (2-piperidinylaminoethyl)-4-bromobenzamide (A)

A round bottom flask was charged with 4-bromobenzoic acid (2.0 g, 9.95 mmol) in chloroform (150 mL). To the solution was added thionyl chloride (3 mL) in chloroform (10 mL), 2–3 drops of dimethylformamide (DMF). The slurry was heated at reflux for 3 hr. while monitoring the reaction through a bubbler. A clear solution of 4-bromobenzoyl chloride was obtained, the volatiles were removed and a light yellow oil was obtained which solidified upon cooling.

The 4-bromobenzoyl chloride was dissolved in chloroform (30 mL) and added to a flask containing 1-(2-aminoethyl)-piperidine (1.29 g, 10 mmol) in chloroform (20 mL) and triethylamine (10 mL). The mixture was stirred at room temperature for 1 hr. and the volatiles were removed in vacuo. The resulting slurry was washed with 2% sodium bicarbonate (2×50 mL). The organics were dissolved in CHCl$_3$ (100 mL), separated from aqueous layer and dried over anhydrous Na$_2$SO$_4$. The solvent was removed to give a colorless solid (A, 2.7 g, yield, 87%). Rf (CHCl$_3$/MeOH:90/10) 0.45. $^1$H R (δ ppm): 1.46 (t, 2H, CH$_2$); 1.54 (broad m, 4H, CH$_2$); 2.43 (broad s, 4H, NCH$_2$); 2.52–2.56 (t, 2H, NCH$_2$); 2.68 (m, 2H, NCH$_2$); 3.49–3.53 (dt, 2H, NCH$_2$); 7.21 (bs, 1H, NH); 7.52–7.55 (m, 2H, arom); 7.65–7.68 (m, 2H, arom).

Preparation of (2-piperidinylaminoethyl)4-iodobenzamide, (B)

This was prepared using a procedure like that described above for A but using 4-iodobenzoic acid as starting material. A white solid (B) was obtained in 89% yield. $^1$H R (δ ppm): 1.43–1.45 (broad m, 2H, NCH$_2$); 1.53–1.60 (broad m, 4H, NCH$_2$); 2.41 (broad m, 4H, NCH$_2$); 2.50–2.54 (t, 2H, J=7.8 Hz, NCH$_2$); 3.44–3.48 (dt, 2H, NCH$_2$); 7.02 (bs, 1H, NH); 7.47–7.49 (m, 2H, arom.); 7.73–7.76 (m, 2H, arom.). m.p. 114–115 C. Anal C$_{14}$H$_{19}$N$_2$OI calcd. C, 46.91; H, 5.31; N, 7.82, found C, 46.91; H, 5.42; N, 7.68.

Preparation of (2-piperidinylaminoethyl)4-tributyltinbenzamide, (C)

A flame dried flask was charged with 4-bromobenzamide (1.0 g, 3.21 mmol) in triethylamine (40 mL). Tetrakis(triphenylphosphine) palladium (370 mg, 0.321 mmol), and bistributyltin (2.4 g, 3.80 mmol) were added, and the mixture was refluxed under nitrogen for 12 hr. The mixture was cooled, solvents decanted from the black residue, and the volatiles were removed in vacuo. The resulting black oil was passed through a silica gel column with elution with CHCl$_3$ (100 mL), followed by elution with CHCl$_3$/MeOH: 90/10. The desired fractions, as characterized by thin layer chromatography, were pooled and solvent was evaporated to give an oil (C, 0.4 g, 56%). m/e=523 (M$^+$+H) (100%); 233 (M$^+$-SnBu$_3$) (40%). $^1$H NMR (δ ppm): 0.82–0.93 (m, 16H, Bu$_3$ and CH$_2$); 1.01–1.05 (m, 4H, Bu$_3$); 1.22–1.37 (m, 8H, Bu$_3$); 1.45–1.67 (m, 8H, piperidinyl ring); 2.49–2.51 (t, 2H, NCH$_2$ piperdinyl ring); 2.60–2.63 (t, 2H, J=6 Hz, NCH$_2$); 3.53–3.58 (dt, 2H, J=5.34 Hz, NCH$_2$); 7.30–7.41 (bs, 1H, NH); 7.49–7.78 (m, 4H, arom). $^{13}$C R (∂, ppm): 9.60, 13.58, 25.743, 27.30, 29.00, 36.09, 54.29, 57.15, 126.03, 128.39, 132.00, 136.54, 167.69.

Radiolabeling of n-tributyltin PAB (C) with I-125 to Yield $^{125}$I(2-piperidinylaminoethyl)4-iodobenzamide (D)

To 100 μL of an ethanolic solution of (2-piperidinylaminoethyl)4-tributyltinbenzamide (1 mg/ml), was added a solution of [$^{125}$I] sodium iodide (1.5 mCi, 3 μL) in 0.1N NaOH, followed by the addition of 0.05N HCl (50 μL) to adjust the pH of the solution to pH 4.5–6. Fifty μL of a freshly prepared solution of N-chloro-4-toluenesulfonamide sodium monohydrate chloramine-T (1 mg/ml) was added to the above mixture. The contents were stirred for 10–15 minutes at room temperature and 100 μL of a solution of sodium metabisulfite (200 mg/ml) were added. The reaction mixture was neutralized with a saturated solution of NaHCO$_3$ (0.2 mL). 0.4 mL of normal saline was added and the organics were extracted in CHCl$_3$ (1.0 mL) after vortexing 30 seconds. The chloroform layer was evaporated in a stream of nitrogen. The radioactivity of the aqueous layer and the organic residue was counted. The total recovered radioactivity in the residue ranged from 74 to 89% (n=6). The residue (D) was dissolved in 90% ethanol, and 10% 0.01M phosphate buffer (400 μL). A portion of D was spotted on a TLC-SG plate along with a sample of nonradioactive (2-piperidinylaminoethyl)4-iodobenzamide (B, as above). The TLC-SG plates were developed with CHCl$_3$/MeOH: 90/10 (Rf=0.45). Another portion of D was injected into a Gilson HPLC fitted with a Waters Z-module radial compression separation system containing a micro Bonda-Pak C-18 reverse phase column equipped with Rheodyne 4125 injector (0.5 mL loop). The retention time for D ($^{125}$I-PAB) using isocratic elution with 90/10 EtOH/0.1M phosphate buffer (pH=6.7) at a flow rate of 1 mL/min. was 8.5 min., a value identical to that of non-radioactive (2-piperidinylaminoethyl)4-iodobenzamide.

Radiolabeling of n-tributyltin PAB (C) with $^{131}$I Yield $^{131}$I (2-piperidinylaminoethyl)4-iodobenzamide (E)

The same protocol as described above for $^{125}$I(2-piperidinylaminoethyl)4-iodobenzamide (D) was used except that the amount of 0.05N HCl added to adjust pH between 4.5–6 was different due to different concentration of aqueous sodium hydroxide solution in which Na$^{131}$I was commercially supplied. The workup of and the purification of $^{131}$I(2-piperidinylaminoethyl)4-iodobenzamide (E) was identical to $^{125}$I(2-piperidinylaminoethyl)4-iodobenzamide (D) above.

The reactions described hereinabove are depicted in Reaction Scheme I.

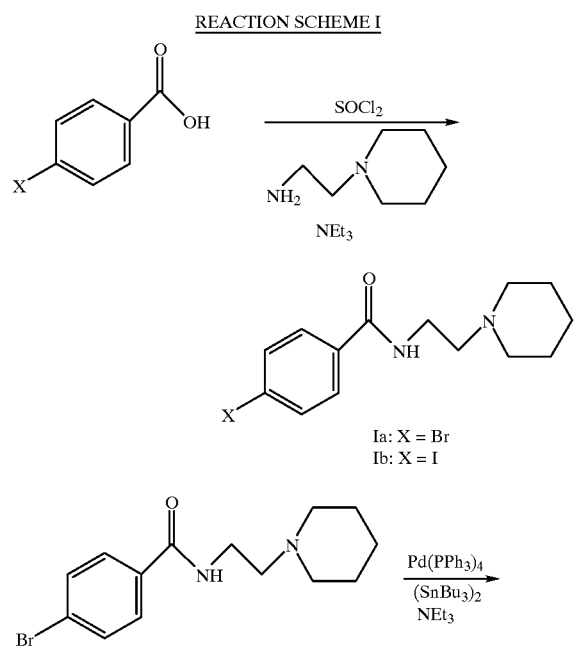

REACTION SCHEME I

Ia: X = Br
Ib: X = I

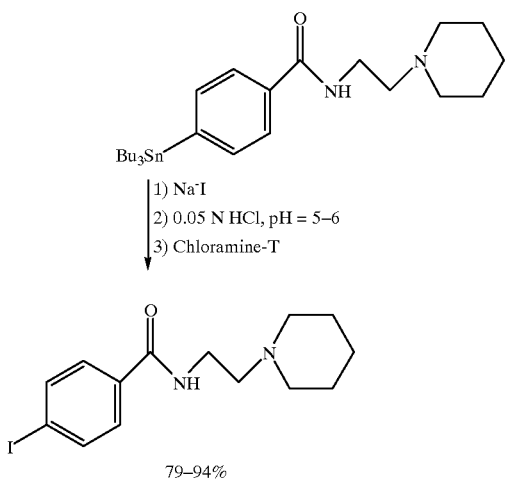

79-94%

EXAMPLE 2

Synthesis of 5-iodo-(N,N-diethylaminoethyl)-2,3-dihydrobenzofuran-7-carboxamide

Materials and Methods

Melting points were determined with a Fisher-Johns apparatus. $^1$H and $^{13}$C R spectra were recorded on a Brucker 300 AM spectrometer. Unless noted, chemical shifts were expressed as ppm using tetramethylsilane as an internal standard. The thin layer chromatography (TLC) system consisted of Analtech uniplate silica gel GF plates (250 microns, 10×20 cm), using CHCl$_3$/MeOH:80/20 as solvent. Radioactive spots were scanned and recorded by a Bioscan 300 imaging scanner equipped with automatic late reader. Mass spectra (chemical ionization) were recorded on Finnigan 1015 mass spectrometer. Na $^{131}$I was obtained from duPont NEN and Na$^{125}$I was obtained from Bristol Meyers Squibb. Elemental analyses were performed by Galbraith Laboratory of Knoxville, Tenn.

Synthesis of 5,7-dibromo-2,3-dihydrobenzofuran (F)

To a solution 2,3-dihydrobenzofuran (25 g, 0.21 mol) in chloroform (100 mL) was added dropwise at 0° C., a solution of bromine (67 g, 0.42 mol) with stirring. The reaction mixture was stirred overnight at room temperature. The excess bromine was destroyed by addition of a saturated solution of sodium thiosulfate (30 ml). The organic layer was separated from the inorganic layer and washed with 2% sodium bicarbonate (2×50 ml), then dried over anhydrous sodium sulfate. The volatiles were removed in vacuo to provide a light yellow oil (51 g, 87%). $^1$H NMR (CDCl$_3$) δ ppm: 3.21–3.27 (t, J=9 Hz, 2H, CH$_2$): 4.57–4.63 (t, J=9 Hz, 2H, OCH$_2$): 7.14–7.15 (t, 1H, arom.): 7.32–7.33 (t, 1H, arom.)

Synthesis of 5-bromo-7-carboxy-2,3-dihydrobenzofuran (G)

To the above dibromo compound (15 g, 53.9 mmol) was added anhydrous tetrahydrofuran (50 ml). The solution was cooled at −78° C. under nitrogen atmosphere. A solution of n-butyl-lithium (2.0M. 27 ml) was added to the mixture dropwise. The mixture turned light yellow brown. After 5 minute of stirring at −78° C., carbon dioxide was bubbled through the mixture, giving a straw yellow color to the mixture. The mixture was then warmed up to room temperature and stirred for 30 minutes. A dirty white color solid was obtained upon filtration (7.0 g, 53%). $^1$H NMR (d$^6$-DMSO) δ ppm: 2.85–2.95 (t, J=9 Hz, 2H, CH$_2$: 4.35–4.45 (t, J=9 Hz, 2H, OCH$_2$): 7.1 (m, 1H, arom): 7.4 (m, 1H, arom). $^{13}$C NMR (d$^6$-DMSO and CDCl$_3$) δ ppm: 27.88, 71.78, 110.51, 114.17, 131.02, 131.25, 159.09, 164.87. Anal., C$_9$H$_7$BrO$_3$ calcd. C, 44.44; H, 2.88; found C, 44.52; H, 2.97.

Synthesis of 5-bromo-(N, N'-diethylaminoethyl)-2,3-dihydrobenzofuran-7-carboxamide (H)

A round bottom flask was charged with bromocarboxylic acid (1.79 g, 7.36 mmol) and chloroform (50 ml). The slurry was stirred and thionyl chloride (2.0 ml) in chloroform (8 ml) was added to the slurry along with 2 drops of DMF. The mixture was refluxed for 90 min to give a clear solution. The volatiles were removed in vacuo to give yellow solid. This acid chloride was used without further purification for the condensation with amine. To another flask containing N,N-diethylethylenediamine (0.82 g, 6.99 mmol) and triethylamine (15 ml) and CHCl$_3$ (30 ml) was added a solution of the above acid chloride in CHCl$_3$ (15 ml). The mixture was stirred for 3 hours. The volatiles were removed, the residue was washed with water (50 ml) and the organics were dissolved in CHCl$_3$ (75 ml). The organic layer was separated, dried over anhyd. Na$_2$SO$_4$, and the volatiles removed again to give a light yellow color oil. The oil was purified by passage through a silica gel column and elution with CHCl$_3$/MeOH:90/10. The fractions containing the desired compound were pooled together, and the volatiles were removed to give the carboxamide (1.9 g, 80%). TLC silica gel Rf (0.7) CHCl$_3$/MeOH:90/10. The hydrochloride salt was made with an ethanolic solution of hydrogen chloride gas upon trituration with anhydrous ether. $^1$H NMR (CDCl$_3$) δ ppm: 0.96–1.00 (t, J=7 Hz, 6H, NCH$_2$CH$_3$): 2.46–2.53 (q, J=7 Hz, 4H, NCH$_2$CH$_3$): 2.55–2.59 (t, J=7 Hz, 4H NCH$_2$):3.17–3.22 (t, J=8 Hz, 2 H, CH$_2$): 3.40–3.44 (m, 2H, NCH$_2$): 4.63–4.69 (t, J=9 Hz, 2H, OCH$_2$): 7.30 (m 1H. arom): 7.961–7.968 (m, 1H, arom). Anal. C$_{15}$H$_{21}$BrN$_2$O$_2$.2HCl, Calcd. C,47.68; H,5.82; N,7.41; found C,47.38; H,5.80; N,7.35.

Synthesis of 5-tributyltin-(N,N'-diethylaminoethyl)-2,3-dihydrobenzofuran-7-carboxamide (J)

A round bottom flask was charged with 5-bromocarboxamide (1.0 g, 2.93 mmol), bis(tributyltin) (2.4 g, 4.1 mmol), palladium tetrakis (triphenylphosphine) (0.35 g, 0.29 mmol) and triethylamine (55 ml). The mixture was refluxed for 3 hours. The volatiles were removed in vacuo and the residue was dissolved in CHCl$_3$. This solution was loaded onto a silica gel column and eluted first with CHCl$_3$ (100 ml) and then with CHCl$_3$/MeOH:90/10 whereby a light brown band was collected. The volatiles were removed in vacuo to give an oil (1.3 g). The TLC showed a slightly impure compound. The oil was passed through a short silica gel column again and eluted with CHCl$_3$/MeOH:90/10 to give 0.9 g pure tin compound. TLC (silica gel) Rf=0.45 (CHCl$_3$/MeOH:90/10). $^1$H NMR (CDCl$_3$) δ ppm: 0.83–1.60 (m, 33, H, nBu$_3$ and NCH$_2$CH$_3$); 2.51–2.59 (q, J=7 Hz, 4H, NCH$_2$CH$_3$); 2.60–2.66 (t, 2H, CH$_2$); 3.18–3.23 (t, J=8 Hz, CH$_2$); 3.44–3.50 (q, J=6 Hz, 2H, CH$_2$); 4.64–4.70 (t, J=9 Hz, 2H, OCH$_2$); 7.32 (m, 1H, arom); 7.97 (m, 1H, arom). $^{13}$C(CDCl$_3$) (δ ppm): 9.67, 12.01, 13.60, 16.45, 26.97, 27.30, 27.82, 29.03, 37.58, 47.06, 51.72, 71.74, 115.87, 127.26, 132.65, 135.53, 136.76, 158.04, 164.92.

Synthesis of 5-iodo-(N,N-diethylamino-ethyl)-2,3-dihydrobenzofuran-7-carboxamide (K)

Tributyltincarboxamide (300 mg) and iodine (0.8 g) were stirred together in $CHCl_3$ at room temperature for 48 hours. The mixture was quenched with a saturated solution of sodium thiosulfate. The organic layer was separated, dried and the volatiles were removed in vacuo to give a colorless oil. The oil was passed through the silica gel column and eluted with $CHCl_3$/MeOH:95/5. The first few fractions contained tributyltin iodide and were discarded. The later fractions provided the desired iodo (0.2 g, 95%) compound. TLC silica gel Rf=0.3 ($CHCl_3$/MeOH:90/10). $^1$H NMR ($CDCl_3$): 1.34–1.39 (t, J=8 Hz, 6H, $NCH_2CH_3$); 3.14–3.33 (overlapping multiplet and triplet, 8H); 3.85–3.91 (q, J=6 Hz, 2H, $NCH_2$); 4.71–4.76 (t, J=9 Hz, 2H, $OCH_2$); 7.54 (m, 1H, arom); 8.02 (m, 1H, arom).

Synthesis of 5-bromo-1-(2-aminoethylpiperidinyl)-2,3-dihydrobenzofuran-7-carboxamide (L)

A round bottom flask was charged with bromocarboxylic acid (2.0 g, 8.23 mmol) and chloroform (50 ml). The slurry was stirred and thionyl chloride (4.0 ml) in chloroform (10 ml) was added to the slurry along with 2–3 drops of dimethylformamide. The mixture was refluxed for 60 min to give a clear solution. The volatiles were removed in vacuo to give a yellow solid. The acid chloride was used without further purification for the condensation with amine. To another flask containing 1-(2-aminoethyl)piperidene (1.1 g, 8.58 mmol), triethylamine (15 ml) and $CHCl_3$ (40 ml) was added a solution of the above acid chloride in $CHCl_3$ (20 ml). The mixture was stirred for 3 hours at room temperature. The volatiles were removed and the residue was taken up in $CHCl_3$ (100 ml) and washed with water (2×50 ml). The organic layer was separated, dried over anhyd $Na_2SO_4$, and the volatiles removed in vacuo to give a light yellow oil. The oil was purified by passage through a silica gel column when elution with $CHCl_3$/MeOH:90/10. The desired fractions were combined and the volatiles were evaporated to give light yellow oil (2.4 g, 83%). Rf (TLC silica gel $CHCl_3$/MeOH:90/10)=0.7. $^1$H NMR (δ ppm): 1.42–1.60 (m, 6H, piperidinyl $CH_2$'s); 2.42 (bs, 4H, piperidinyl $NCH_2$); 2.48–2.52 (t, J=6 Hz, 2H, $CH_2$); 3.20–3.26 (t, J=9 Hz, 2H, NCH2); 3.48–3.54 (m, 2H, $NHCH_2$); 4.68–4.73 (t, J=9 Hz, 2H, $OCH_2$); 7.33–7.35 (m, 1H, arom); 7.98–7.99 (m, 1H, arom); 8.05 (bt, 1H, NH).

Synthesis of 5-n-tributyltin-1-(2-aminoethylpiperidinyl)-2-3-dihydrobenzofuran-7-carboxamide (M)

5-bromo-carboxamide (2.0 g, 5.63 mmol), bis(tributyltin) (3.3 g, 5.7 mmol), and palladium tetrakis (triphenylphosphine) (0.33 g, 0.28 mmol) were refluxed overnight (15 hrs.) in triethylamine (100 ml). The black residue was separated from the solvent. The volatiles were removed and the yellow residue was passed through a silica gel column and eluted first with $CHCl_3$ (150 ml) and then with $CHCl_3$/MeOH:90/10. The fractions containing the desired compound were combined together and the volatiles were removed to give a light yellow viscous oil (1.4 g). $^1$H NMR (δ ppm): 0.82–0.87 (t, J=7 Hz, 9H, $nBu_3$); 0.98–1.59 (m, 25 H, $nBu_3$; and piperidinyl $CH_2$); 2.48 (bm, 4H, piperidinyl $NCH_2$); 2.49–2.54 (t, J=7 Hz, 2H, $CH_2$); 3.21–3.26 (t, J=9 Hz, 2H, $CH_2$); 3.51–3.55 (m, 2H, $NCH_2$); 4.63–4.69 (t, J=9 Hz, 2H, $OCH_2$); 7.34 (m, 1 H, arom); 7.95 (m, 1H, arom).

The reactions described hereinabove are depicted in Reaction Scheme II.

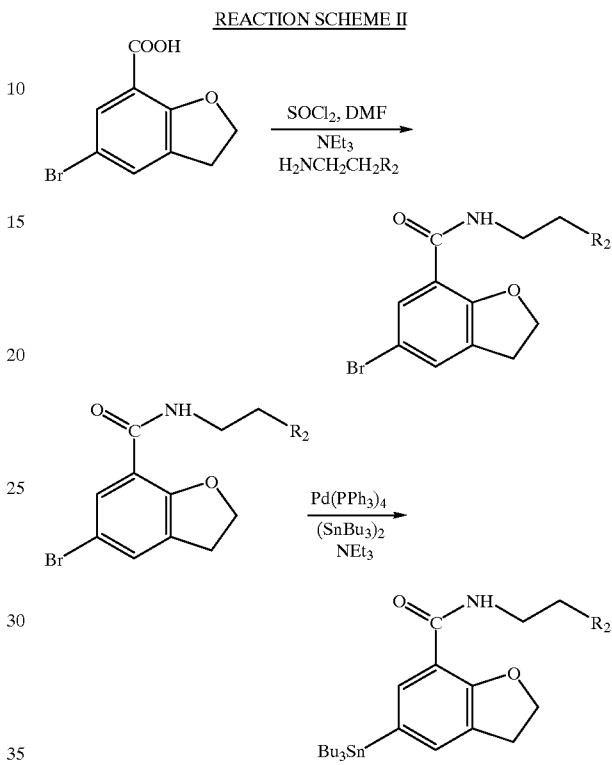

REACTION SCHEME II

EXAMPLE 3

Synthesis of $^{125}$I(N-Benzylpiperidin-4-yl)-4-iodobenzamide 4-[$^{125}$]BP (N)

Materials and Methods

Melting points were determined with a Fisher-Johns apparatus. $^1$H and $^{13}$C NMR spectra were recorded on Brucker 300 AM spectrometer. Unless noted, chemical shifts were expressed as ppm using $CDCl_3$ as an internal standard. All chemicals were obtained form the Aldrich chemical Company, Milwaukee, Wis. The thin layer chromatography (TLC) system consisted of Analtech uniplate silica gel GF plates (250 microns, 10×20 cm), using $CHCl_3$/MeOH:90/10 as solvent. Radioactive spots were scanned and recorded by a Packard 7220/21 radiochromatogram. Mass spectra (chemical ionization) were recorded on Finnigan 1015 mass spectrometer. $Na^{125}I$ was obtained from Amersham, Arlington Heights, Ill.

Preparation of (N-benzylpiperidin-4-yl)-4-iodobenzamide

A round bottom flask was charged with 4-iodobenzoic acid (3.0 g, 12.1 mmol) in chloroform (100 mL). To the solution was added thionyl chloride (5.0 mL) in chloroform (10 mL) and 2–3 drops of dimethylformamide (DMF). The slurry was heated at reflux for 2 hours, while monitoring the reaction through an oil bubbler. A clear solution of 4-iodobenzoyl chloride was obtained. The volatiles were removed and a colorless oil was obtained which solidified upon cooling.

The 4-iodobenzoyl chloride was dissolved in chloroform (40 mL) and added to a flask containing 4-amino-1-benzylpiperidine (2.29 g, 12.1 mmol) in chloroform (75 mL) and triethylamine (20 mL). The mixture was stirred at room temperature overnight and the volatiles were removed in vacuo. The resulting slurry was washed with water (100 mL). The organics were dissolved in $CHCl_3$ (100 mL), separated from the aqueous layer and dried over anhydrous $Na_2SO_4$. The solvent was removed to give a solid (yield, 86%), m.p. 206° C. m/e=420 (M$^+$). $^1$H R (δ ppm): 1.47–1.60 (m, 2H, $CH_2$); 1.97–2.11 (m, 2H, $CH_2$); 2.15–2.19 (m, 2H, $CH_2$); 2.81–2.85 (m, 2H, $CH_2$); 3.49 (s, 2H, benzyl $CH_2$); 3.91–3.97 (m, 1H, CH); 5.98–6.00 (d, 1H, NH); 7.22–7.30 (m, 5H arom); 7.43–7.45 (d, 2H, J=8 Hz, para substituted arom); 7.73–7.76 (d, 2 H, J=8 Hz, para substituted arom). $^{13}$C NMR (δ ppm): 32.23, 47.19, 52.25, 63.01, 127.14, 128.27, 128.49, 129.14, 134.18, 137.75, 138.14, 166.02)

Preparation of (N-benzylpiperidin-4-yl)-4-bromobenzamide (N-benzylpiperidin-4-yl)-4-bromobenzamide was prepared by a procedure like that described for N-benzylpiperidin-4-yl-4-iodobenzamide, but using 4-bromobenzoic acid as starting material.

Preparation of (N-benzylpiperidin-4-yl)-4-tri-n-butylstannylbenzamide

A flame dried flask was charged with (N-benzylpiperidin-4-yl)-4-bromobenzamide (1.0 g, 2.68 mmol) in triethylamine (100 mL). Tetrakis (triphenylphosphine) palladium (300 mg, 0.27 mmol), and bistributyltin (1.8 g, 3.10 mmol) were added, and the mixture was refluxed under nitrogen for 12 hours. The mixture was cooled and the volatiles were removed in vacuo. The resulting black oil was passed through a silica gel column with elution with $CHCl_3$ (75 mL), followed by elution with $CHCl_3$ MeOH: 95/5. The desired fractions, as characterized by thin layer chromatography, were pooled and solvent was evaporated to give an oil (57% yield). m/e=585 (M+1)$^+$ $^1$H NMR (δ ppm): 0.82–1.99 (m, 31H, typical $nBu_3$ and $CH_2$); 1.99–2.10 (m, 2H, $CH_2$); 2.24–2.31 (m, 2H, $NCH_2$); 2.92–2.97 (m, 2H, $NCH_2$); 3.61 (s, 2H benzylic $CH_2$); 4.01–4.10 (m, 1H, CH); 6.18–6.21 (d, 1H, NH); 7.24–7.67 (m, 9H, arom). $^{13}$C NMR (δ, ppm): 9.61, 27.27, 28.99, 31.58, 46.42, 52.16, 62.68, 125.84, 127.63, 128.40, 128.55, 129.52, 131.94, 131.21, 136.55, 167.19.

Radiochemical Synthesis of $^{125}$I(-N-benzylpiperidin-4-yl)-4-iodobenzamide

To 100 μL of a solution of (N-benzylpiperidin-4-yl)-4-tributyltinbenzamide (1 mg/ml) in ethanol was added a solution of Na$^{125}$I (0.5–1.0 mCi, 3–5 μL) in 0.1N NaOH, followed by the addition of 0.05N HCl (50–100 μL) to adjust the pH of the solution to pH 4.0–5.0. One hundred μL of a freshly prepared solution of N-chloro-4-toluenesulfonamide sodium monohydrate (chloramine-T) (1 mg/ml) was added to the above mixture. The contents were incubated for 15 minutes at room temperature and 200 μL of a solution of sodium metabisulfite (10 mg/ml) were added and incubated for 5 minutes. The reaction mixture was neutralized with a saturated solution of $NaHCO_3$ (500 μL). 0.4 mL of normal saline was added and the organics were extracted in $CHCl_3$ (1.0 mL) after vortexing 30 seconds. The chloroform layer was evaporated in a stream of air. The residue was dissolved in methanol (400 μL), and injected into a Gilson HPLC fitted with a Waters Z-module radial compression separation system containing a micro BondaPak C-18 reverse phase column equipped with Rheodyne 4125 injector (0.5 mL loop). The fractions containing the desired compounds were pooled together and co-spotted on TLC along with authentic "cold" 4-IBP and developed in $CHCl_3$/MeOH:90/10. The Rf of "cold" 4-IBP and 4-[$^{125}$I]BP was found to be 0.85 in the above solvent system.

The reactions described hereinabove are depicted in Reaction Scheme III:

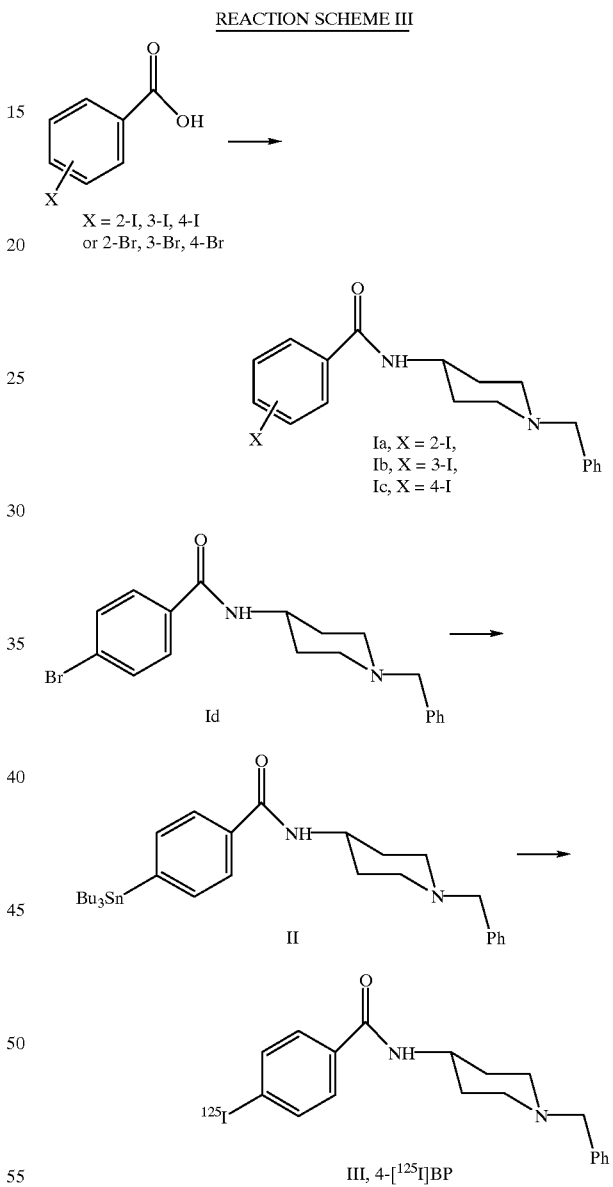

EXAMPLE 4

Preparation of $^{125}$I-(N-Benzylpiperidin-4-yl)-3-iodobenzamide $^{125}$I-(N-Benzylpiperidin-4-yl)-3-iodobenzamide, 3-[$^{125}$I] BP, was prepared by a procedure like that described above in Example 3, but using 3-iodobenzoic acid as starting material.

Unradiolabeled 3-IBP was prepared in 91% yield, m.p. 151–152° C. m/e=420 (M$^+$). $^1$H NMR (δ ppm): 1.58–1.62

(m, 2H, CH$_2$); 1.97–2.01 (m, 2H, CH$_2$); 2.14–2.22 (m, 2H, NCH$_2$); 2.85–2.89 (m, 2H, NCH$_2$); 3.53 (s, 2H, benzylic CH$_2$); 3.90–3.96 (m, 1H, CH); 5.98–6.01 (d, 1H, NH); 7.11–7.16 (m, 1H, arom); 7.24–7.32 (m, 5H, arom); 7.65–8.05 (m, 3H, arom). $^{13}$C NMR ($\delta$ ppm): 32.04, 47.16, 52.20, 62.89, 126.06, 127.28, 128.32, 129.23, 130.22, 135.94, 136.78, 137.67, 140.28, 165.28.

EXAMPLE 5

Preparation of $^{125}$I-(N-benzylpiperidin-4-yl)-2-iodobenzamide $^{125}$I-(N-benzylpiperidin-4-yl)-2-iodobenzamide, 2-[$^{125}$I]BP, was prepared by a procedure like that described above in Example 3, but using 2-iodobenzoic acid as starting material.

Unradiolabeled 2-IBP was prepared in 90% yield, m.p. 145–146° C. m/e=420 (M$^+$). $^1$H NMR ($\delta$ ppm): 1.53–1.57 (m, 2H, CH$_2$); 1.99–21.0 (m, 2H, CH$_2$); 2.14–2.17 (m, 2H, NCH$_2$); 2.82–2.85 (m, 2H, NCH$_2$); 3.50 (s, 2H, benzylic CH$_2$); 3.91–3.97 (m, 1H, CH); 6.02–6.10 (d, 1H, NH); 7.11–7.15 (m, 1H, arom); 7.23–7.29 (m, 5H, arom); 7.65–7.79 (m, 2H, arom); 8.04 (m, 1H, arom). $^{13}$C ($\delta$, ppm): 32.13, 47.26, 52.20, 62.93, 126.04, 127.06, 128.20, 129.07, 130.15, 135.89, 136.76, 138.13, 140.18, 163.26.

EXAMPLE 6

In Vitro Competitive Binding of Radioactive and Nonradioactive (2-PiperidinylAminoethyl)-4-IodoBenzamide Competitive binding studies indicate that compounds of the present invention bind malignant melanoma cells with very high affinity.

Materials and Methods

A2058 cells, derived from a brain metastasis of human malignant melanoma (Todaro et al. 1980 Proc. Natl. Acad. Sci. USA 77:5258) were obtained from the National Institutes of Health. These cells were grown in DMEM2 medium (Dulbecco's modification of Eagle's medium, EMEM) supplemented with 10% fetal bovine serum and 0.03% L-glutamine.

(2-Piperidinylaminoethyl)4-iodobenzamide (i.e. IPAB, B) and $^{125}$L(2-piperidinylaminoethyl)4-iodobenzamide (D) was synthesized as described in Example 1.

In Vitro Cell Binding Assay

A2058 cells, grown as described above, were harvested with calcium and magnesium free phosphate buffer (0.1M) containing 0.02% EDTA. Cells were washed twice with ice-cold RPMI 1640 medium (Gibco) without glutamine and resuspended in the same medium. Carrier-free [$^{125}$I]PAB (0.1 ml) was added to eight aliquots of 0.1 ml test A2058 cells (1.5×10$^6$ cells in suspension). To observe competitive binding by non-radioactive IPAB, varying concentrations of non-radioactive IPAB were added in a volume of 0.1 ml. Cells were incubated at 37° C. for 5 hr. after addition of radioactive and nonradioactive IPAB.

After incubation, cells were collected by centrifugation for 5 min and washed twice with RPMI 1640 medium. The radioactivity bound to cells was counted using a Packard Autogamma 5650 scintillation counter.

Data were analyzed with an INPLOT® iterative, non-linear least square curve fitting program.

Results

FIG. 1 illustrates that IPAB binds to human malignant melanoma cells with high affinity. In particular, FIG. 1 shows the amount of nonradioactive IPAB needed to competitively inhibit binding of radioactive IPAB. Binding of 50% of the radioactive IPAB was competitively inhibited by as little as 6.8 nM (i.e. Ki is 6.8 nM). These data indicate that IPAB binding is so highly selective and stable that the interaction of IPAB with human malignant melanoma cells likely occurs by IPAB binding to a specific cell receptor.

EXAMPLE 7

In Vitro Binding Competition Between Pharmacological Antagonists and (2-PiperidinylAminoethyl)-4-IodoBenzamide Competitive binding studies indicate that compounds of the present invention bind cell surface sigma receptors on malignant melanoma cells.

Materials and Methods

A2058 cells, derived from a brain metastasis of human malignant melanoma (Todaro et al. 1980 Proc. Natl. Acad. Sci. USA 77:5258) are obtained from the National Institutes of Health. These cells are grown in DMEM2 medium (Dulbecco's modification of Eagle's medium, EMEM) supplemented with 10% fetal bovine serum and 0.03% L-glutamine.

(2-Piperidinylaminoethyl)4-iodobenzamide (i.e. IPAB, B) and $^{125}$I(2-piperidinylaminoethyl)4-iodobenzamide (D) is synthesized as described in Example 1.

Pharmacological antagonists and the corresponding receptors which are tested include SE2466-2 (i.e. sigma receptor antagonist), fluphenazine (sigma-1 at low concentrations and sigma-2 at high concentrations), SCH23390 (dopamine-1), raclopride (dopamine-2), melanocyte secreting hormone peptide (melanocyte secreting hormone receptor), mianserin (5-hydroxytryptamine-1 receptor), NAN-190 (5-hydroxy-tryptamine-1a receptor), ketanserine (5-hydroxytryptamine-1c receptor), ketanserine and mianserin (5-hydroxytryptamine-2 receptor) and 3-tropanyldichloroben (5-hydroxytryptamine-3 receptor).

In Vitro Cell Binding Assay

A2058 cells, grown as described above, are harvested with calcium and magnesium free phosphate buffer (0.1M) containing 0.02% EDTA. Cells are washed twice with ice-cold RPMI 1640 medium (Gibco) without glutamine and resuspended in the same medium. Carrier-free [$^{125}$I]PAB (0.1 ml) is added to eight aliquots of 0.1 ml test A2058 cells (1.5×10$^6$ cells in suspension). To observe competitive binding by pharmacological antagonists, varying concentrations of the antagonists are then added in a volume of 0.1 ml. Cells are incubated at 37° C. for 5 hr. after addition of an antagonist and the radioactive IPAB.

After incubation, cells are collected by centrifugation for 5 min and washed twice with RPMI 1640 medium. The radioactivity bound to cells is counted using a Packard Autogamma 5650 scintillation counter.

Data can be analyzed with an INPLOT® iterative, non-linear least square curve fitting program.

Results

Antagonists with demonstrated binding specificity for cell surface sigma receptors (e.g. fluphenazine) can act as competitive binding inhibitors of IPAB binding to malignant melanoma cells. In contrast, antagonists that do not bind to cell surface sigma receptors cannot inhibit binding of radioactive IPAB to melanoma cells. Such data indicate that the present compounds bind to cell surface sigma receptors.

EXAMPLE 8

Binding Competition Between Pharmacological Antagonist and (2-PiperidinylAminoethyl)-4-IodoBenzamide Materials and Methods (2-Piperidinylaminoethyl)4-iodobenzamide (i.e. IPAB, B) was synthesized as described in Example 1.

A sigma-1 binding assay was performed in guinea pig brain membranes and rat C6 glioma cells (purchased from American Tissue and Cell Collection, Rockville, Md.) in the presence of a sigma-1 selective ligand, $[_3H]-(+)$-pentazocine.

A sigma-2 binding assay was performed in rat liver membranes in the presence of a sigma-2 selective ligand, $[^3H]DTG$, in the presence of dextrallorphan to mask sigma-1 sites.

Membrane Preparation

A plasma membrane-mitochondrial (P2) membrane fraction was prepared from frozen guinea pig brains (Pel-Freeze, Rogers, Ak.), minus cerebellum. The brain tissue was thawed slowly before homogenization. A crude P2 membrane fraction was also prepared from the livers of rat Sprague-Dawley rats (150–220 g, Taconic Farms) liver. The animals were decapitated and their livers were minced and homogenized. The tissue homogenization was carried out at 4° C. in ml/g tissue weight of 10 mM Tris-HCl/0.32M sucrose, pH=7.4 using 10 motor-driven strokes in a Potter-Elvehjem Teflon glass homogenizer. The crude homogenate was centrifuged for 10 min at 100 g and the crude nuclear (P1) pellet was discarded. Supernatants were centrifuged at 31000 g for 15 min to yield a plasma membrane-mitochondrial pellet (P2). This pellet was resuspended in 3 ml/g in 10 mM tris-HCl, pH 7.4 and used for binding studies. Protein concentrations were determined by the method of Lowry.

Various concentrations of the IPAB ranging from 0.5–1000 nM were incubated with guinea pig brain membranes (300–500 microgram protein) in the presence of 3 nm $[^3H]-(+)$-pentazocine (specific activity 52 Ci/mmol) in 0.5 ml of 50 mM Tris-HCl for 60 min at 37° C. The amount of non-specific binding was determined by the addition of 10 mM Tris-HCl, pH 8.0 followed by rapid filtration through glass filters using a Brandel Cell harvester (Gaithersburg, Md.). Filters were washed twice with ice-cold buffer. Prior to use, filters were soaked in 0.5% polyethyleneimine for about 30 min at 25° C. Similarly rats liver membranes (sigma-2) or C6 glioma cell homogenates were incubated with 3 nM $[^3H]DTG$ (39.4 Ci/mmol) in the presence of 1 micromolar cold dextrallorphan and various concentration of the unlabeled IPAB. The amount of non-specific binding was determined by incubation of membranes in the presence of 5 micromolar haloperidol.

When the assay was terminated, the membranes were filtered and the filtrate washed twice as above. The radioactivity was counted in Ecoscint (National Diagnostics, Manville, N.J.) after an overnight extraction of counts.

The amount of IPAB required to inhibit binding of sigma-1 and sigma-2 selective ligands by 50% (i.e. the $IC_{50}$ values) was derived using the computerized iterative curve-fitting program, GraphPAD. $K_i$ values were calculated from the $IC_{50}$ values using Cheng-Prusoff equation.

Results
The $K_i$ values for IPAB are shown in Table 1.

| Sigma-1 Guinea Pig Brain | Sigma-2 Rat Liver | Sigma-2 $C_6$ Glioma Cells |
|---|---|---|
| 0.89 nM | 24.0 nM | 130 nM |

These data demonstrate that IPAB binds to cell surface sigma receptors with very high affinity.

EXAMPLE 9

Inhibition Constants (Ki=nM) For Binding Affinities of IBP Isomers in Various Receptor Systems Materials and Methods (N-Benzylpiperidin-4-yl)-2-iodobenzamide (i.e. 2-IBP) was synthesized as described in Example 5. 4-IBP and 3-IBP were synthesized as described in Examples 3 and 4 respectively.

The sigma-1 binding assay was performed in guinea pig brain membranes in the presence of a sigma-1 selective ligand, $[^3H]-(+)$-pentazocine purchased from DuPont NEN, Boston Mass.

The sigma-2 binding assay was performed in rat liver membranes in the presence of a sigma-2 selective ligand, $[^3H]DTG$, in the presence of dextrallorphan to mask sigma-1 sites. $[^3H]DTG$ was purchased from DuPont NEN, Boston Mass.

A similar procedure was used with each IBP compound but will be shown using the 2-IBP compound.

Membrane Preparation

A plasma membrane-mitochondrial (P2) membrane fraction was prepared from frozen guinea pig brains (Pel-Freeze, Rogers, Ak.), minus cerebellum. The brain tissue was thawed slowly before homogenization. A crude P2 membrane fraction was also prepared from the livers of Sprague-Dawley rats (150–220 g, Taconic Farms). The animals were decapitated and their livers were minced and homogenized. The tissue homogenization was carried out at 4° C. in 10 mM tris-HCl/0.32M sucrose, pH=7.4 using 10 motor-driven strokes in a Potter-Elvehjem Teflon glass homogenizer. The crude homogenate was centrifuged for 10 min at 1000 g and the crude nuclear (P1) pellet was discarded. Supernatants were centrifuged at 31000×g for 15 min to yield a plasma membrane-mitochondrial pellet (P2). This pellet was resuspended in 3 ml/g in 10 mM tris-HCl, pH 7.4 and used for binding studies. Protein concentrations were determined by the method of Lowry.

Various concentrations of 2-IBP ranging from $10^{-4}$ to $10^{-12}$M were incubated with guinea pig brain membranes (300–500 microgram protein) in the presence of 3 nM $[^3H]-(+)$-pentazocine (specific activity 51.7 Ci/mmol) in 0.5 ml of 50 mM tris-HCl for 120 min at 25° C. The amount of non-specific binding was determined by the addition of 10 mM tris-HCl, pH 8.0 followed by rapid filtration through glass filters using a Brandel Cell harvester (Gaithersburg, Md.). Filters were washed twice with ice-cold 10 mM tris-HCL. Prior to use, filters were soaked in 0.5% polyethyleneimine for about 30 min at 25° C.

Similarly rats liver membranes (sigma-2) were incubated with 3 nM [$^3$H]DTG (39.4 Ci/mmol) in the presence of 1 μM cold dextrallorphan and various concentration of the unlabeled IBP. The amount of non-specific binding was determined by incubation of membranes in the presence of 10 micromolar haloperidol.

When the assay was terminated, the membranes were filtered and the filtrate washed twice as above. The radioactivity was counted in Ecoscint (National Diagnostics, Manville, N.J.) after an overnight extraction of counts.

The amount of IBP required to inhibit binding of sigma-1 and sigma-2 selective ligands by 50% (i.e. the $IC_{50}$ values) was derived using the computerized iterative curve-fitting program, GraphPAD. $K_i$ values were calculated from the $IC_{50}$ values using Cheng-Prusoff equation.

Results

The $K_i$ values for IBP compounds are shown in Table 2:

| COMPD | SIGMA-1 GUINEA PIG BRAIN [$^3$H]-(+)-PENT | SIGMA-2 RAT LIVER [$^3$H]DTG + DEX |
|---|---|---|
| 4-IBP | 1.70 ± 0.44 | 25.2 ± 1.28 |
| 3-IBP | 3.02 ± 1.06 | 84.6 ± 2.5 |
| 2-IBP | 1.64 ± 0.15 | 29.6 ± 0.49 |

| COMPD | DOPAMINE D-2 RAT BRAIN [$^3$H]-(-)-SULPIRIDE | PCP RAT BRAIN [$^3$H]TCP | MUSC RAT BRAIN [$^3$H]QNB |
|---|---|---|---|
| 4-IBP | 382 ± 39 | >100 000 | >100 000 |
| 3-IBP | 24.8 ± 0.02 | >100 000 | >100 000 |
| 2-IBP | 63.4 ± 10.8 | >100 000 | >100 000 |

These data demonstrate that all three IBP compounds bind sigma-1 sites on guinea pig brains with high affinity. The 2- and 4-IBP compounds also had moderate affinity for rat liver sigma-2 sites. The affinity of 3-IBP for sigma-2 sites was relatively low.

The data in Table 2 show low affinity for dopamine, phenylcyclidine, PCP, and muscarinic receptors.

EXAMPLE 10

Biodistribution of $^{125}$I-(2-PiperidinylAminoethyl)-4-IodoBenzamide

Biodistribution experiments were performed to assess the tumor-specificity of the present compounds.

Materials and Methods

A2058 tumor cells, derived from a brain metastasis of human malignant melanoma (Todaro et al. 1980 Proc. Natl. Acad. Sci. USA 77:5258) were obtained from the National Institutes of Health.

Non-small cell lung carcinoma cell lines NCI-157, NCI-838 and NCI-1299 were obtained from the National Cancer Institute. The NCI-157 cell line is a squamous carcinoma cell line, while NCI-838 is an adenocarcinoma cell line and NCI-1299 is a large cell lung carcinoma cell.

Tumor cells were grown in DMEM2 medium (Dulbecco's modification of Eagle's medium, EMEM) supplemented with 10% fetal bovine serum and 0.03% L-glutamine.

$^{125}$I-N-(diethylaminoethyl)4-iodobenzamide (i.e.[$^{125}$I]DAB) was prepared as described in John et al. (1993 Nucl. Med. Biol. 20: 75–79).

$^{125}$I(2-piperidinylaminoethyl)4-iodobenzamide (i.e. [$^{125}$I]PAB) (D) was synthesized as described in Example 1.

Animal Biodistribution Assays

For in vivo studies, tumor cells were harvested using calcium and magnesium free PBS containing 0.02% EDTA. Suspension of 5×10$^6$ cells (viability greater than 95%) in 0.2 mL of medium were inoculated subcutaneously in female Balb/c nu/nu mice. After about two weeks, solid tumors of about 1 cm in diameter appeared in approximately 85% of all inoculated mice. Mice with solid tumors having a diameter of about 1 cm were used for biodistribution studies.

Balb/c nu/nu mice (17–22 g) were injected intravenously with 0.2 ml of a saline solution containing [$^{125}$I]PAB (5–6 pCi). At 1, 6 and 24 hr. after injection, blood samples were collected by cardiac puncture and the mice were sacrificed immediately thereafter by cardiectomy while under halothane anesthesia. The organs of interest were subsequently excised, blotted with tissue paper, weighed, and the radioactivity was counted using a Packard automatic counter (autogamma 5650). The % injected dose/g (% ID/g) values were determined by comparison of tissue radioactivities with suitably diluted aliquots of the injected [$^{125}$I]PAB dose divided by the weight of the organ. The values obtained were normalized to a mouse weighing 20 g. The differences between [$^{125}$I]PAB and [$^{125}$I]DAB were examined by Student's unpaired t tests.

Results

Tables 1–3 illustrate the biodistribution of [$^{125}$I]PAB and [$^{125}$I]DAB in nude mice bearing human A2-058 melanoma xenografts in the flank at one, six, and twenty-four hours, respectively, after administration of the imaging agent.

At one hr. post-injection (Table 1), the concentration of [$^{125}$I]DAB (% injected dose/gm) was higher than the tumor concentration of [$^{125}$I]PAB in several tissues including non-tumorous liver, muscle, lung and heart tissues. Therefore, while [$^{125}$I]DAB collected in the tumor at a marginally higher level than [$^{125}$I]PAB, [$^{125}$I]DAB was significantly less specific for the tumor site than [$^{125}$I]PAB.

By 6 hrs. after administering the diagnostic agents, mice receiving [$^{125}$I]PAB had more of this diagnostic agent in the tumor than any other tissue. In contrast [$^{125}$I]DAB was found at higher concentrations in the liver than in the tumor. Moreover, the concentration of [$^{125}$I]DAB was significantly higher than that of [$^{125}$I]PAB is non-cancerous blood, liver and intestinal tissues.

By 24 hrs. mice receiving [$^{125}$I]PAB had about four-fold more [$^{125}$I]PAB in their tumors than in their livers. In contrast mice receiving [$^{125}$I]DAB had only about half as much [$^{125}$I]DAB in their tumors as their livers. These data indicate that high levels of [$^{125}$I]DAB are non-specifically localized in the liver. These data also indicate that [$^{125}$I]DAB has less tumor specificity than [$^{125}$I]PAB.

Moreover, the tumor concentration of [$^{125}$I]PAB was almost twice as high as that of [$^{125}$I]DAB indicating that IPAB binds to tumor cells with greater affinity and stability than IDAB. These data indicate that [$^{125}$I]PAB is highly specific for malignant tumors which contain cells having sigma receptors.

TABLE 1

Biodistribution of N-(piperidinylaminoethyl)-
4-iodo [$^{125}$I]benzamide, [$^{125}$I]PAB, and
N-(diethylaminoethyl)4-iodo [$^{125}$I]benzamide,
[$^{125}$I]DAB, in nude mice xenografted with human
melanotic melanoma [% ID/g; mean (std. dev.), n = 6]

| 1 Hour | [$^{125}$I]PAB | [$^{125}$I]DAB | P Value for Difference |
|---|---|---|---|
| Blood | 0.967(.168) | 1.03(.318) | NS |
| Liver | 6.36(.770) | 12.7(1.69) | <.001 |
| Spleen | 3.11(.789) | 3.46(.206) | NS |
| Kidney | 3.82(.561) | 4.63(.905) | NS |
| Bone | 0.750(.0663) | 1.04(.476) | NS |
| Muscle | 0.552(.0711) | 0.988(.125) | <.001 |
| Stomach | 3.23(.697) | 3.84(1.98) | NS |
| Intestine | 10.64(.541) | 5.04(1.47) | <.001 |
| Thyroid | 4.23(.594) | 5.68(1.02) | .013 |
| Lung | 2.34(.277) | 6.32(1.55) | <.001 |
| Heart | 1.14(.207) | 1.67(.210) | .001 |
| Brain | 0.895(.0887) | 1.04(.0855) | .015 |
| Tumor | 3.87(.470) | 5.18(1.31) | .044 |
| RATIO | | | |
| Tumor/Blood | 4.16(1.09) | 5.68(2.75) | |
| Tumor/Muscle | 7.16(1.50) | 5.33(1.65) | |

TABLE 2

Biodistribution of N-(piperidinylaminoethyl)-
4-iodo [$^{125}$I]benzamide, [$^{125}$I]PAB, and
N-(diethylaminoethyl)4-iodo [$^{125}$I]benzamide,
[$^{125}$I]DAB, in nude mice xenografted with human
melanotic melanoma [% ID/g; mean (std. dev.), n = 6]

| 6 hour | [$^{125}$I]PAB | [$^{125}$I]DAB | P Value for Difference |
|---|---|---|---|
| Blood | 0.208(.0542) | 1.03(.0.197) | .001 |
| Liver | 1.16(.212) | 3.74(.427) | <.001 |
| Spleen | 0.330(.105) | 0.260(.0990) | NS |
| Kidney | 0.483(.131) | 0.435(.0909) | NS |
| Bone | 0.115(.0236) | 0.100(.0297) | NS |
| Muscle | 0.0983(.0306) | 0.0967(.0356) | NS |
| Stomach | 0.757(.298) | 0.475(.164) | NS |
| Intestine | 2.46(1.18) | 0.423(.0963) | .002 |
| Thyroid | 0.583(.203) | 0.400(.124) | NS |
| Lung | 0.387(.0568) | 0.458(.0993) | NS |
| Heart | 0.167(.0372) | 0.150(.0329) | NS |
| Brain | 0.1.22(.0331) | 0.132(.0204) | NS |
| Tumor | 2.91(.463) | 2.83(.388) | NS |
| RATIO | | | |
| Tumor/Blood | 14.9(5.07) | 28.1(5.84) | .002 |
| Tumor/Muscle | 32.5(12.0) | 33.3(14.0) | NS |

TABLE 3

Biodistribution of N-(piperidinylaminoethyl)-
4-iodo [$^{125}$I]benzamide, [$^{125}$I]PAB, and
N-(diethylaminoethyl)4-iodo [$^{125}$I]benzamide,
[$^{125}$I]DAB, in nude mice xenografted with human
melanotic melanoma [% ID/g; mean (std. dev.), n = 6]

| 24 Hour | [$^{125}$I]PAB | [$^{125}$I]DAB | P Value for Difference |
|---|---|---|---|
| Blood | 0.0617(.018) | 0.0350(.0084) | .009 |
| Liver | 0.263(.0216) | 1.12(.232) | <.001 |
| Spleen | 0.0383(.015) | 0.0350(.023) | NS |
| Kidney | 0.0850(.016) | 0.065(.0197) | NS |
| Bone | 0.0133(.0052) | 0.0133(.0052) | NS |
| Muscle | 0.0117(.0041) | 0.0150(.0084) | NS |
| Stomach | 0.130(0.881) | 0.445(.386) | NS |
| Intestine | 0.132(.0852) | 0.123(.0717) | .NS |
| Thyroid | 0.100(.143) | 0.0550(.0207) | NS |
| Lung | 0.0717(.0075) | 0.0633(.0273) | NS |
| Heart | 0.0283(.0075) | 0.0233(.0175) | NS |
| Brain | 0.0067(.0052) | 0.0033(.0052) | NS |
| Tumor | 1.028(.239) | 0.553(.241) | .006 |
| RATIO | | | |
| Tumor/Blood | 17.8(6.10) | 15.5(4.69) | NS |
| Tumor/Muscle | 94.5(32.5) | 39.7(9.61) | .003 |

EXAMPLE 11

Biodistribution of $^{125}$I-(2-PiperidinylAminoethyl)-4-IodoBenzamide

Biodistribution experiments were performed to assess the tumor-specificity of the present compounds.

Materials and Methods

Non-small cell lung carcinoma cell lines NCI-157, NCI-838 and NCI-1299 were obtained from the National Cancer Institute. The NCI-157 cell line is a squamous carcinoma cell line, while NCI-838 is an adenocarcinoma cell line and NCI-1299 is a large cell lung carcinoma cell.

Tumor cells were grown in DMEM2 medium (Dulbecco's modification of Eagle's medium, EMEM) supplemented with 10% fetal bovine serum and 0.03% L-glutamine.

[$^{125}$I]-N-(diethylaminoethyl)4-iodobenzamide (i.e. [$^{125}$I] DAB) was prepared as described in John et al. (1993 Nucl. Med. Biol. 20: 75–79).

$^{125}$I(2-piperidinylaminoethyl)4-iodobenzamide (i.e. [$^{125}$I] PAB) (D) was synthesized as described in Example 1.

Animal Biodistribution Assays

For in vivo studies, tumor cells were harvested using calcium and magnesium free PBS containing 0,02% EDTA. Suspension of 5×10$^6$ cells (viability greater than 95%) in 0.2 mL of medium were inoculated subcutaneously in female Balb/c nu/nu mice. After about two weeks, solid tumors of about 1 cm in diameter appeared in approximately 85% of all inoculated mice. Mice with solid tumors having a diameter of about 1 cm were used for biodistribution studies.

Balb/c nu/nu mice (17–22 g) were injected intravenously with 0.2 ml of a saline solution containing [$^{125}$I]PAB (5–6 µCi). At 1, 6 and 24 hr. after injection, blood samples were collected by cardiac puncture and the mice were sacrificed immediately thereafter by cardiectomy while under halothane anesthesia. The organs of interest were subsequently excised, blotted with tissue paper, weighed, and the radioactivity was counted using a Packard automatic counter (autogamma 5650). The % injected dose/g (% ID/g) values were determined by comparison of tissue radioactivities with suitably diluted aliquots of the injected [$^{125}$I]PAB dose divided by the weight of the organ. The values obtained were normalized to a mouse weighing 20 g.

Results

Tables 4–5 illustrate the biodistribution of [$^{125}$I]DAB and [$^{125}$I]PAB, respectively, in nude mice bearing human squamous cell carcinoma xenografts in the flank at one, six, and twenty-four hours after administration of the imaging agent.

By 24 hrs. mice receiving [$^{125}$I]PAB had more [$^{125}$I]PAB in their tumors than any other tissue. In contrast mice receiving [$^{125}$I]DAB had about six-fold more [$^{125}$I]DAB in their livers as their tumors. These data indicate that high levels of [$^{125}$I]DAB are non-specifically localized in the liver. These data also indicate that [$^{125}$I]DAB has less tumor specificity than [$^{125}$I]PAB.

Moreover, the tumor concentration of [$^{125}$I]PAB was more than three-fold higher than that of [$^{125}$I]DAB at 24 hrs. post-injection indicating that IPAB binds to tumor cells with greater affinity and stability than IDAB. These data indicate that [$^{125}$I]PAB is highly specific for lung carcinomas which contain cells having sigma receptors.

TABLE 4

Biodistribution of N-(diethylaminoethyl)-
4-iodo [$^{125}$I]benzamide, [$^{125}$I]DAB, in nude mice
xenografted with human squamous cell carcinoma
[% ID/g; mean (std. dev.), n = 6]

| Tissue | 1 hr. | 6 hr. | 24 hr. |
| --- | --- | --- | --- |
| Blood | 1.35(0.42) | 0.301(0.04) | 0.027(0.00) |
| Liver | 13.77(0.72) | 5.84(0.51) | 1.25(0.10) |
| Spleen | 3.58(0.28) | 0.51(0.08) | 0.01(0.00) |
| Kidney | 7.64(0.35) | 1.07(0.16) | 0.05(0.00) |
| Bone | 1.85(0.22) | 0.21(0.01) | — |
| Stomach | 5.41(0.53) | 2.7(0.98) | 0.15(0.02) |
| Intestine | 5.64(0.58) | 1.34(0.27) | 0.05(0.01) |
| Thyroid | 8.22(0.72) | 1.48(0.55) | 0.03(0.01) |
| Lung | 6.38(0.89) | 1.07(0.14) | 0.03(0.09) |
| Heart | 2.21(0.16) | 0.38(0.11) | 0.00(0.09) |
| Brain | 1.57(0.05) | 0.23(0.05) | 0.00(0.00) |
| Tumor | 5.13(0.74) | 2.17(0.09) | 0.18(0.02) |

TABLE 5

Biodistribution of (piperidinylaminoethyl)-
4-iodo [$^{125}$I]benzamide, [$^{125}$I]PAB, in nude mice
xenografted with human squamous cell carcinoma
[% ID/g; mean (std. dev.), n = 6]

| Tissue | 1 hr. | 6 hr. | 24 hr. |
| --- | --- | --- | --- |
| Blood | 1.99(0.35) | 0.51(0.03) | 0.15(0.07) |
| Liver | 10.48(1.26) | 3.47(0.23) | 0.39(0.02) |
| Spleen | 3.97(0.18) | 0.86(0.20) | 0.05(0.00) |
| Kidney | 6.56(0.04) | 1.61(0.28) | 0.13(0.00) |
| Bone | 2.03(0.28) | 0.56(0.18) | 0.02(0.00) |
| Stomach | 6.57(1.31) | 3.46(0.18) | 0.20(0.03) |
| Intestine | 12.63(0.43) | 11.41(0.52) | 0.38(0.09) |
| Thyroid | 7.84(0.91) | 2.80(0.49) | 0.09(0.01) |
| Lung | 4.91(0.25) | 1.10(0.03) | 0.08(0.00) |
| Heart | 2.25(0.07) | 0.49(0.03) | 0.03(0.00) |
| Brain | 1.80(0.17) | 0.29(0.01) | 0.01(0.00) |
| Tumor | 4.27(0.40) | 3.27(0.33) | 0.66(0.12) |

EXAMPLE 12

Biodistribution of $^{125}$I-(N-Benzylpiperidin-4-yl)-4-IodoBenzamide

Biodistribution experiments were performed to assess the clearance of $^{125}$I-(N-benzylpiperidin-4-yl)-4-IodoBenzamide, 4-[$^{125}$I]BP.

Materials and Methods $^{125}$I-(N-Benzylpiperidin-4-yl)-4-iodobenzamide, 4-[$^{125}$I] BP, was prepared as described in Example 3.

For in vivo studies, Wistar rats were used.

Animal Biodistribution Assays

Male Wistar rats (200–230 g), while under anesthesia, were injected intravenously with 0.1 ml of a saline solution containing 20% ethanol solution of 4-[$^{125}$I]BP(4–5 pCi). At 1, 4, 6 and 24 hr. after injection, blood samples were collected by cardiac puncture and the mice were sacrificed immediately thereafter by cardiectomy while under anesthesia. The organs of interest were subsequently excised, blotted with tissue paper, weighed, and the radioactivity was counted using a Packard automatic counter (autogamma 5650). The % injected dose/g (% ID/g) values were determined by comparison of tissue radioactivities with suitably diluted aliquots of the injected 4-[$^{125}$I]BP dose divided by the weight of the organ.

A similar procedure was performed with 2-[$^{125}$I]BP and 3-[$^{125}$I]BP but blood samples were only collected at 1, 6 and 24 hours.

Results

Table 6 illustrates the biodistribution of 4-[$^{125}$I]BP in Wistar male rats at one, four, six and twenty-four hours after administration of the radiolabeled compound.

The results in Table 6 show that 4-[$^{125}$I]BP cleared quickly form the blood pool. After 24 hours, thyroid activity was minimal indicating that there is no in vivo dehalogenation. The results show that the compound crossed the blood brain barrier and is retained in the brain after 24 hours.

There is high uptake of 4-[$^{125}$I]BP in the liver, lungs and kidneys. These data indicate that 4-[$^{125}$I]BP is highly selective for organs containing cells that have sigma receptors.

The results for 3-[$^{125}$I]BP are shown in Table 8. These data show fast clearance from the blood, 0.75%ID/organ at one hour, but a high level in the liver.

The results for 2-[$^{125}$I]BP are shown in Table 7. These data show fast clearance from the blood and normal organs.

The results for 3-[$^{125}$I]BP are shown in Table 8. These data show fast clearance from the blood, 0.75%ID/organ at one hour, but a high level in the liver.

TABLE 6

4-[$^{125}$I]-(N-Benzylpiperidin-4-yl)-4-iodobenzamide, 4-[$^{125}$I]BP in Wistar Male Rats
(% ID/g; each data point represent average of four rats)

| Tissue | 1 hr. | 4 hr. | 6 hr. | 24 hr. |
| --- | --- | --- | --- | --- |
| Blood | 0.04 ± 0.00 | 0.02 ± 0.00 | 0.04 ± 0.00 | 0.02 ± 0.00 |
| Heart | 0.75 ± 0.05 | 0.74 ± 0.04 | 0.75 ± 0.02 | 0.65 ± 0.03 |
| Lung | 5.05 ± 0.26 | 5.22 ± 0.78 | 4.85 ± 0.17 | 3.70 ± 0.38 |
| Liver | 4.77 ± 0.13 | 7.76 ± 0.36 | 7.20 ± 0.40 | 5.37 ± 0.53 |
| Spleen | 1.60 ± 0.10 | 1.51 ± 0.19 | 1.57 ± 0.12 | 1.47 ± 0.28 |
| Kidney | 2.10 ± 0.15 | 2.05 ± 0.02 | 2.10 ± 0.08 | 1.54 ± 0.05 |
| Gonads | 0.39 ± 0.03 | 0.30 ± 0.02 | 0.34 ± 0.01 | 0.34 ± 0.01 |
| Muscle | 0.24 ± 0.02 | 0.20 ± 0.02 | 0.12 ± 0.02 | 0.12 ± 0.01 |
| Bone | 0.24 ± 0.01 | 0.24 ± 0.05 | 0.44 ± 0.03 | 0.47 ± 0.07 |
| Brain | 1.24 ± 0.13 | 1.29 ± 0.05 | 1.23 ± 0.08 | 1.24 ± 0.06 |
| Thyroid | 0.07 ± 0.01 | 0.12 ± 0.00 | 0.23 ± 0.05 | 0.29 ± 0.04 |
| Ratios: | | | | |
| Brain/Blood | 33.00 | 64.50 | 35.07 | 54.89 |
| Heart/Blood | 134.78 | 260.80 | 138.57 | 164.22 |

TABLE 7

Biodistribution of $^{125}$I-(N-Benzylpiperidin-
4-yl)-2-iodobenzamide, 2-[$^{125}$I]BP
in Sprague Dawley rats (% ID/whole organ)
each data point represents an average of four rats.

| Tissue | 1 hr. | 6 hr. | 24 hr. |
|---|---|---|---|
| Blood | 2.06 ± 0.42 | 1.30 ± 0.12 | 0.50 ± 0.05 |
| Heart | 0.17 ± 0.03 | 0.05 ± 0.00 | 0.01 ± 0.00 |
| Liver | 22.36 ± 1.29 | 6.07 ± 0.18 | 0.59 ± 0.02 |
| Spleen | 0.32 ± 0.07 | 0.12 ± 0.01 | 0.02 ± 0.00 |
| Kidney | 1.68 ± 0.08 | 0.39 ± 0.06 | 0.05 ± 0.01 |
| Lung | 1.06 ± 0.21 | 0.21 ± 0.02 | 0.04 ± 0.00 |
| Muscle | 16.15 ± 2.13 | 6.75 ± 0.32 | 1.95 ± 0.11 |
| Brain | 0.48 ± 0.12 | 0.05 ± 0.01 | 0.01 ± 0.00 |
| Thyroid | 0.14 ± 0.04 | 1.91 ± 0.23 | 2.11 ± 0.35 |

TABLE 8

Biodistribution of $^{125}$I-(N-Benzylpiperidin-
4-yl)-3-iodobenzamide, 3-[$^{125}$I]BP
in Sprague Dawley rats (% ID/whole organ)
each data point represents an average of four rats.

| Tissue | 1 hr. | 6 hr. | 24 hr. |
|---|---|---|---|
| Blood | 0.75 ± 0.05 | 0.55 ± 0.13 | 0.52 ± 0.05 |
| Heart | 0.15 ± 0.01 | 0.07 ± 0.01 | 0.15 ± 0.01 |
| Liver | 13.35 ± 0.62 | 9.06 ± 0.71 | 6.65 ± 1.63 |
| Spleen | 0.47 ± 0.02 | 0.37 ± 0.05 | 0.65 ± 0.08 |
| Kidney | 3.49 ± 0.23 | 2.25 ± 0.16 | 1.75 ± 0.13 |
| Lung | 0.82 ± 0.07 | 0.43 ± 0.05 | 1.05 ± 0.04 |
| Muscle | 9.36 ± 0.58 | 1.23 ± 0.49 | 03.7 ± 0.44 |
| Brain | 0.61 ± 0.04 | 0.53 ± 0.26 | 0.81 ± 0.07 |
| Thyroid | 0.13 ± 0.02 | 0.53 ± 0.26 | 3.43 ± 0.21 |

EXAMPLE 13

Saturation Binding of 4-[$^{125}$I]BP in MCF-7 Breast Cancer Cells

Competitive binding studies were performed with compounds of the present invention to assess their affinity for sigma sites on human breast cancer cells.

Materials and Methods

MCF-7 cells, a line of human breast cancer cells, were obtained from the National Cancer Institute. These cells were cultured in serum supplemented medium (RPMI-1640) containing 10% heat inactivated fetal bovine serum (GIBCO) at 37° C. The cells were adherent and split weekly in a 1:20 ratio using trypsin/EDTA (GIBCO). The cells were then transferred to 24 well plates and allowed to be adherent and confluent (about 0.5 million cells) or the cells were grown in T75 cell culture flasks and were detached when they were confluent using trypsin/EDTA with DMEM.

I-(N-Benzylpiperidin-4-yl)-4-iodobenzamide, 4-[$^{125}$I]BP, was prepared according to the description in Example 3.

[$^{3}$H]DTG was obtained from DuPont NEN Boston, Mass.

Scatchard Analysis of Binding of [$^{3}$H]DTG in MCF-7 Cell Membranes

Crude membranes from MCF-7 cells were prepared by homogenization of cells (Potter-Elvehjem homogenizer with teflon pestle) in ice-cold 10 mM tris-HCl, pH 7.4 containing 0.32M sucrose at a density of 1×10$^{7}$–10$^{8}$ cells/ml. The homogenate was then centrifuged at 31,000×g for 15 min. at 4° C. and the pellet resuspended in ice-cold 10 mM tris-HCl, pH 7.4 to a protein concentration of 15–20 mg/ml, as determined by method of Lowry with bovine serum albumin as standard. Binding assay with [$^{3}$H]DTG was carried out under the conditions described in Example 9 for sigma-2 receptors except that a temperature of 37° C. was used. Using 15 different concentrations ranging from 1–400 nM, [$^{3}$H]DTG was incubated in the presence of 1 µM dextrallorphan. A combination of labeled and unlabeled ligand was used to achieve concentrations above 15 nM for [$^{3}$H]DTG.

In Vitro Scatchard Plot of 4-[$^{125}$I]BP in MCF-7 Breast Cancer Cells

The Scatchard analysis was carried out using cell suspension in culture tubes (13×100 mm). 4-[$^{125}$I]BP was incubated with MCF-7 cells (10,000–20,000 cells) in 12 concentrations at 0.01 nM to 300 nM. A combination of labeled and unlabeled ligand was used. The non-specific binding was determined in the presence of 10$^{-5}$M 4-IBP. The cells were incubated for 1 hr. at 37° C. in a $CO_2$ incubator. The cells were filtered through a Brandel Cell Harvester on a Whatman Filter 1 and washed twice with 3.0 mL of de-ionized water. The activity associated with the cells was counted in Beckman Gamma Counter (DP 5500). The data obtained were analyzed using the iterative curve-fitting program, BDATA (EMP Software, Baltimore, Md.). The amount of protein was determined using bicinchonic acid (BCA) protein assay reagent obtained from Pierce, Rockford, Ill. with bovine serum albumin as the standard.

Results

Figure 5:
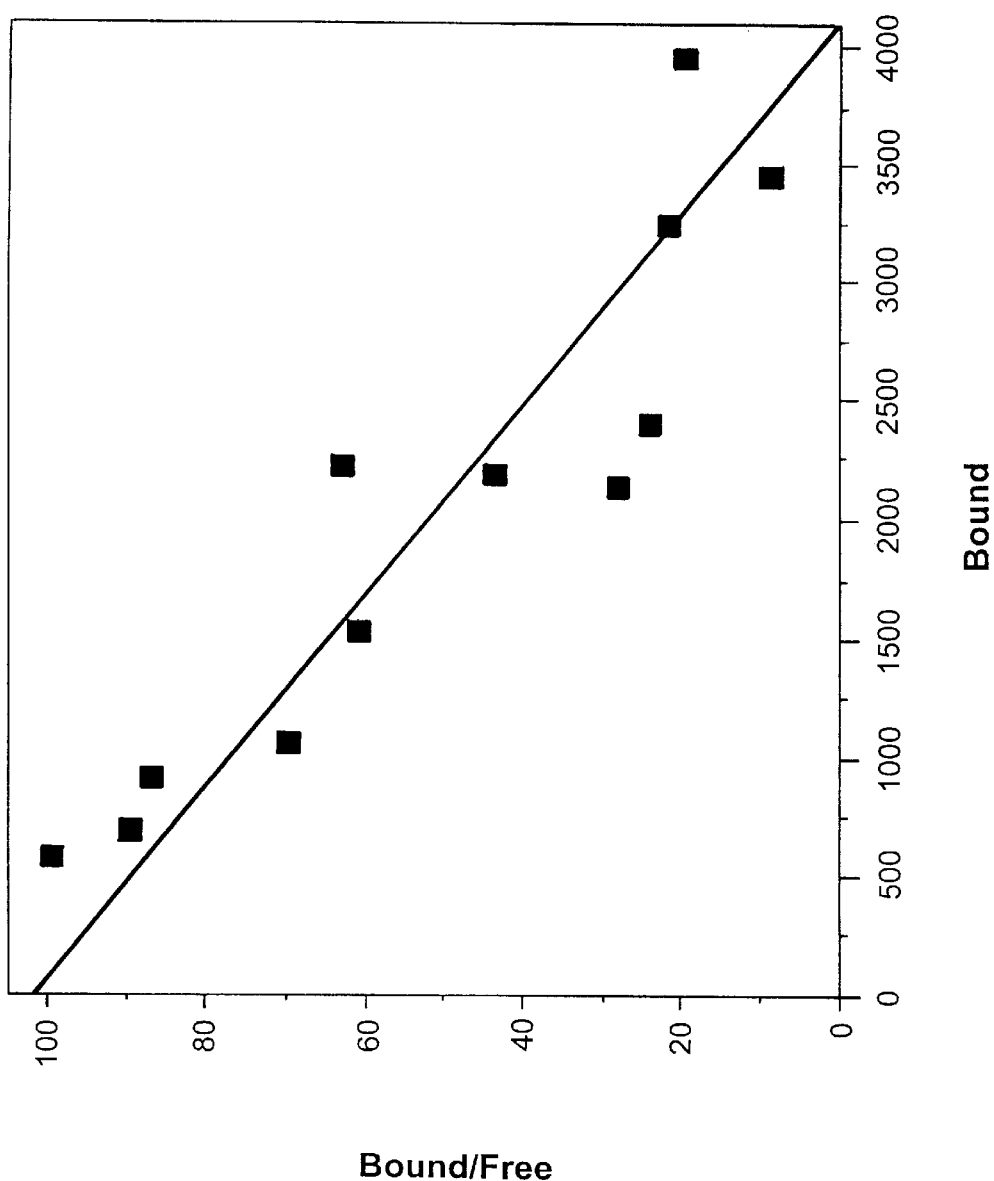

The Scatchard analyses for binding of [$^{3}$H]DTG in MCF-7 cells are shown in FIG. 5.

Figure 6:
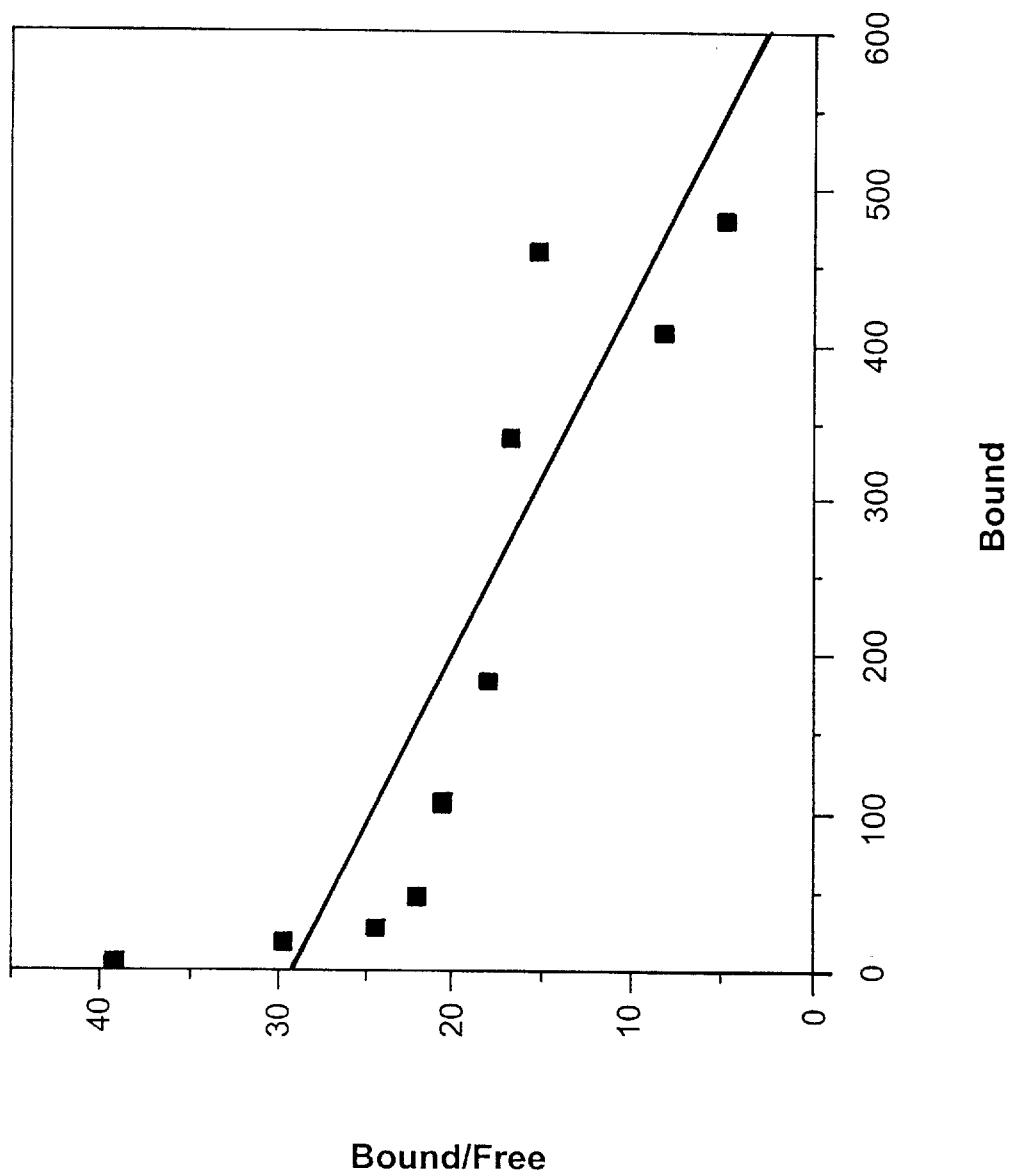

The Scatchard plot for 4-[$^{125}$I]BP binding in MCF-7 cells is shown in FIG. 6.

The results indicate that 4-[$^{125}$I]BP exhibits saturable binding with Kd=26 nM and B=4000 fmol/mg protein.

The results for [$^{3}$H]DTG, a known sigma ligand, gave Kd of 38.2 nM and $B_{max}$ of 3867 fmol/mg protein.

The results in Table 7 show the results of Scatchard analysis of [$^{3}$H](+)pentazocine binding to sigma-1 sites and [$^{3}$H]DTG binding to sigma-2 sites.

TABLE 7

| Cell Line | Sigma-1 ([$^{3}$H](+)-pentazocine) | Sigma-2 ([$^{3}$H]DTG + DEX) |
|---|---|---|
| MCF-7 breast adenocarcinoma | No specific binding | $K_d$ = 24.54 ± 5.57 |
| T47D breast ductal carcinoma | $K_d$1 = 6.62 ± 1.03<br>$B_{max}$1 = 108 ± 64.6<br>$K_d$2 = 261 ± 41.48<br>$B_{max}$2 = 1690 ± 164 | $K_d$ = 19.95 ± 3.53<br>$B_{max}$ = 1221 ± 264 |
| LNCaP.FGC prostate | $K_d$ = 38.44 ± 17.78<br>$B_{max}$ = 11.96 ± 490 | $K_d$ = 39.00 ± 0.40<br>$B_{max}$ = 727 ± 5.67 |

EXAMPLE 14

Homologous and Heterologous Competition Binding Studies in MCF-7 Cells

The affinity of compounds for sites labeled by 4-[$^{125}$I]BP and 2-[$^{125}$I]BP in MCF-7 cells was determined by homologous and heterologous in vitro competitive binding assays in intact cells.

Materials and Methods

Haloperidol, a known non-selective sigma ligand was obtained from RBI, Boston, Mass.

DTG, a known selective sigma ligand, was obtained from RBI, Boston Mass.

4-[$^{125}$I]BP was prepared according to the description in Example 3.

2-[$^{125}$I]BP was prepared according to the description in Example 5.

In Vitro Affinity of 4-[$^{125}$I]BP And 2-[$^{125}$I]BP for MCF-7 Breast Cancer Cells Intact adherent cells were washed (2×1 mL) with 10 mM phosphate buffer (pH=7.2). The cells were incubated with DMEM and incubated with 4-[$^{125}$I]BP and varying concentrations ($10^{-4}$ to $10^{-12}$M) of 4-IBP keeping a total volume 1.0 mL constant in each well. The optimum pH for the binding was found to be between 7–7.5. Each data point represent an average of three values. The cells were incubated at 37° C for 1 hr. and subsequently washed with phosphate buffer (10 mM; pH 7.2) (3×1 mL). The cells were then dissolved in 0.2N NaOH (1.0 mL) and the activity counted on a Beckman (DP 5500) Gamma Counter. The competition binding assay results are listed in Table 7. A similar procedure was repeated with 2-[$^{125}$I]BP with MCF-7, MDA-MB 231 and T47D breast cancer cells.

Results

Figure 8:
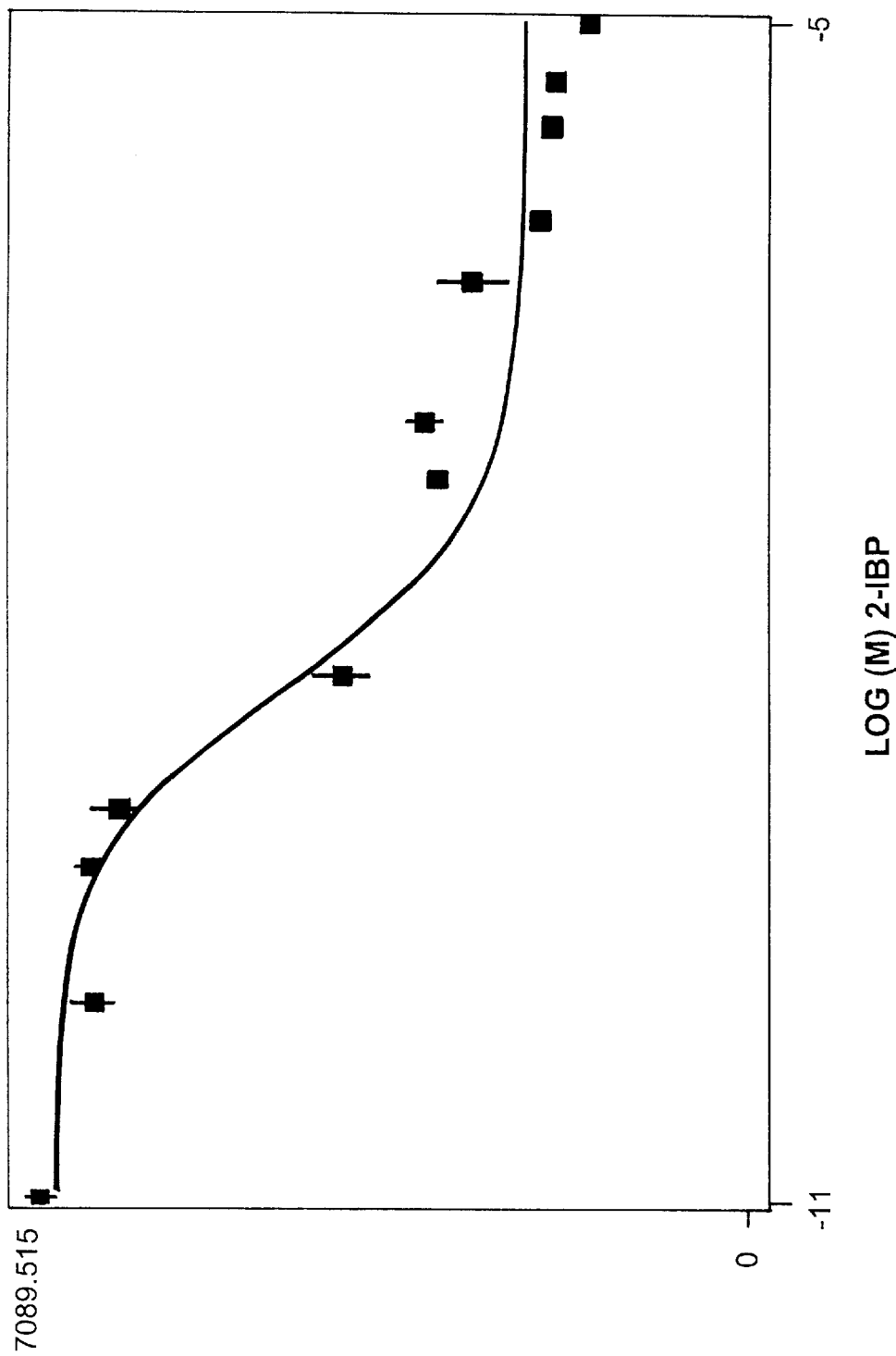
Figure 9:
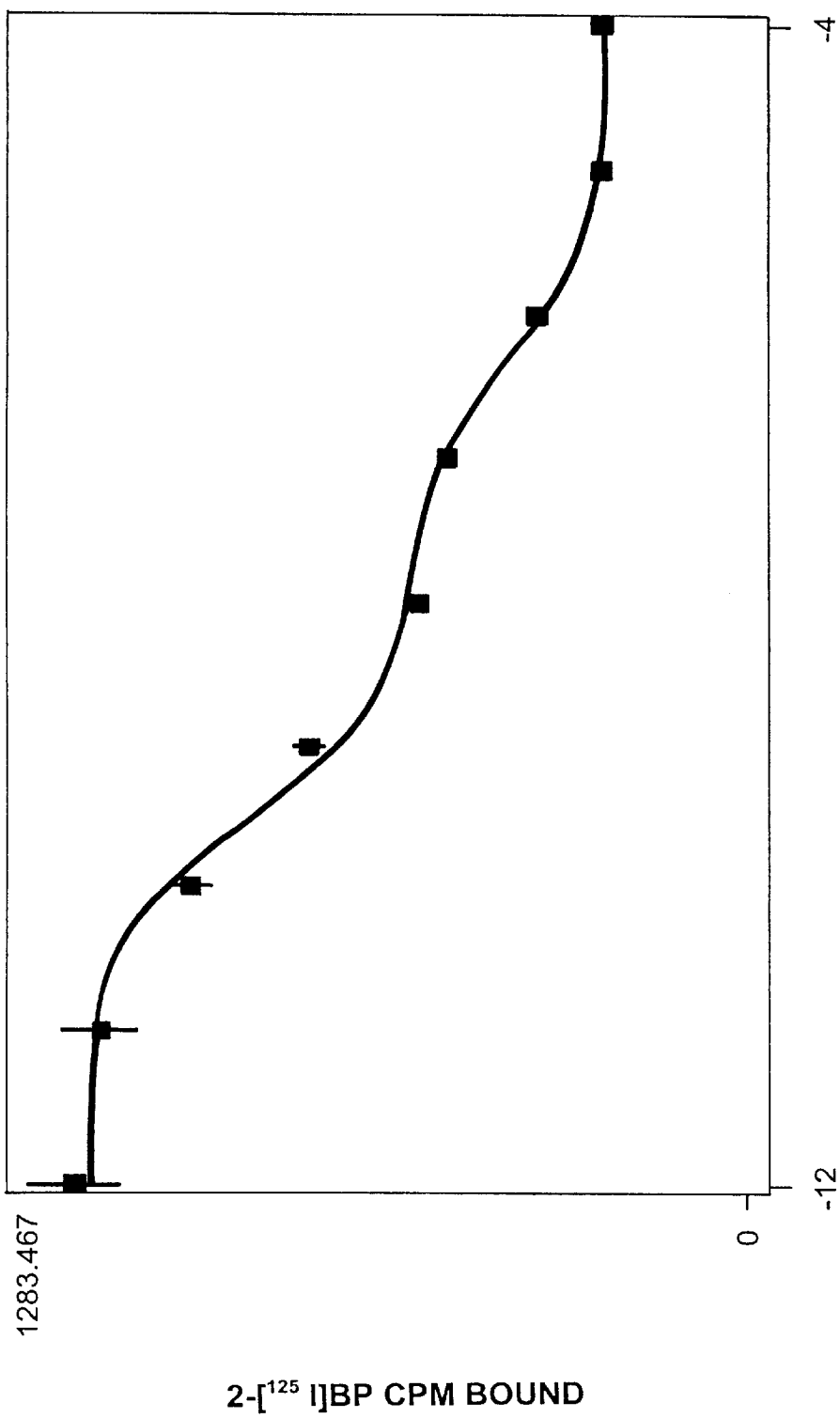
Figure 10:
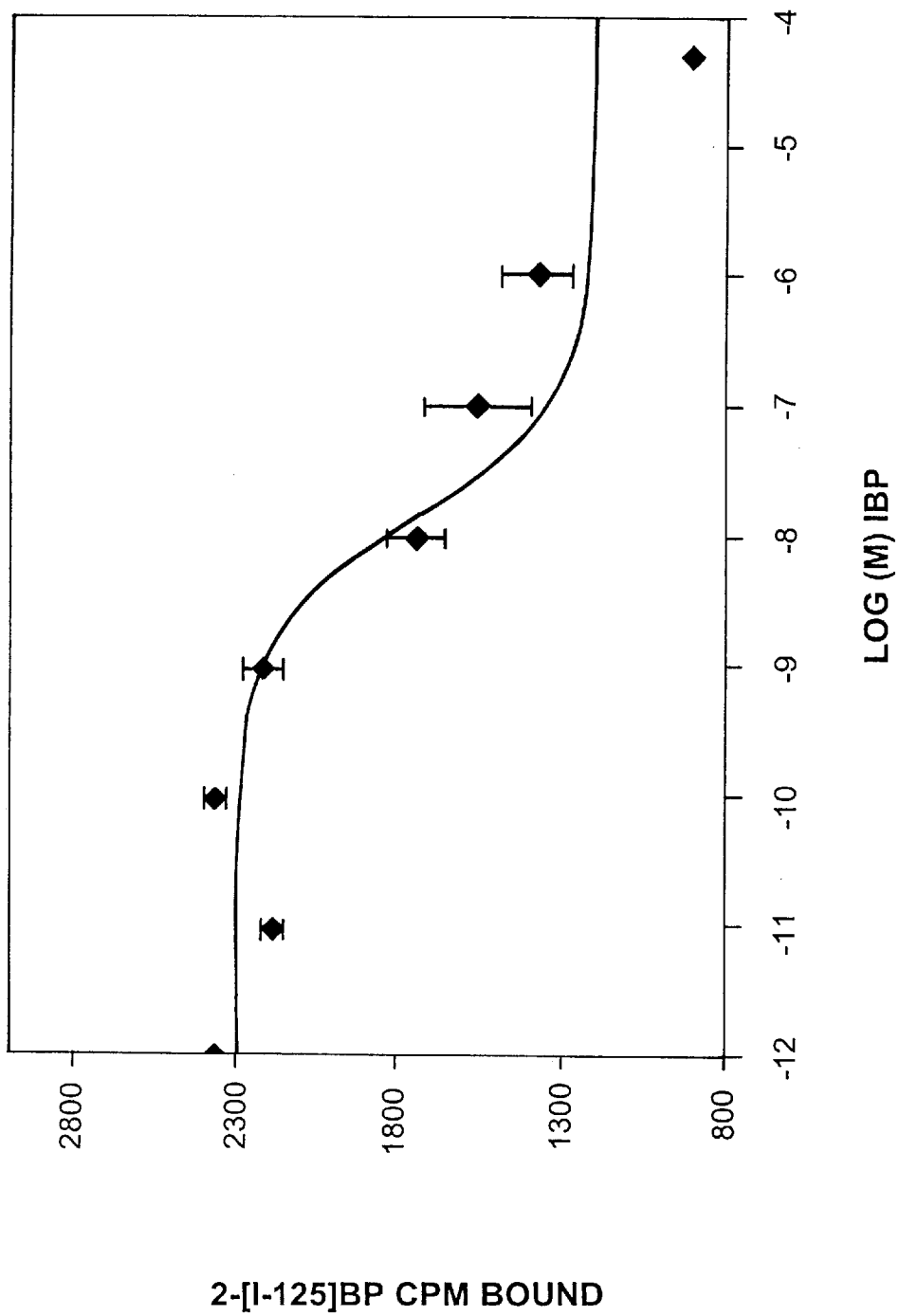

Homologous competition binding of radiolabeled 2- and 4-[$^{125}$I]BP to MCF-7 cells showed high affinity binding. FIG. 8 shows homologous competition binding assays of 2-[$^{125}$I]BP in MCF-7 breast cancer cells. FIGS. 9 and 10 show the homologous competition binding assays of 2-[$^{125}$I] BP in MDA-MB-231 and T47D breast cancer cells suggesting the high affinity binding is common to other commercially available cells line.

Figure 7:
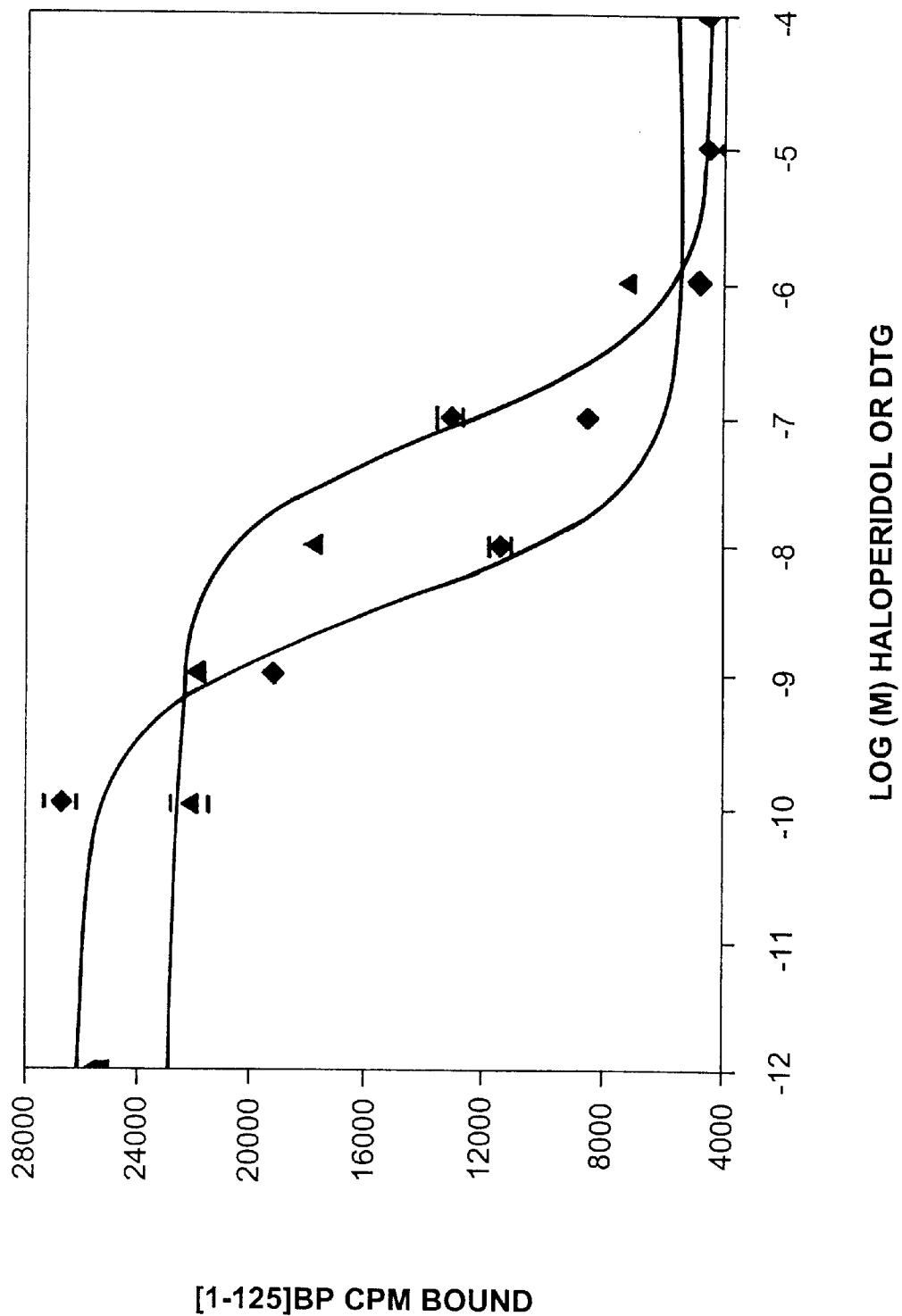

Heterologous competition assays using DTG and haloperidol showed high affinity, concentration-dependent inhibition of specific binding. Competition assays for the binding of 4-[$^{125}$I]BP and 2-[$^{125}$I]BP with haloperidol in MCF-7 breast tumor cells are shown in FIGS. 7 and 8.

The Ki for DTG and haloperidol were found to be 56±15 and 4.6+0.9 nM, respectively, suggesting the labeling of sigma sites by 4-[$^{125}$I]BP in MCF-7 cells.

Table 8 shows inhibitor constants, Ki, for 4-$^{125}$I]BP binding in MCF-7 breast cancer cells for various drugs. In addition, MCF-7 cells showed little or no specific binding of (+)-pentazocine suggesting the absence of sigma-1 receptors in this cell line. However in T47-D breast cells, the binding of [$^3$H]DTG and [$^3$H]-(+)-pentazocine suggest the presence of both sigma-1 and sigma-2 receptors.

TABLE 8

| Ligands | Ki |
| --- | --- |
| Haloperidol | 4.6 ± 0.9 |
| IBP | 4.8 ± 2 |
| DTG | 56 ± 15 |
| Spiperone | 247 ± 37 |
| (±) Verapamil | 379 ± 75 |
| (−)-Pentazocine | >1000 |
| (+)-PPP | >1000 |
| (+)-Pentazocine | 1479 ± 190 |
| (+)SKF 10,047 | >10000 |
| (−)SKF 10,047 | >10000 |

EXAMPLE 15

Diagnostic Imaging using $^{125}$I-(2-PiperidinylAminoethyl)-4-IodoBenzamide

These experiments illustrate the present diagnostic imaging procedures and the benefit of utilizing the present compounds in such procedures.

Materials and Methods

A2058 cells, derived from a brain metastasis of human malignant melanoma (Todaro et al. 1980 Proc. Natl. Acad. Sci. USA 77: 5258) were obtained from the National Institutes of Health. A human lung adenocarcinoma cell line, NCI-838, was obtained from the National Cancer Institute. These cells were grown in DMEM2 medium (Dulbecco's modification of Eagle's medium, EMEM) supplemented with 10% fetal bovine serum and 0.03% L-glutamine. $^{131}$I-N-(diethylaminoethyl)4-iodobenzamide (i.e. [$^{131}$ I]DAB) was prepared as described in John et al. (1993 Nucl. Med. Biol. 20: 75–79.

$^{131}$I(2-piperidinylaminoethyl)4-iodobenzamide(D) was synthesized as described in Example 1.

Nude Mice Imaging

Balb/c nu/nu mice (17–22 g) bearing human melanoma or non-small cell lung carcinoma xenograft tumors were injected intravenously with 0.2 ml of saline solution containing [$^{131}$I]PAB or [$^{131}$I]DAB (150–200 $\mu$Ci). The animals were anesthetized with ketamine containing rompun before the imaging studies. The images were obtained using a scintigraphic camera with a pin-hole collimator at 6 and 24 hr. post injection.

FIGS. 2 and 3 provide scintigrams of nude mice implanted with human melanoma xenografts and treated with [$^{131}$I]PAB and [$^{131}$I]DAB, respectively.

Figure 2A:
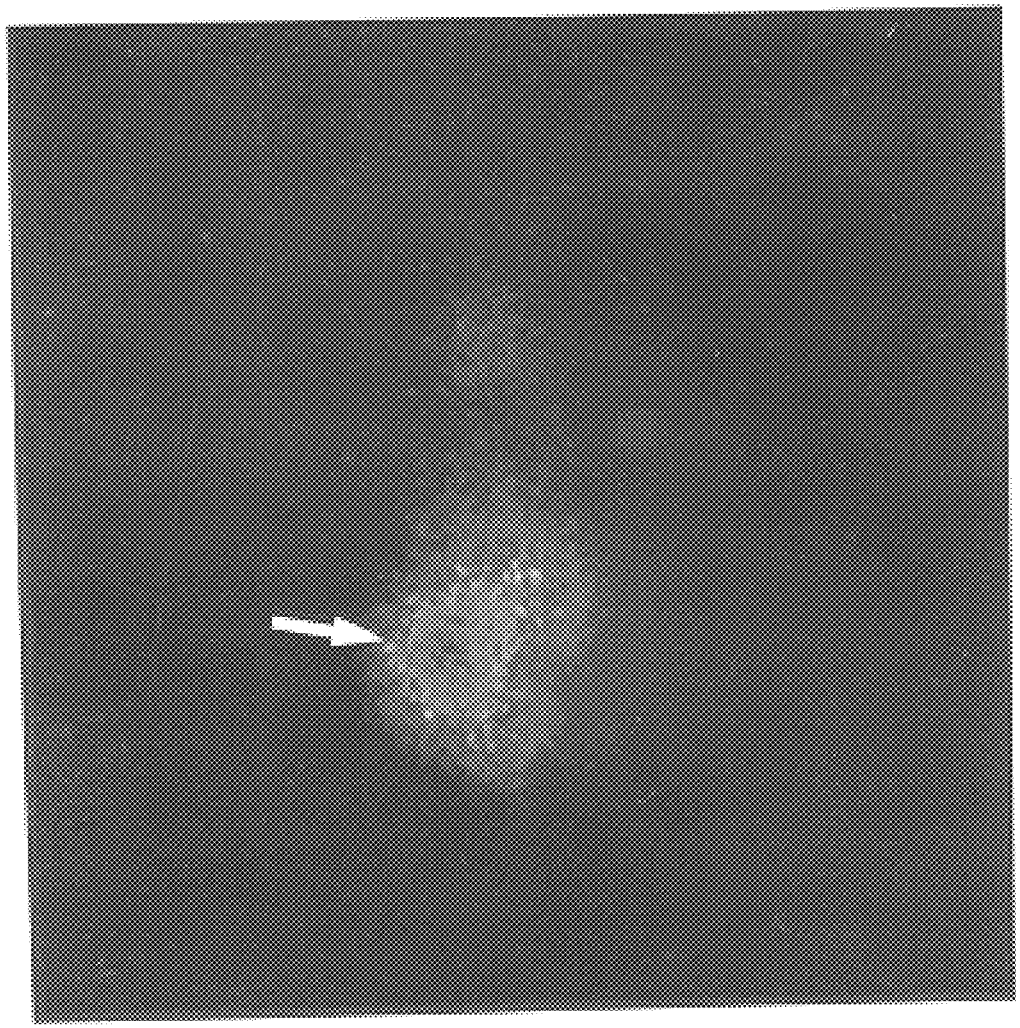
Figure 2B:
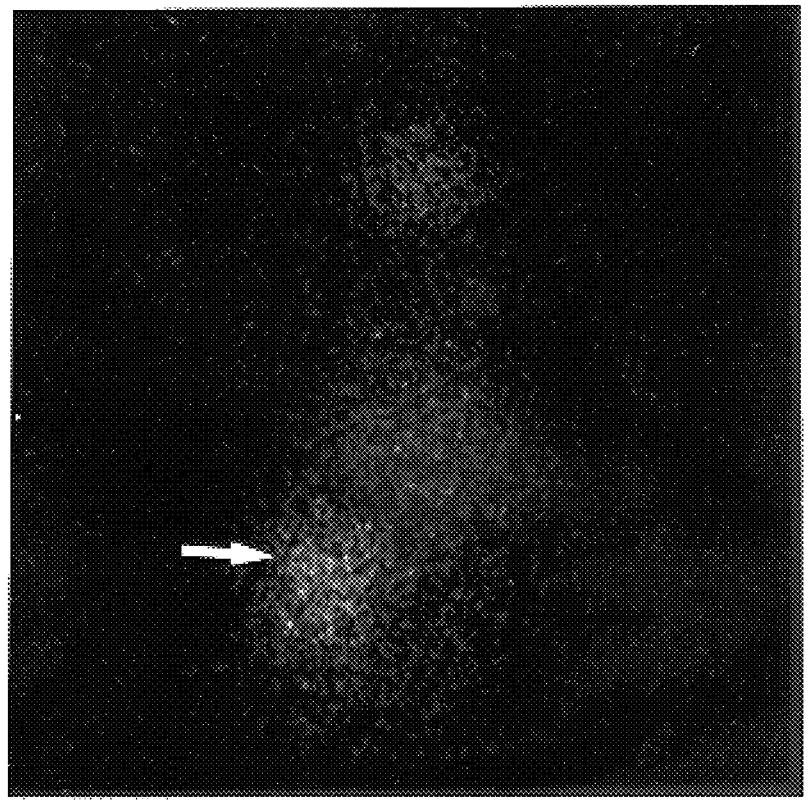
Figure 3A:
Figure 3B:
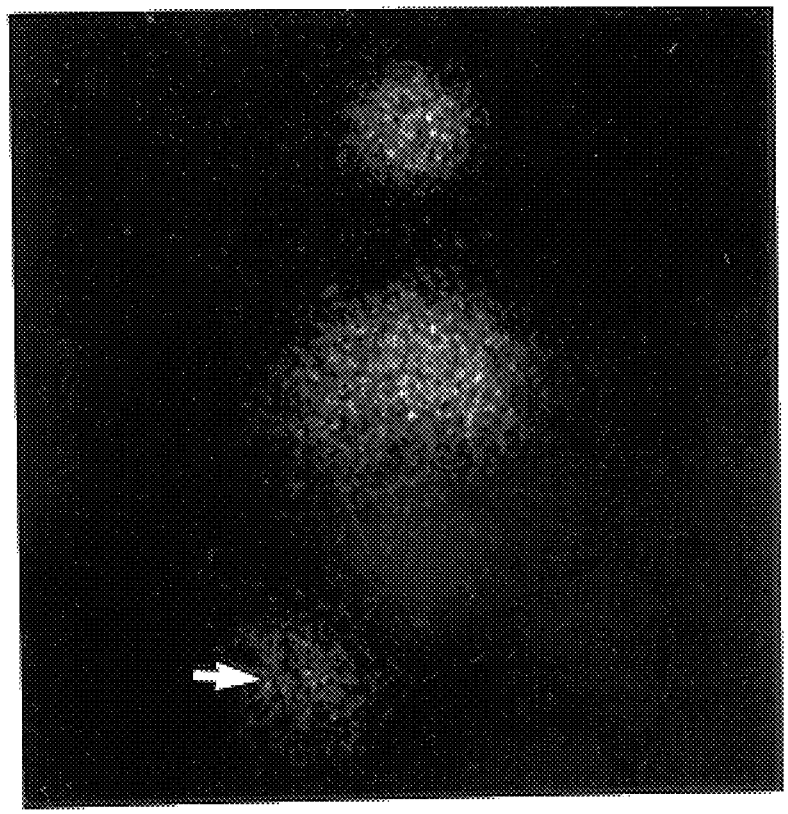

At 6 and 24 hrs. post injection, [$^{125}$I]PAB was detected only within the tumor (FIGS. 2A and 2B). In contrast, no [$^{131}$I]DAB was detected in the tumor at either 6 or 24 hrs. after administration (FIGS. 3A and 3B). Moreover, considerable uptake of [$^{131}$I]DAB had occurred in the livers of mice receiving this agent by 6 and 24 hrs. post-administration (FIGS. 3A and 3B). Little or no [$^{131}$I]PAB was observed in the liver at either 6 or 24 hours. post-administration. These data indicate IPAB is a significantly better diagnostic agent for tumor imaging than IDAB.

Figure 4:
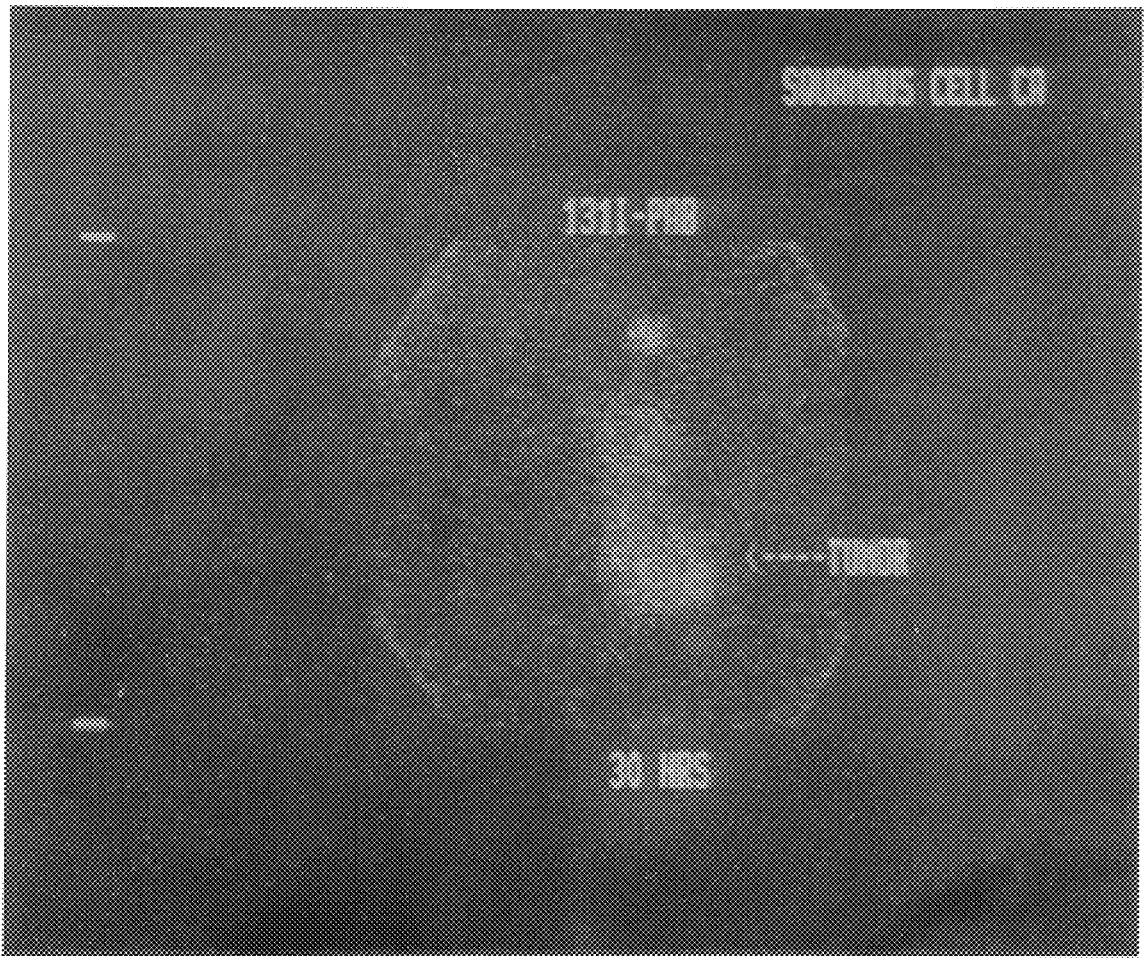

FIG. 4 provides a scintigram of a nude mouse implanted with a human adenocarcinoma xenograft 30 hrs. after injection of [$^{131}$I]PAB. These scintigraphic imaging studies easily visualized the implanted tumor at both 24 and 30 hrs. post-injection.

EXAMPLE 16

Synthesis of N-[(4-[$^{125}$I]-Iodophenyl)ethyl]-N-methyl-2-(1-piperidinyl)ethylamine Preparation of N-methyl-2-(1-piperidinyl) ethylamine To an aqueous solution of (40%) of methylamine (235 ml, 3.0 mol) was added dropwise a solution of cholorethyl piperidine monohydrochloride (50 g, 0.27 mol). The mixture was stirred overnight and then basified by addition of NaOH. A colorless oil separated from the aqueous solution. This oil was extracted (2×200 ml) with ether. The solvents were evaporated under low temperature and a clear oil was obtained. This oil was used without any further purification.

Preparation of N-[2-(4-bromophenyl) acetyl]-N-methyl-2-(1-piperidinyl)ethylamine To a solution of 4-bromophenylacetic acid (10 g, 46.5 mmol) in CHCl$_3$ (100 ml) was added thionyl chloride (8 ml) in CHCl$_3$ (10 ml) and three drops of DMF. The mixture was reflux for one to two hours. The volatiles were removed in vacuo to give a light yellow oil. This acid chloride was dissolved in CHCl₃ 30 ml and added dropwise to another flask containing N-methyl-2-(1-piperidinyl)ethyl amine (6.1 g, 48 mmol) and triethylamine (25 ml) and CHCl₃ (100 ml) at 0° C. The reaction mixture was stirred overnight at room. The volatiles were removed, the residue dissolved in CHCl₃ (150 ml) and washed with (2×100 ml) water and 2% NaHCO₃ (50 ml). The organic layer was dried and the volatiles were removed to give a light yellow oil (15.0 g). The oil was passed through a silica gel column and eluted with CHCl₃/MeOH to give 13 g, (87%) of the desired pure compound. ¹H NMR 1.30–1.54 (m, 6H, piperidinyl CH₂); 2.33–2.43 (m, 6H, NCH₂); 2.92 (44%), 2.96 (56%) (s, 3H, N-Me); 3.32–3.37 (46%), 3.45–3.49 (54%), (t, 2H, J=7.1 Hz, NCH₂); 3.61 (56%), 3.67 (44%), (s, 2H, benzylic); 7.09–7.11 (d, 2H, arom); 7.38–7.41 (d, 2H, arom).

Preparation of N-[2-(4-bromophenyl)ethyl]-N-methyl-2-(1-piperidinyl)ethylamine

To a solution of the above amide (10 g, 29.4 mmol) in THF (200 ml) was added in small portions lithium aluminum hydride (LAH) (2.2 g, 2 fold excess). The mixture was heated under reflux for three hours and stirred overnight. The slurry was cooled and a saturated solution of sodium ammonium tartrate was added dropwise carefully. After all excess LAH had decomposed, CHCl₃ (250 ml) was added. The organic layer was separated from the aqueous layer, dried over anhydrous Na₂SO₄ and the volatiles were removed in vacuo to give a yellow oil. The oil was passed over a silica gel column and eluted with CHCl₃ and then with CHCl₃/MeOH:90/10. The desired fractions were pooled together and the solvents evaporated to give 7.4 g of the desired product. ¹H NMR 1.4–1.5 (m, 2H, CH₂); 1.7–1.8 (m, 4H, piperidinyl CH₂); 2.35 (S, 3H, NMe); 2.5–2.80 (m, 12H, NCH₂); 7.09–7.11 (d, 2H, arom); 7.38–7.41 (d, 2H, arom).

Preparation of N-[2-(4-n-tributylstannylphenyl)ethyl]-N-methyl-2-(1-piperidinyl)ethyl amine To a solution of amine (3.0 g, 0.92 mmol) was added Pd(PPh₃)₄ (1.0 g, 0.092 mmol) and bistributyltin (5.3 g, 0.92 mmol) and triethyl amine (100 ml). The mixture was refluxed overnight. The solvents were removed in vacuo and the residue dissolved in CHCl₃ (10 ml) and purified after passing through a silica gel column and eluting with CHCl₃ (75 ml) and then CHCl₃/MeOH:90/10. The desired fractions were combined, the solvents were evaporated to give an oil (4.6 g). ¹H NMR: 0.8–1.1 (m, 12H, Bu₃ and piperidinyl); 1.2–1.6 (m, 18H, nBu₃); 2.3 (s, 3H, NMe); 2.4–2.8 (m, 15H, NCH₂); 7.1–7.15 (d, 2H, arom); 7.3–7.35 (d, 2H, arom). ¹³C NMR: 9.51, 13.65, 23.65, 24.98, 27.37, 29.07, 33.45, 42.29, 54.67, 2.84, 59.66, 128.33, 128.42, 136.51, 138.99, 139.84. m/e=537 (M+)⁺ (30%); 521 (M-CH₃) (35%).

Preparation of N-[2-(4-iodophenyl)ethyl]N-methyl-2-(1-piperidinyl)ethylamine

A round bottom flask was charged with N-[2-(4-n-tributylstannyl-phenyl)ethyl]-N-methyl-2-(1-piperidinyl) ethyl amine (1.0 g, 1.86 mmol) and iodine (500 mg) and acetone (50 ml). The mixture was stirred at room temperature for 15 hours. An aqueous solution (25 ml) of sodium thiosulfate (15%) was added and the mixture was extracted in CHCl₃. The organic layer was separated and dried and the solvent removed to give a light yellow oil. (M+1)⁺ (100%).

Preparation of N-[(4-[¹²⁵I]-Iodophenyl) ethyl]-N-methyl-2-(1-piperidinyl)-ethylamine The radiolabeled compound was prepared according to the protocol used in Example 3 to prepare ¹²⁵I(-N-benzylpiperidin-4-yl)-4-iodobenzamide, but using N-[2-(4-n-tributylstannyl-phenyl)ethyl]-N-methyl-2-(1-piperidinyl) ethyl amine as starting material. The synthetic procedure is depicted below in Reaction Scheme IV.

Reaction Scheme IV

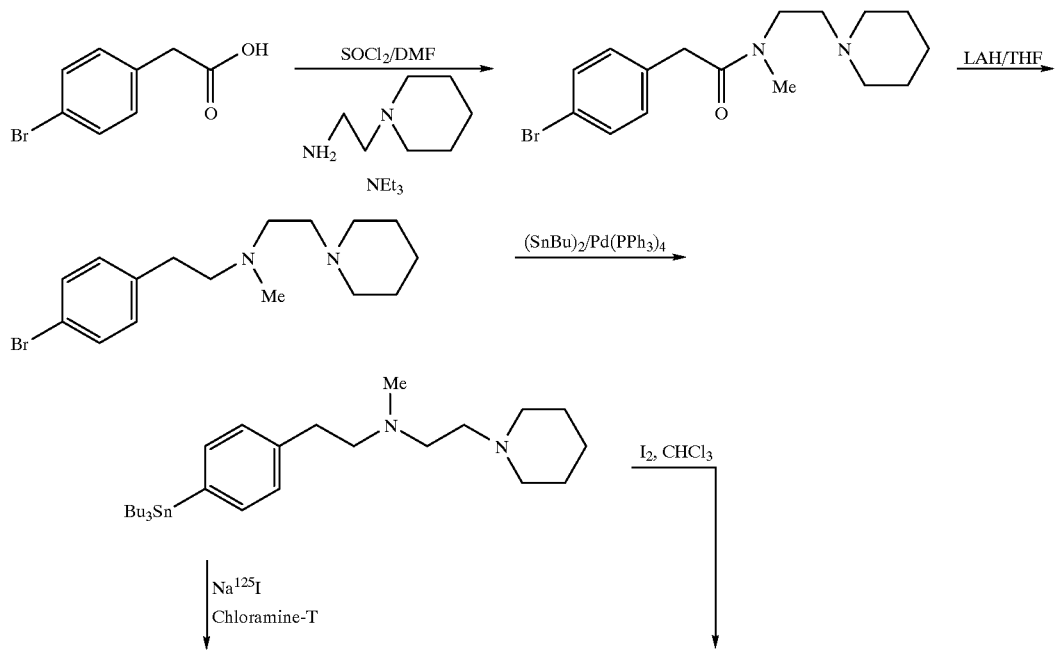

-continued

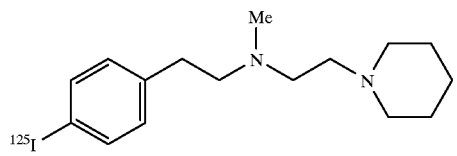

4-($^{125}$I) PEMP

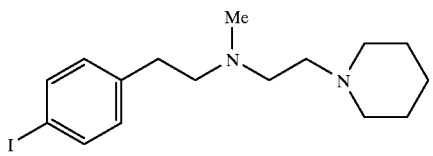

4-IPEMP

EXAMPLE 17

Biodistribution of N-[(4-[$^{125}$I]-Iodophenyl)ethyl]-N-methyl-2-(1-piperidinyl)-ethylamine, 4-[$^{125}$I]PEMP Biodistribution experiments were performed to assess the clearance of N-[(4-[$^{125}$I]-iodophenyl)ethyl]-N-methyl-2-(1-piperidinyl)-ethylamine, 4-[$^{125}$I]PEMP. The compound was prepared according to the procedure described in Example 16. For in vivo studies, Sprague Dawley rats were used. Animal biodistribution assays were performed according to the procedure described in Example 11.

Results

Table 9 illustrates the biodistribution of 4-[$^{125}$I]PEMP in Sprague Dawley rats at one, six, and twenty-four hours after administration of the radiolabeled compound.

The results in Table 9 show that 4-[$^{125}$I]PEMP rapid clearance from the liver, lungs and kidneys.

TABLE 9

Biodistribution of N-[(4-[$^{125}$I]-iodophenyl)ethyl]-N-methyl-2-(1-piperidinyl)-ethylamine, 4-($^{125}$I)PEMP in Sprague Dawley rats (% ID/whole organ) each data point represents an average of four rats.

| Tissue | 1 hr. | 6 hr. | 24 hr. |
|---|---|---|---|
| Blood | 1.82 ± 0.20 | 2.59 ± 0.32 | 1.01 ± 0.12 |
| Heart | 0.30 ± 0.02 | 0.18 ± 0.00 | 0.05 ± 0.00 |
| Liver | 16.56 ± 2.19 | 6.39 ± 0.48 | 1.83 ± 0.16 |
| Spleen | 2.52 ± 0.49 | 0.96 ± 0.10 | 0.28 ± 0.03 |
| Kidney | 4.57 ± 0.88 | 1.45 ± 0.03 | 0.50 ± 0.02 |
| Lung | 4.91 ± 0.23 | 1.22 ± 0.12 | 0.34 ± 0.03 |
| Muscle | 15.60 ± 3.04 | 11.73 ± 0.63 | 5.55 ± 1.25 |
| Brain | 1.79 ± 0.21 | 0.57 ± 0.01 | 0.23 ± 0.00 |
| Thyroid | 0.19 ± 0.02 | 0.20 ± 0.05 | 0.58 ± 0.03 |
| Bone | 0.23 ± 0.00 | 0.28 ± 0.01 | 0.17 ± 0.00 |

EXAMPLE 18

Binding Competition Between Pharmacological Antagonists and N-[(4-I-iodophenyl)ethyl]-N-methyl-2-(1-piperidinyl)-ethylamine, 4-IPEMP

Materials and Methods

N-[(4-I-iodophenyl)ethyl]-N-methyl-2-(1-piperidinyl)-ethylamine, 4-IPEMP, and (bromoiodophenyl)ethyl]-N-methyl-2-(1-piperidinyl)-ethylamine, Br-PEMP, were synthesized as described in Example 16. Assays were prepared according to the procedure described in Example 9.

Results

The Ki values for 4-IPEMP and BR-PEMP are shown in Table 10:

|  | Sigma-1 Guinea Pig Brain [$^3$H]-(+)-pentazocine | Sigma-2 Rat Liver [$^3$H]DTG + DEX |
|---|---|---|
| 4-IPEMP | 7.02 nM | 52.65 nM |
| Br-PEMP | 6.27 nM | 51.79 nM |

These data demonstrate that 4-IPEMP and its bromo precursor bind both sigma-1 and sigma-2 sites with high affinity.

EXAMPLE 19

Homologous and Heterologous Competition Binding Studies in MCF-7 Cells

The affinity of compounds for sites labeled by 4-[$^{125}$I] PEMP was determined by homologous and heterologous in vitro competitive binding assays in intact MCF-7 breast cancer cells and guinea pig brain membranes labeled by 4-[$^{125}$I]PEMP. The assays were prepared according to the procedure described in Example 14.

Results

Figure 11:
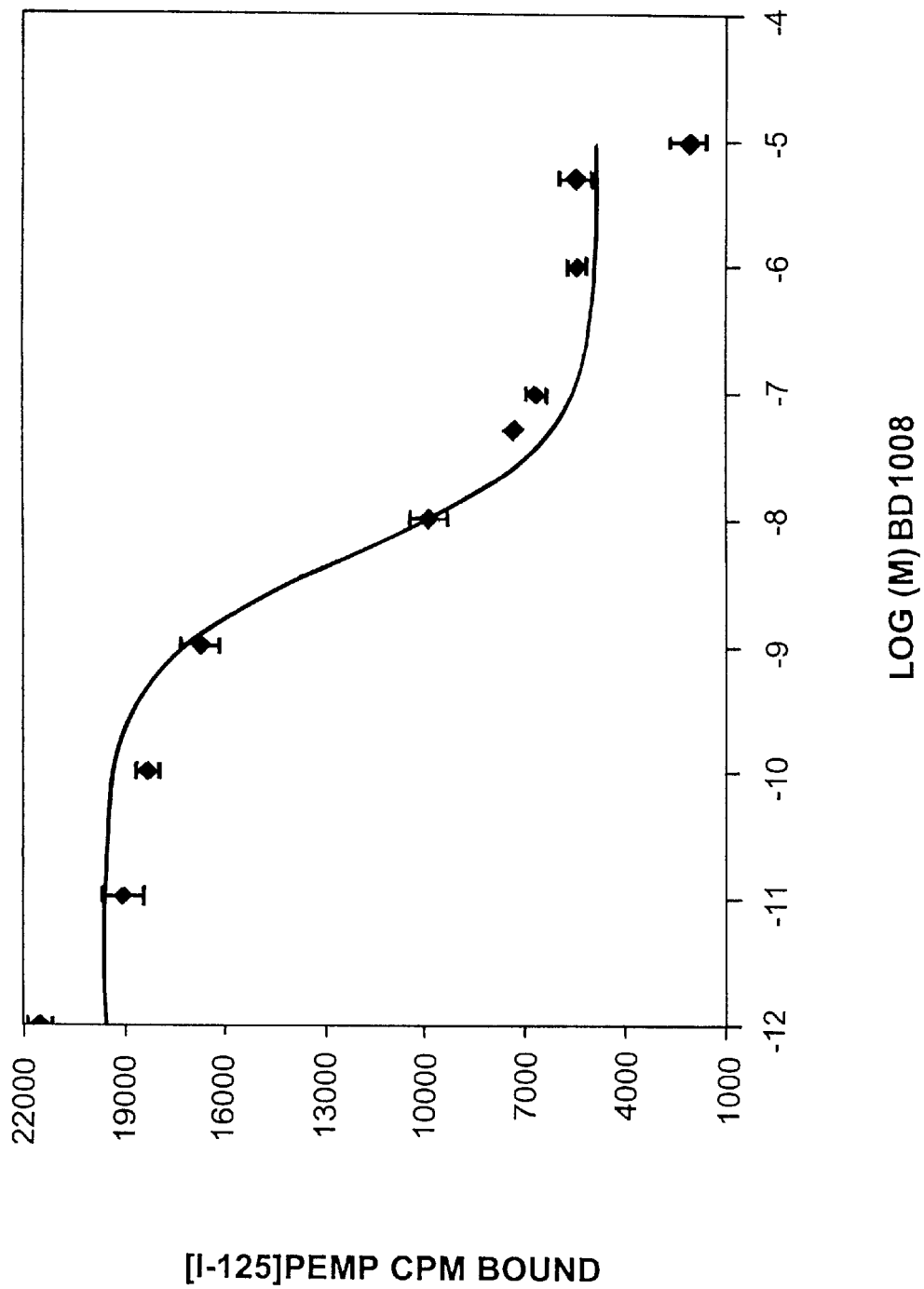

Heterologous competition assays using BD1008, a known sigma ligand show high affinity, concentration-dependent inhibition of specific binding. Competition assays for the binding of 4-[$^{125}$I]PEMP with BD1008 in MCF-7 breast tumor cells are shown in FIG. 11.

The Ki for BD1008, (+)pentazocine and haloperidol were found to be 5.6, 35.9 and 36.5 nM, respectively, suggesting the labeling of sigma sites by 4-[$^{125}$I]PEMP in guinea pig brain membranes.

EXAMPLE 20

Ligan Binding Studies with Breast Tumor Biopsied Samples

An approval was obtained by the Committee on Human Research, GWUMC for in-vitro binding studies of biopsied human tumors.

A small piece of a breast tumor tissue (300 mg), surgically removed from a patient, was obtained from the Department of Pathology, GWUMC.

Membrane Preparations

A small piece of breast tumor tissue (200 mg) was suspended in 10 mL of tris-HCI buffer (50 mM, pH 9.0). The tissue was thoroughly homogenized on a Ultra-turrax polytron for a period of 5–10 minutes. The suspension was centrifuged on a Beckmann centrifuge (Model J 21B centrifuge) for 5 min at 5000 rpm. The resulting pellet was washed with tris-HCI, (50 mM, pH 9.0) and centrifuged again for 20 min at 18000 rpm. The supernatant was discarded and the pellet was resuspended in 10 mL of tris-HCl (50 mM, pH 9.0). The protein was determined using BCA protein assay reagent obtained from Pierce, Rockford, Ill. with BSA as a standard.

Ligand Binding Studies with Breast Tumor Biopsied Samples

Figure 12:
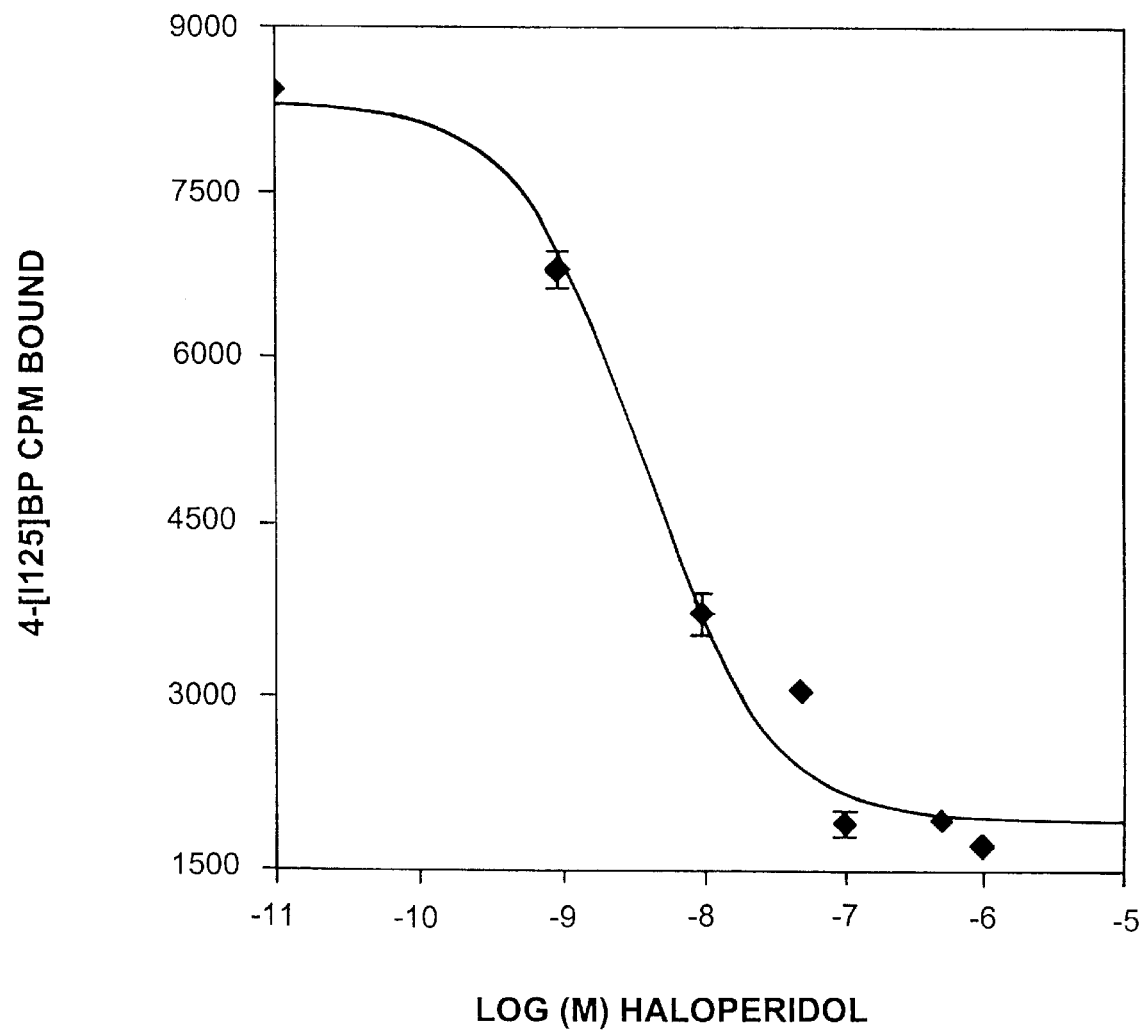
Figure 13:
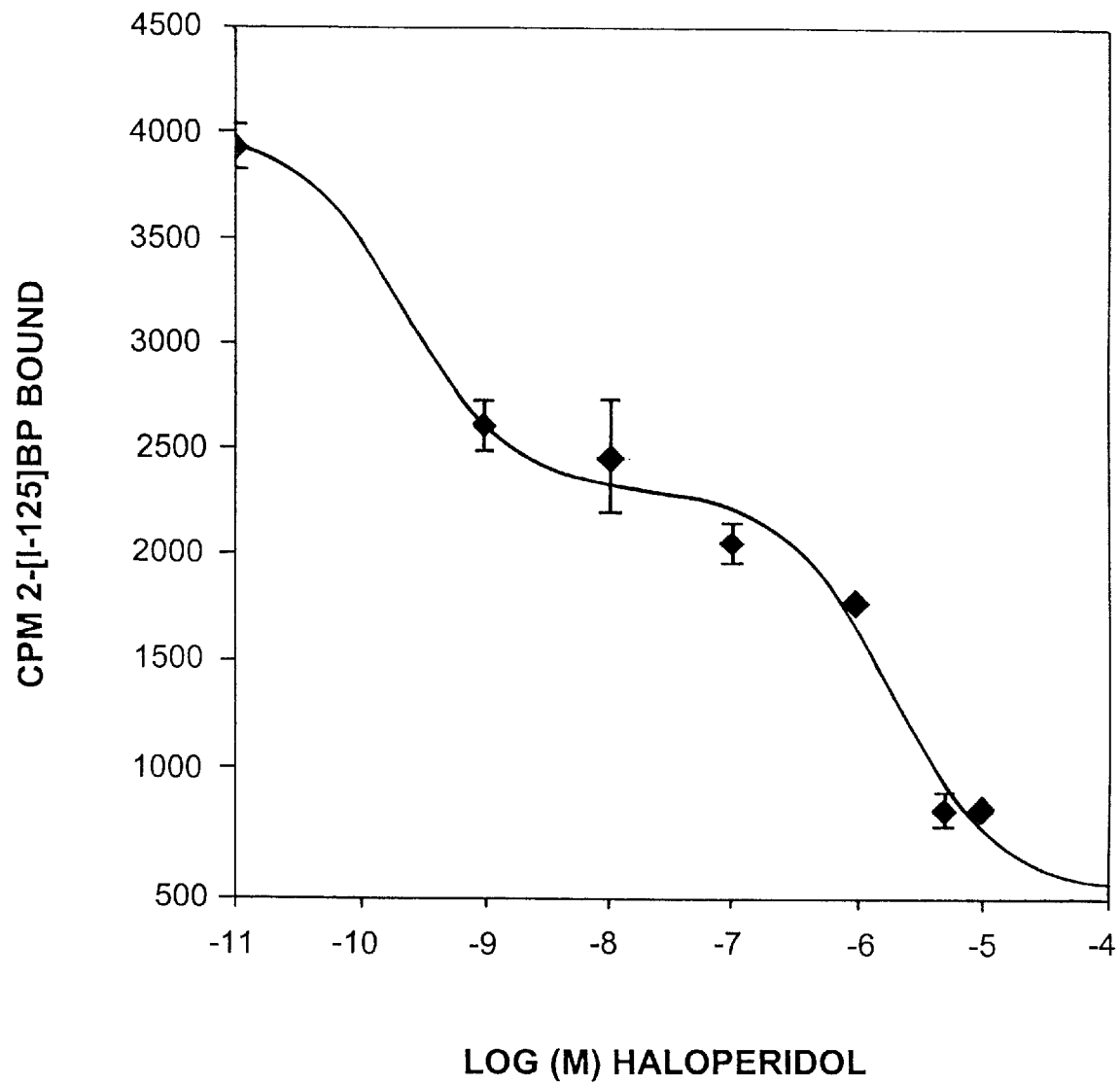

The small portion (0.1 mL) of the membranes were aliquotted in tissue culture tubes and incubated with radio-iodinated ligands 4-[$^{125}$I]BP and 2-[$^{125}$I]BP (0.1 mL) and a varying amount of competing ligand (0.1 mL haloperidol). The contents were incubated in a waterbath for 1 hr at 37° C. The assays were terminated by the addition of ice cold tris buffer (5 mL) and filtration through glass fiber filters using a cell harvester (Gaithersburg, Md.). The activity bound to membranes was then counted using Beckman Gamma Counter (DP 5500). The data obtained were analyzed using the iterative curve-fitting program, BDATA (EMF Software, Baltimore, Md.). A representative example is given in FIGS. 12 & 13.

Results

A high affinity binding of 2-[$^{125}$I]BP with haldoperidol (Ki=6.3 nM) suggested the binding to sigma receptors present on the breast tissue membranes. Similarly, a high affinity dose dependent binding of 4[$^{125}$I]BP with haloperidol, a sigma ligand, was observed (Ki=3.8 nM).

EXAMPLE 21

Biodistribution of $^{125}$I-(N-benzylpiperidin-4-yl)-2-IodoBenzamide

Biodistribution experiments are performed to assess the tumor-specificity of 2-[$^{125}$I]BP.

Materials and Methods

Breast cancer cell lines MCF-7, T47D and MDA-MB-231 are obtained from ATCC, Rockwell, Md.

Tumor cells are grown in DMEM2 medium (Dulbecco's modification of Eagle's medium, EMEM) supplemented with 10% fetal bovine serum and 0.03% L-glutamine.

$^{125}$I-N-(N-benzylpiperidin-4-yl)-2-iodobenzamide (i.e.2-[$^{125}$I]BP) is prepared as described in Example 5.

Animal Biodistribution Assays

For in vivo studies, tumor cells are harvested using calcium and magnesium free PBS containing 0.02% EDTA. Suspension of 5×10$^6$ cells (viability greater than 95%) in 0.2 mL of medium are inoculated subcutaneously in female Balb/c nu/nu mice. In about two weeks, solid tumors of about 1 cm in diameter appear in approximately 85% of all inoculated mice. Mice with solid tumors having a diameter of about 1 cm are used for biodistribution studies.

Balb/c nu/nu mice (17–22 g) are injected intravenously with 0.2 ml of a saline solution containing [$^{125}$I]PB (5–6 μCi). At 1, 6 and 24 hr. after injection, blood samples are collected by cardiac puncture and the mice are sacrificed immediately thereafter by cardiectomy while under halothane anesthesia. The organs of interest are subsequently excised, blotted with tissue paper, weighed, and the radioactivity counted using a Packard automatic counter (autogamma 5650). The % injected dose/g (% ID/g) values are determined by comparison of tissue radioactivities with suitably diluted aliquots of the injected [$^{125}$I]PB dose divided by the weight of the organ. The values obtained are normalized to a mouse weighing 20 g.

What is claimed:

1. A method for targeting a tumor for diagnosing the presence of a mammalian tumor in a mammal which comprises administering to a mammal an imaging effective amount of a compound of the formula:

$$R_a \underset{R_b}{\overset{X}{\bigg|}} (R_1)_q - (CH_2)_j - CZ - NR_3 - (CH_2)_y - R_2$$

wherein:
X is a non-metal γ-emitting radionuclide;
Z is two —H;
each $R_1$ is independently H, halo, lower alkyl, or lower alkoxy;
$R_a$ and $R_b$ are independently H, halo, lower alkyl, or lower alkoxy or $R_a$ and $R_b$ taken together with the carbon atoms to which they are attached from a cycloalkenyl having 3–7 ring carbon atoms or a heterocyclic ring; said heterocyclic ring having 2–5 ring carbon atoms, 1–3 ring heteroatoms and up to a total of six ring atoms;
$R_2$ is —N(R$_3$)$_2$ or a 5 to 7 membered nitrogen containing heterocyclic ring which has zero or up to two oxygen ring atoms, which heterocyclic ring is unsubstituted or substituted with at least one alkyl or substituted or unsubstituted arylalkyl substituent, said alkyl containing 1–6 carbon atoms, said nitrogen containing heterocyclic ring having up to seven ring atoms including 2–6 ring carbon atoms and 1–3 ring heteroatoms of which at least one is nitrogen, said arylalkyl being unsubstituted or substituted with a halogen, alkoxy or alkyl group;
each $R_3$ is independently hydrogen or lower alkyl;
j and y are independently an integer from 0 to 6;
q is an integer from 0 to 2;
wherein
said tumor is selected from the group consisting of lung carcinoma, colon carcinoma, renal carcinoma, melanoma, glioma, pheochromocytoma, prostate carcinoma, neural tumor, breast carcinoma, neuroblastoma and brain carcinoma.

2. A method for targeting a tumor in a mammal for treating said tumor which comprises administering to a mammal in need thereof a composition comprising a tumor-inhibiting effective amount of a compound of the formula:

$$R_a \underset{R_b}{\overset{X}{\bigg|}} (R_1)_q - (CH_2)_j - CZ - NR_3 - (CH_2)_y - R_2$$

wherein:
X is an α-emitting or β-emitting radionuclide;
Z is two —H;
each $R_1$ is independently H, halo, lower alkyl, or lower alkoxy;
$R_a$ and $R_b$ are independently H, halo, lower alkyl, or lower alkoxy or $R_a$ and $R_b$ taken together with the carbon atoms to which they are attached from a cycloalkenyl having 3–7 ring carbon atoms or a heterocyclic ring; said heterocyclic ring having 2–5 ring carbon atoms, 1–3 ring heteroatoms and up to a total of six ring atoms;

$R_2$ is $-N(R_3)_2$ or a 5 to 7 membered nitrogen containing heterocyclic ring which has zero or up to two oxygen ring atoms, which heterocyclic ring is unsubstituted or substituted with at least one alkyl or substituted or unsubstituted arylalkyl substituent, said alkyl containing 1–6 carbon atoms, said nitrogen containing heterocyclic ring having up to seven ring atoms including 2–6 ring carbon atoms and 1–3 ring heteroatoms of which at least one is nitrogen, said arylalkyl being unsubstituted or substituted with a halogen, alkoxy or alkyl group;

each $R_3$ is independently hydrogen or lower alkyl;

j and y are independently an integer from 0 to 6; and q is an integer from 0 to 2.

3. The method of claim 1 wherein X is $^{123}$I, $^{124}$I, $^{125}$I, $^{131}$I, $^{18}$F, $^{76}$Br, $^{77}$Br.

4. The method of claim 1 wherein X is $^{123}$I.

5. The method of claim 1 wherein x is $^{125}$I.

6. The method of claim 2 wherein X is $^{131}$I, $^{211}$At, $^{76}$Br or $^{77}$Br.

7. The method of claim 2 wherein X is $^{131}$I.

8. The method according to claim 1 or 2 wherein each $R_1$ is independently H, halo or lower alkyl.

9. The method according to claim 1 or 2 wherein each $R_1$ is H.

10. The method according to claim 1 or 2 wherein q is 2.

11. The method of claim 10 wherein $R_1$ is alkoxy.

12. The method according to claim 1 or 2 wherein q is 1.

13. The method of claim 12 wherein $R_1$ is alkoxy.

14. The method according to claim 1 or 2 wherein q is 0.

15. The method according to claim 1 or 2 wherein $R_a$ and $R_b$ are independently H, halo, or lower alkyl.

16. The method according to claim 1 or 2 herein $R_a$ and $R_b$ are independently H or halo.

17. The method according to claim 1 or 2 wherein

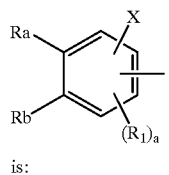

is:

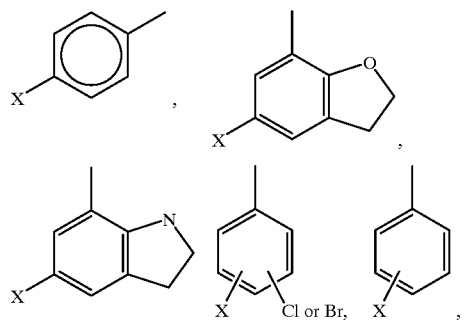

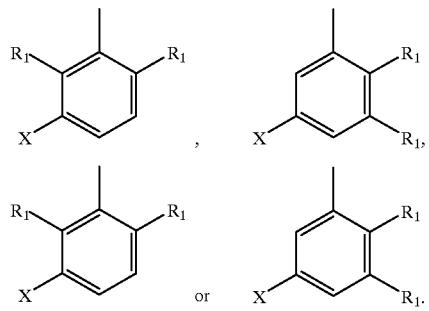

18. The method of claim 1 or 2 wherein j is 0 to 2.
19. The method of claim 1 or 2 wherein j is 0.
20. The method of claim 1 or 2 wherein y is 1 or 2.
21. The method of claim 1 or 2 wherein y is 0.
22. The method of claim 1 or 2 wherein $R_2$ is $-N(R_3)_2$.
23. The method of claim 22 wherein $R_3$ is lower alkyl.
24. The method of claim 1 or 2 wherein said heterocyclic ring formed by $-N(R_3)_2$ is:

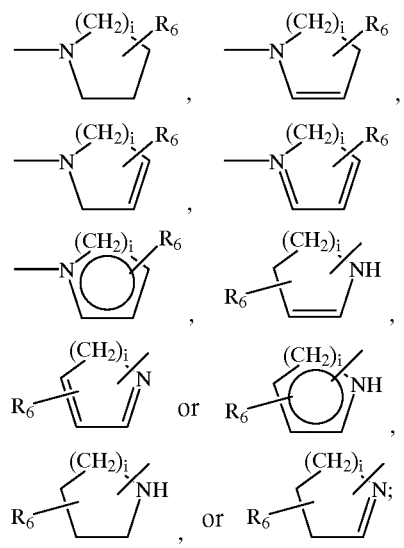

wherein $R_6$ is hydrogen or lower alkyl;

and i is an integer from 1 to 3.

25. The method of claim 1 or 2 wherein said heterocyclic ring formed by $-N(R_3)_2$ is N-piperidinyl, N-pyrrolidinyl, N-pyridinyl, N-morpholinyl, piperidinyl, pyrrolidinyl, pyridinyl or morpholinyl which can be substituted with at least one lower alkyl or substituted or unsubstituted arylalkyl.

26. The method of claim 2 wherein said tumor is a lung carcinoma, a colon carcinoma, a renal carcinoma, a melanoma, a glioma, a pheochromocytoma, prostate or breast carcinoma or a neuroblastoma.

27. The method of claim 1 or 2 wherein said lung carcinoma is an adenocarcinoma, a squamous carcinoma or a large cell lung carcinoma.

28. The method of claim 1 or 2 wherein said tumor comprises cancer cells which have a cell surface sigma receptor.

29. The method of claim 1 or 2 wherein said tumor comprises MCF-7 breast cancer cells.

30. The method of claim 1 or 2 wherein the tumor exists in women with dense breasts.

31. A method for targeting a mammalian tumor having cell surface sigma receptors present in said mammal which comprises administering to said mammal an imaging effective amount of a compound of the formula:

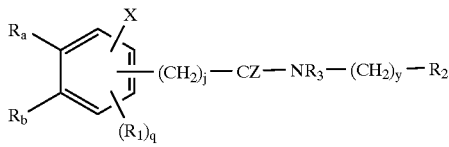

wherein:
X is a non-metal γ-emitting radionuclide;
Z is two —H;
each $R_1$ is independently H, halo, lower alkyl, or lower alkoxy;
$R_a$ and $R_b$ are independently H, halo, lower alkyl, or lower alkoxy or $R_a$ and $R_b$ together with the carbon atoms to which they are attached form a cycloalkenyl having 3–7 ring carbon atoms or a heterocyclic ring, said heterocyclic ring having 2–5 ring carbon atoms, 1–3 ring heteroatoms and up to a total of six ring atoms;
$R_2$ is —$N(R_3)_2$ or a 5 to 7 membered monocyclic nitrogen containing heterocyclic ring which has zero or up to two oxygen ring atoms, which heterocyclic ring is unsubstituted or substituted with at least one alkyl or substituted or unsubstituted arylalkyl substituent, said alkyl containing 1–6 carbon atoms, said nitrogen containing heterocyclic ring having up to seven ring atoms including 2–6 ring carbon atoms and 1–3 ring heteroatoms of which at least one is nitrogen, said arylalkyl being unsubstituted or substituted with a halogen, alkoxy or alkyl group;
each $R_3$ is independently hydrogen or lower alkyl;
j and y are independently an integer from 0 to 6;
q is an integer from 0 to 2;
and detecting the image said tumor having sigma receptors, wherein said tumor is selected from the group consisting of lung carcinoma, colon carcinoma, renal carcinoma, melanoma, glioma, pheochromocytoma, prostrate carcinoma, neural tumor, breast carcinoma, neuroblastoma, and brain carcinoma.

32. The method of claim 31 wherein said tissue is a neural tissue.

33. The method of claim 32 wherein said tissue is brain tissue.

34. The method of claim 31 wherein X is $^{123}I$, $^{124}I$, $^{125}I$, $^{131}I$, $^{18}F$, $^{76}Br$, $^{77}Br$.

35. The method of claim 32 wherein X is $^{123}I$.

36. The method of claim 1 or 2 wherein said tumor comprises T47-D breast cancer cells.

37. The method of claim 1 or 2 wherein said tumor comprises MDA-MB-231 breast cancer cells.

38. The method of claim 1 or 2 wherein said heterocyclic ring formed by —$N(R_3)_2$ is homopiperidine or morpholino.

39. The method of claim 1, 2 or 31 wherein the compound is N-[(4-($^{125}I$-iodophenyl)ethyl)]-N-methyl-2-(1-piperidinyl)ethylamine.

40. The method of claim 1 or 2 wherein said compound is

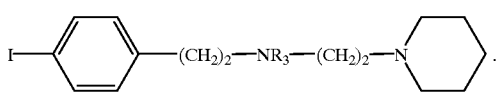

41. The method of claim 31 wherein said compound is

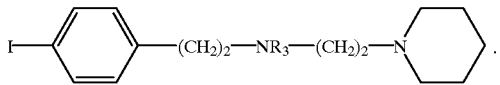

42. The method of claim 1 or 2 wherein $R_2$ is a 5 to 7 membered nitrogen containing heterocyclic ring which has 0–2 oxygen ring atoms, which heterocyclic ring is unsubstituted or substituted with at least one alkyl or unsubstituted or substituted arylalkyl substituent, said alkyl containing 1–6 carbon atoms, said nitrogen containing heterocyclic ring having up to seven ring atoms, including 2–6 ring carbon atom and 1–3 ring heteroatoms of which at least one is nitrogen, and said arylalkyl being unsubstituted or substituted with a halogen, alkyl or alkyl group.

* * * * *

UNITED STATES PATENT AND TRADEMARK OFFICE
CERTIFICATE OF CORRECTION

PATENT NO.  : 5,911,970
DATED       : June 15, 1999
INVENTOR(S) : Christy S. John et al.

It is certified that error appears in the above-identified patent and that said Letters Patent is hereby corrected as shown below:

Title page, Item [54] and Column 1, lines 1-3,
"METHODS FOR CANCER IMAGING AND THERAPY USING BENZAMINE COMPOUNDS" should read -- COMPOUNDS FOR CANCER IMAGING AND THERAPY --
Item [56], FOREIGN PATENT DOCUMENTS, delete "317873 5/1989 European Pat. Off.."
OTHER PUBLICATIONS, "23-55" should read -- 2355 --

Column 7,
Line 14, "$(CH_2)$" should read -- $(CH_2)_j$ --

Column 9,
Line 4, insert the following: -- In a preferred embodiment the --

Column 18,
Line 7, "I" should read -- $^{131}I$ --

Column 30,
Line 8, "Ki" should read -- $K_i$ --

Column 34,
Line 19, "pC" should read -- $\mu C$ --

Column 35,
Line 45, "0.1.22" should read -- 0.122 --

Column 37,
Line 34, "(0.09)" should read -- (0.00) --

Column 38,
Line 11, "pC" should read -- $\mu C$ --

UNITED STATES PATENT AND TRADEMARK OFFICE
CERTIFICATE OF CORRECTION

PATENT NO.    : 5,911,970
DATED         : June 15, 1999
INVENTOR(S)   : Christy S. John et al.

It is certified that error appears in the above-identified patent and that said Letters Patent is hereby corrected as shown below:

Column 41,
Line 40, "$^{125}$I]" should read -- [$^{125}$I] --

Column 42,
Line 9, "$^{131}$-I-N..." should begin a new paragraph.

Signed and Sealed this

Twenty-second Day of October, 2002

Attest:

JAMES E. ROGAN
Attesting Officer       Director of the United States Patent and Trademark Office